US012600969B2

(12) United States Patent
    Whyteside

(10) Patent No.: US 12,600,969 B2
(45) Date of Patent: *Apr. 14, 2026

(54) EXPRESSION CONTROL USING A REGULATABLE INTRON

(71) Applicant: ASKBIO INC., RTP, NC (US)

(72) Inventor: Graham Whyteside, Falkirk (GB)

(73) Assignee: Askbio Inc., Research Triangle Park, NC (US)

( * ) Notice: Subject to any disclaimer, the term of this patent is extended or adjusted under 35 U.S.C. 154(b) by 209 days.

This patent is subject to a terminal disclaimer.

(21) Appl. No.: 17/981,146

(22) Filed: Nov. 4, 2022

(65) Prior Publication Data

US 2023/0304003 A1     Sep. 28, 2023

Related U.S. Application Data

(63) Continuation of application No. 16/640,434, filed as application No. PCT/GB2018/052387 on Aug. 22, 2018, now Pat. No. 11,492,618.

(30) Foreign Application Priority Data

Aug. 23, 2017     (GB) ..................................... 1713545

(51) Int. Cl.

| C07H 21/02 | (2006.01) |
| A61K 48/00 | (2006.01) |
| C07H 21/04 | (2006.01) |
| C12N 15/113 | (2010.01) |
| C12N 15/85 | (2006.01) |

(52) U.S. Cl.
    CPC ........ *C12N 15/113* (2013.01); *A61K 48/0066* (2013.01); *C12N 15/85* (2013.01); *C12N 2320/30* (2013.01)

(58) Field of Classification Search
    CPC .................................................. C12N 15/113
    See application file for complete search history.

(56) References Cited

U.S. PATENT DOCUMENTS

| 2004/0170622 A1 | 9/2004 | Glimcher et al. |
| 2007/0111258 A1 | 5/2007 | Kaufman et al. |
| 2009/0232738 A1 | 9/2009 | Glimcher et al. |

FOREIGN PATENT DOCUMENTS

| JP | 2004081143 A | 3/2004 |
| WO | 2010151827 A1 | 12/2010 |
| WO | 2019014072 A1 | 1/2019 |
| WO | 2021195491 A2 | 9/2021 |

OTHER PUBLICATIONS

Anonymous. "Dr Graham Whyteside attending", 9th Annual Bioprocessing Summit: Aug. 19 to Aug. 21, 2017 Aug. 18, 2017 (Aug. 18, 2017), Retrieved from the internet: URL: http://www.synpromics.com/news-media/events/9th-annual-bioprocessing-summit.
Dunys et al. "The transcription factor X-box binding protein-1 in neurodegenerative diseases." Molecular neurodegeneration 9(35) (2014): 1-8.
Ghosh et al. "Transcriptional regulation of VEGF-A by the unfolded protein response pathway." PloS One 5(3): e9575 pp. 1-12 (2010).
Peschek et al. "A conformational RNA zipper promotes intron ejection during non-conventional XBP1 mRNA splicing." EMBO reports 16(12): 1688-1698 (2015).
Shamu. "Splicing: HACking into the unfolded-protein response." Current Biology 8(4): R121-R123 (1998).
Whyteside et al., "Inducible synthetic promoters for theproduction of gene therapy viral vectors (Poster presentation)", Aug. 24, 2017 (Aug. 24, 2017), Synpromics Retrieved from the Internet: URL:https://www.synpromics.com/sites/default/files/documents/Poster-Inducible-Promoters-For-Bioprocessing.pdf.

*Primary Examiner* — Amy Rose Hudson

(74) *Attorney, Agent, or Firm* — NIXON PEABODY LLP; Ronald I. Eisenstein; Jeanne N. Jodoin

(57) ABSTRACT

The present invention relates to the use of a regulatory nucleic acid sequences that are able to regulate gene expression in eukaryotic cells and which are responsive to the unfolded protein response (UPR). There are disclosed regulatable introns and UPR-inducible promoters, which are able to regulate gene expression. There are also disclosed recombinant expression constructs comprising such regulatory nucleic acid sequences, whereby expression of the encoded expression product can be induced by invoking the unfolded protein response (UPR) in a eukaryotic cell containing the construct, methods of using such constructs and associated vectors, cells and suchlike.

14 Claims, 14 Drawing Sheets

Specification includes a Sequence Listing.

SYNP-ATF6-01

SYNP-ATF6-02

Fig. 7

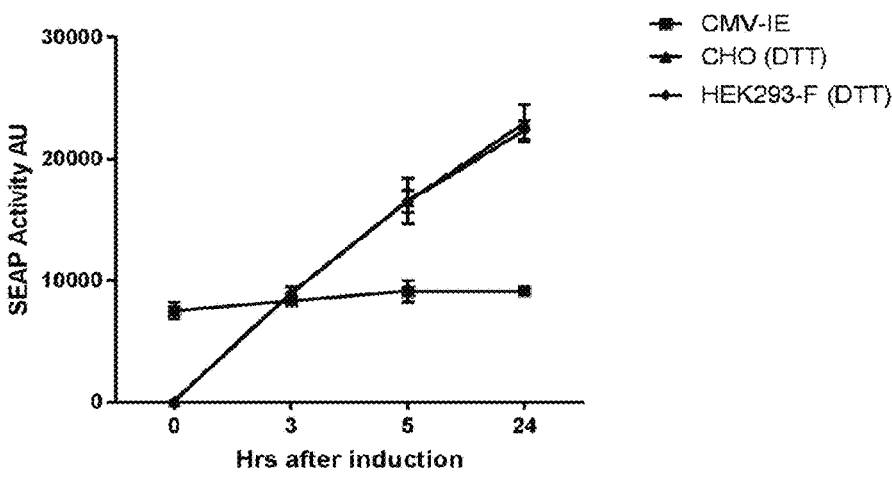
Fig. 11
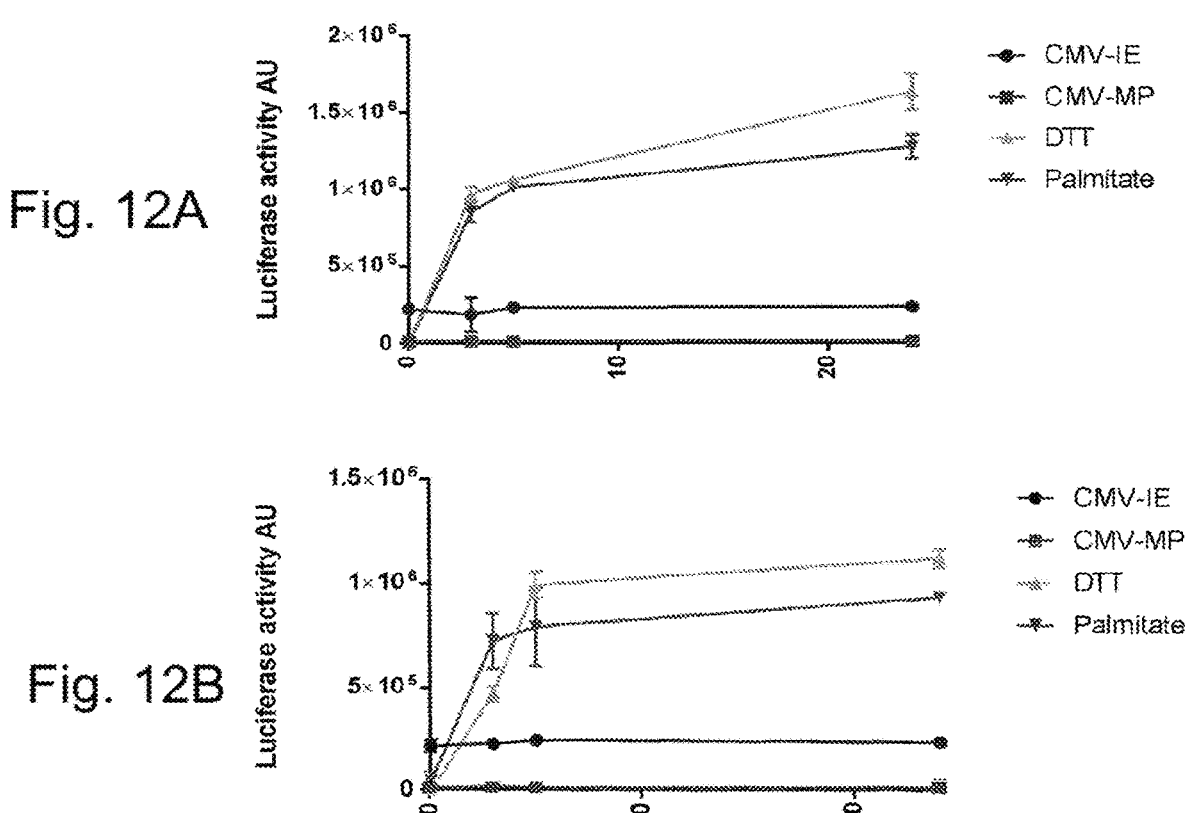
Fig. 12A
Fig. 12B

Cell viability of HEK293-F cells

Fig. 15

SEQUENCE LISTING

```
Sequence total quantity: 65
SEQ ID NO: 1             moltype = RNA  length = 20
FEATURE                  Location/Qualifiers
misc_feature             1..20
                         note = sequence of mammalian XBP1 intron inside of the IRE
                          1 cleavage sites
source                   1..20
                         mol_type = unassigned RNA
                         organism = unidentified
SEQUENCE: 1
cactcagact acgtgcacct                                                  20

SEQ ID NO: 2             moltype = RNA  length = 20
FEATURE                  Location/Qualifiers
misc_feature             1..20
                         note = variant of mammalian XBP1 intron inside of the IRE 1
                          cleavage sites
source                   1..20
                         mol_type = unassigned RNA
                         organism = unidentified
SEQUENCE: 2
```

```
cactcagact acgtgctcct                                                  20

SEQ ID NO: 3              moltype = RNA   length = 20
FEATURE                   Location/Qualifiers
misc_feature              1..20
                          note = variant of mammalian XBP1 intron inside of the IRE 1
                           cleavage sites
source                    1..20
                          mol_type = unassigned RNA
                          organism = unidentified
SEQUENCE: 3
cactcagact acgtgcccct                                                  20

SEQ ID NO: 4              moltype = RNA   length = 20
FEATURE                   Location/Qualifiers
misc_feature              1..20
                          note = variant of mammalian XBP1 intron inside of the IRE 1
                           cleavage sites
source                    1..20
                          mol_type = unassigned RNA
                          organism = unidentified
SEQUENCE: 4
cactcagact acgtgcgcct                                                  20

SEQ ID NO: 5              moltype = RNA   length = 20
FEATURE                   Location/Qualifiers
misc_feature              1..20
                          note = variant of mammalian XBP1 intron inside of the IRE 1
                           cleavage sites
source                    1..20
                          mol_type = unassigned RNA
                          organism = unidentified
SEQUENCE: 5
cactcagact atgtgcacct                                                  20

SEQ ID NO: 6              moltype = RNA   length = 33
FEATURE                   Location/Qualifiers
misc_feature              1..33
                          note = regulatable intron
misc_difference           2
                          note = misc_feature - n is a, c, g, or u
misc_difference           5
                          note = misc_feature - n is a, c, g, or u
misc_difference           28
                          note = misc_feature - n is a, c, g, or u
misc_difference           31
                          note = misc_feature - n is a, c, g, or u
source                    1..33
                          mol_type = other RNA
                          organism = synthetic construct
SEQUENCE: 6
cngcngcact cagactacgt gcacctcngc ngc                                   33

SEQ ID NO: 7              moltype = RNA   length = 33
FEATURE                   Location/Qualifiers
misc_feature              1..33
                          note = mammalian XBP1 intron sequence
source                    1..33
                          mol_type = unassigned RNA
                          organism = unidentified
SEQUENCE: 7
cagcagcact cagactacgt gcacctctgc tgc                                   33

SEQ ID NO: 8              moltype = RNA   length = 32
FEATURE                   Location/Qualifiers
misc_feature              1..32
                          note = regulatable intron
misc_difference           2
                          note = misc_feature - n is a, c, g, or u
misc_difference           31
                          note = misc_feature - n is a, c, g, or u
source                    1..32
                          mol_type = other RNA
                          organism = synthetic construct
SEQUENCE: 8
cngcagcact cagactacgt gcacctctgc ng                                    32

SEQ ID NO: 9              moltype = RNA   length = 32
FEATURE                   Location/Qualifiers
```

-continued

```
misc_feature              1..32
                          note = regulatable intron
misc_difference           2
                          note = misc_feature - n is a, c, g, or u
misc_difference           31
                          note = misc_feature - n is a, c, g, or u
source                    1..32
                          mol_type = other RNA
                          organism = synthetic construct
SEQUENCE: 9
cngcagcact cagactacgt gctcctctgc ng                                    32

SEQ ID NO: 10             moltype = RNA  length = 32
FEATURE                   Location/Qualifiers
misc_feature              1..32
                          note = regulatable intron
misc_difference           2
                          note = misc_feature - n is a, c, g, or u
misc_difference           31
                          note = misc_feature - n is a, c, g, or u
source                    1..32
                          mol_type = other RNA
                          organism = synthetic construct
SEQUENCE: 10
cngcagcact cagactacgt gcccctctgc ng                                    32

SEQ ID NO: 11             moltype = RNA  length = 32
FEATURE                   Location/Qualifiers
misc_feature              1..32
                          note = regulatable intron
misc_difference           2
                          note = misc_feature - n is a, c, g, or u
misc_difference           31
                          note = misc_feature - n is a, c, g, or u
source                    1..32
                          mol_type = other RNA
                          organism = synthetic construct
SEQUENCE: 11
cngcagcact cagactacgt gcgcctctgc ng                                    32

SEQ ID NO: 12             moltype = RNA  length = 32
FEATURE                   Location/Qualifiers
misc_feature              1..32
                          note = regulatable intron
misc_difference           2
                          note = misc_feature - n is a, c, g, or u
misc_difference           31
                          note = misc_feature - n is a, c, g, or u
source                    1..32
                          mol_type = other RNA
                          organism = synthetic construct
SEQUENCE: 12
cngcagcact cagactatgt gcacctctgc ng                                    32

SEQ ID NO: 13             moltype = RNA  length = 33
FEATURE                   Location/Qualifiers
misc_feature              1..33
                          note = regulatable intron
source                    1..33
                          mol_type = other RNA
                          organism = synthetic construct
SEQUENCE: 13
cagcagcact cagactacgt gctcctctgc tgc                                   33

SEQ ID NO: 14             moltype = RNA  length = 33
FEATURE                   Location/Qualifiers
misc_feature              1..33
                          note = regulatable intron
source                    1..33
                          mol_type = other RNA
                          organism = synthetic construct
SEQUENCE: 14
cagcagcact cagactacgt gcccctctgc tgc                                   33

SEQ ID NO: 15             moltype = RNA  length = 33
FEATURE                   Location/Qualifiers
misc_feature              1..33
                          note = regulatable intron
source                    1..33
```

```
                        mol_type = other RNA
                        organism = synthetic construct
SEQUENCE: 15
cagcagcact cagactacgt gcgcctctgc tgc                                  33

SEQ ID NO: 16          moltype = RNA   length = 33
FEATURE                Location/Qualifiers
misc_feature           1..33
                       note = regulatable intron
source                 1..33
                       mol_type = other RNA
                       organism = synthetic construct
SEQUENCE: 16
cagcagcact cagactatgt gcacctctgc tgc                                  33

SEQ ID NO: 17          moltype = RNA   length = 35
FEATURE                Location/Qualifiers
misc_feature           1..35
                       note = mammalian XBP1 intron sequence with addition of
                        trinucleotide CUG
source                 1..35
                       mol_type = other RNA
                       organism = synthetic construct
SEQUENCE: 17
cagctgcagc actcagacta cgtgcacctc tgcag                               35

SEQ ID NO: 18          moltype = DNA   length = 19
FEATURE                Location/Qualifiers
misc_feature           1..19
                       note = ERSE1 site
misc_difference        6..14
                       note = misc_feature - n is a, c, g, or t
source                 1..19
                       mol_type = unassigned DNA
                       organism = unidentified
SEQUENCE: 18
ccaatnnnnn nnnnccacg                                                  19

SEQ ID NO: 19          moltype = DNA   length = 11
FEATURE                Location/Qualifiers
misc_feature           1..11
                       note = ERSE2 site
misc_difference        6
                       note = misc_feature - n is a, c, g, or t
source                 1..11
                       mol_type = unassigned DNA
                       organism = unidentified
SEQUENCE: 19
attggnccac g                                                         11

SEQ ID NO: 20          moltype = DNA   length = 54
FEATURE                Location/Qualifiers
misc_feature           1..54
                       note = UPR inducible promoter sequence
source                 1..54
                       mol_type = unassigned DNA
                       organism = unidentified
SEQUENCE: 20
tgacgtgctt gacgtgcttg acgtgcttga cgtgcttgac gtgcttgacg tgct          54

SEQ ID NO: 21          moltype = DNA   length = 84
FEATURE                Location/Qualifiers
misc_feature           1..84
                       note = CMV-minimal promoter
source                 1..84
                       mol_type = unassigned DNA
                       organism = unidentified
SEQUENCE: 21
aggtctatat aagcagagct cgtttagtga accgtcagat cgcctagata cgccatccac    60
gctgttttga cctccataga agat                                           84

SEQ ID NO: 22          moltype = DNA   length = 169
FEATURE                Location/Qualifiers
misc_feature           1..169
                       note = inducible promoter
source                 1..169
                       mol_type = unassigned DNA
                       organism = unidentified
SEQUENCE: 22
```

-continued

```
tgacgtgctt gacgtgcttg acgtgcttga cgtgcttgac gtgcttgacg tgctggtacc   60
gtcgacgata tcggatccag gtctatataa gcagagctcg tttagtgaac cgtcagatcg  120
cctagatacg ccatccacgc tgttttgacc tccatagaag atcgccacc                169

SEQ ID NO: 23              moltype = RNA   length = 26
FEATURE                    Location/Qualifiers
misc_feature               1..26
                           note = mammalian WT intron sequence
source                     1..26
                           mol_type = unassigned RNA
                           organism = unidentified
SEQUENCE: 23
cagcactcag actacgtgca cctctg                                         26

SEQ ID NO: 24              moltype = RNA   length = 33
FEATURE                    Location/Qualifiers
misc_feature               1..33
                           note = mammalian WT intron sequence flanked by splice
                            recognition site sequnces
source                     1..33
                           mol_type = unassigned RNA
                           organism = unidentified
SEQUENCE: 24
ccgcagcact cagactacgt gcacctctgc agc                                 33

SEQ ID NO: 25              moltype = DNA   length = 717
FEATURE                    Location/Qualifiers
misc_feature               1..717
                           note = EGFP gene with intron insertion
source                     1..717
                           mol_type = other DNA
                           organism = synthetic construct
SEQUENCE: 25
atggtgagca agggcgagga gctgttcacc ggggtggtgc ccatcctggt cgagctggac   60
ggcgacgtaa acggccacaa gttcagcgtg tccggcgagg gcgagggcga tgccacctac  120
ggcaagctga ccctgaagtt catctgcacc accggcaagc tgcccgtgcc ctggcccacc  180
ctcgtgacca ccctgaccta cggcgtgcag tgcttcagcc gctaccccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctggggcac  420
aagctggagt acaactacaa cagccacaac gtctatatca tggccgacaa gcagaagaac  480
ggcatcaagg tgaacttcaa gatccgccac aacatcgagg acggcagcgt gcagctcgcc  540
gaccactacc agcagaacac ccccatcggc gacggccccg tgctgctgcc cgacaaccac  600
tacctgagca cccagtccgc cctgagcaaa gaccccaacg agaagcgcga tcacatggtc  660
ctgctggagt tcgtgaccgc cgccgggatc actctcggca tggacgagct gtacaag     717

SEQ ID NO: 26              moltype = AA   length = 239
FEATURE                    Location/Qualifiers
REGION                     1..239
                           note = EGFP protein sequence
source                     1..239
                           mol_type = protein
                           organism = unidentified
SEQUENCE: 26
MVSKGEELFT GVVPILVELD GDVNGHKFSV SGEGEGDATY GKLTLKFICT TGKLPVPWPT   60
LVTTLTYGVQ CFSRYPDHMK QHDFFKSAMP EGYVQERTIF FKDDGNYKTR AEVKFEGDTL  120
VNRIELKGID FKEDGNILGH KLEYNYNSHN VYIMADKQKN GIKVNFKIRH NIEDGSVQLA  180
DHYQQNTPIG DGPVLLPDNH YLSTQSALSK DPNEKRDHMV LLEFVTAAGI TLGMDELYK   239

SEQ ID NO: 27              moltype = RNA   length = 36
FEATURE                    Location/Qualifiers
misc_feature               1..36
                           note = mammalian XBP1 intron sequence with addition of
                            trinucleotide CUG
source                     1..36
                           mol_type = other RNA
                           organism = synthetic construct
SEQUENCE: 27
cagctgcagc actcagacta cgtgcacctc tgctgg                              36

SEQ ID NO: 28              moltype = DNA   length = 1150
FEATURE                    Location/Qualifiers
misc_feature               1..1150
                           note = EGFP sequence with regulatable XBP1 intron, CMV-MP
                            and SV40 polyA tail
source                     1..1150
                           mol_type = other DNA
                           organism = synthetic construct
SEQUENCE: 28
```

-continued

```
ggtaccgtcg acgatatcgg atccaggtct atataagcag agctcgttta gtgaaccgtc   60
agatcgccta gatacgccat ccacgctgtt ttgacctcca tagaagatcg ccaccatggt  120
gagcaagggc gaggagctgt tcaccggggg ggtgcccatc ctggtcgagc tggacggcga  180
cgtaaacggc cacaagttca gcgtgtccgg cgagggcgag ggcgatgcca cctacggcaa  240
gctgaccctg aagttcatct gcaccaccgg caagctgccc gtgccctggc ccaccctcgt  300
gaccaccctg acctacggcg tgcagtgctt cagccgctac cccgaccaca tgaagcagca  360
cgacttcttc aagtccgcca tgcccgaagg ctacgtccag gagcgcacca tcttcttcaa  420
ggacgacggc aactacaaga cccgcgccga ggtgaagttc gagggcgaca ccctggtgaa  480
ccgcatcgag ctgaagggca tcgacttcaa ggaggacggc aacatcctgg ggcacaaagt  540
ggagtacaac tacaacagcc acaacgtcta tatcatggcc gacaagcaga agaacggcat  600
caaggtgaac ttcaagatcc gccacaacat cgaggacggc agcgtgcagc tgcagcactc  660
agactacgtg cacctctgct ggccgaccac taccagcaga acaccccat cggcgacggc   720
cccgtgctgc tgcccgacaa ccactacctg agcacccagt ccgccctgag caaagacccc  780
aacgagaagc gcgatcacat ggtcctgctg gagttcgtga ccgccgccgg gatcactctc  840
ggcatggacg agctgtacaa gtgagacgat ccttatcgga tttttaccaca tttgtagagg  900
ttttacttgc tttaaaaaac ctcccacatc tcccctgaa cctgaaacat aaaatgaatg  960
caattgttgt tgttaacttg tttattgcag cttataatgg ttacaaataa agcaatagca  1020
tcacaaattt cacaaataaa gcattttttt cactgcattc tagttgtggt ttgtccaaac  1080
tcatcaatgt atcttatcat gtctgctcga aggcgcgccc tgggcctcat gggccttccg  1140
ctcactgccc                                                         1150
```

SEQ ID NO: 29          moltype = AA   length = 211
FEATURE                Location/Qualifiers
REGION                 1..211
                       note = truncated EGFP protein - start to first stop codon
source                 1..211
                       mol_type = protein
                       organism = synthetic construct SEQUENCE: 29
```
MVSKGEELFT GVVPILVELD GDVNGHKFSV SGEGEGDATY GKLTLKFICT TGKLPVPWPT   60
LVTTLTYGVQ CFSRYPDHMK QHDFFKSAMP EGYVQERTIF FKDDGNYKTR AEVKFEGDTL  120
VNRIELKGID FKEDGNILGH KLEYNYNSHN VYIMADKQKN GIKVNFKIRH NIEDGSVQLE  180
HSDYVHLCWP TTTSRTPPSA TAPCCCPTTT T                                 211
```

SEQ ID NO: 30          moltype = DNA   length = 889
FEATURE                Location/Qualifiers
misc_feature           1..889
                       note = SYNP-ATF6-02 construct
source                 1..889
                       mol_type = other DNA
                       organism = synthetic construct SEQUENCE: 30
```
tgacgtgctt gacgtgcttg acgtgcttga cgtgcttgac gtgcttgacg tgctggtacc   60
gtcgacgata tcggatccag gtctatataa gcagagctcg tttagtgaac cgtcagatcg  120
cctagatacg ccatccacgc tgttttgacc tccatagaag atcgccacca tggtgagcaa  180
gggcgaggag ctgttcaccg gggtggtgcc catcctggtc gagctggacg gcgacgtaaa  240
cggccacaag ttcagcgtgt ccggcgaggg cgagggcgat gccacctacg gcaagctgac  300
cctgaagttc atctgcacca ccggcaagct gcccgtgccc tggcccaccc tcgtgaccac  360
cctgacctac ggcgtgcagt gcttcagccg ctacccccgac cacatgaagc agcacgactt  420
cttcaagtcc gccatgcccg aaggctacgt ccaggagcgc accatcttct tcaaggacga  480
cggcaactac aagacccgcg ccgaggtgaa gttcgagggc gacaccctgg tgaaccgcat  540
cgagctgaag ggcatcgact tcaaggagga cggcaacatc ctggggcaca gctggagta  600
caactacaac agccacaacg tctatatcat ggccgacaag cagaagaacg catcaaggt  660
gaacttcaag atccgccaca acatcgagga cggcagcgtg cagctcgccg accactacca  720
gcagaacacc cccatcggcg acggccccgt gctgctgccc gacaaccact acctgagcac  780
ccagtccgcc ctgagcaaag accccaacga agcgcgat cacatggtcc tgctggagtt  840
cgtgaccgcc gccgggatca ctctcggcat ggacgagctg tacaagtga              889
```

SEQ ID NO: 31          moltype = DNA   length = 845
FEATURE                Location/Qualifiers
misc_feature           1..845
                       note = SYNP-ATF6-02 with excised intron sequence
source                 1..845
                       mol_type = other DNA
                       organism = synthetic construct SEQUENCE: 31
```
tgacgtgctt gacgtgcttg acgtgcttga cgtgcttgac gtgcttgacg tgctggtacc   60
gtcgacgata tcggatccag gtctatataa gcagagctcg tttagtgaac cgtcagatcg  120
cctagatacg ccatccacgc tgttttgacc tccatagaag atcgccacca tggtgagcaa  180
gggcgaggag ctgttcaccg gggtggtgcc catcctggtc gagctggacg gcgacgtaaa  240
cggccacaag ttcagcgtgt ccggcgaggg cgagggcgat gccacctacg gcaagctgac  300
cctgaagttc atctgcacca ccggcaagct gcccgtgccc tggcccaccc tcgtgaccac  360
cctgacctac ggcgtgcagt gcttcagccg ctacccccgac cacatgaagc agcacgactt  420
cttcaagtcc gccatgcccg aaggctacgt ccaggagcgc accatcttct tcaaggacga  480
cggcaactac aagacccgcg ccgaggtgaa gttcgagggc gacaccctgg tgaaccgcat  540
cgagctgaag ggcatcgact tcaaggagga cggcaacatc ctggggcaca gctggagta  600
caactacaac agccacaacg tctatatcat ggccgacaag cagaagaacg catcaaggt  660
gaacttcaag atccgccaca acatcgagga cggcagcgtg cagctcgccg accactacca  720
gcagaacacc cccatcggcg acggccccgt gctgctgccc gacaaccact acctgagcac  780
```

-continued

```
ccagtccgcc ctgagcaaag acccccaacga gaagcgcgat cacatggtcc tgctggagtt   840
cgtga                                                               845
```

SEQ ID NO: 32          moltype = DNA   length = 26
FEATURE                Location/Qualifiers
misc_feature           1..26
                       note = DNA coding for excised region of intron
source                 1..26
                       mol_type = other DNA
                       organism = synthetic construct
SEQUENCE: 32
```
cagacgggca actttacacg acgctg                                         26
```

SEQ ID NO: 33          moltype = DNA   length = 32
FEATURE                Location/Qualifiers
misc_feature           1..32
                       note = Description of Artificial Sequence: Synthetic
                        oligonucleotide
source                 1..32
                       mol_type = other DNA
                       organism = synthetic construct
SEQUENCE: 33
```
cagcagacgg gcaactttac acgacgctgc ag                                  32
```

SEQ ID NO: 34          moltype = DNA   length = 1892
FEATURE                Location/Qualifiers
misc_feature           1..1892
                       note = SEAP expression construct
source                 1..1892
                       mol_type = other DNA
                       organism = synthetic construct
SEQUENCE: 34
```
tgacgtgctg atgatgcgta gctagtagtt gacgtgctga tgatgcgtag ctagtagttg   60
acgtgctgat gatgcgtagc tagtagttga cgtgctgatg atgcgtagct agtagttgac  120
gtgctgatga tgcgtagcta gtagttgacg tgctgatgat gcgtagctag tagtgcagtt  180
agcgtagctg aggtaccgtc gacgatatcg gatccaggtc tatataagca gagctcgttt  240
agtgaaccgt cagatcgcct agatacgcca tccacgctgt tttgacctcc atagaagatc  300
gccaccatgc tgctgctgct gctgctgctg ggcctgaggc tacagctctc cctgggcatc  360
atcccagttg aggaggagaa cccggacttc tggaaccgcg aggcagccga ggccctgggt  420
gccgccaaga agctgcagcc tgcacagaca gccgccaaga acctcatcat cttcctgggc  480
gatgggatgg gggtgtctac ggtgacagct gccaggatcc taaaagggca gaagaaggac  540
aaactggggc ctgagatacc cctggctatg gaccgcttcc catatgtggc tctgtccaag  600
acatacaatg tagacaaaca tgtgccagac agtggagcca cagccacggc ctacctgtgc  660
ggggtcaagg gcaacttcca gaccattggc ttgagtgcag ccgcccgctt taaccagtgc  720
aacacgacac gcggcaacga ggtcatctcc gtgatgaatc gggccaagaa agcagggaag  780
tcagtgggag tggtaaccac cacacgagtg cagcacgcct cgccagccgg cacctacgcc  840
cacacggtga accgcaactg gtactcggac gccgacgtgc ctgcctcggc ccgccaggag  900
gggtgccagg acatcgctac gcagctcatc tccaacatgg acattgacgt gatcctaggt  960
ggaggccgaa agtacatgtt tcgcatggga accccagacc ctgagtaccc agatgactac 1020
agccaaggtg ggaccaggct ggacgggaag aatctggtgc aggaatggct ggcgaagcgc 1080
cagggtgccc ggtatgtgtg gaaccgcact gagctcatgc aggcttccct ggacccgtct 1140
gtgacccatc tcatgggcct cttttgagcct ggagacatga aatacgagat ccaccgagac 1200
tccacactgg accctcct gatggagatg acagaggctg ccctgcgcct gctgagcagg 1260
aacccccgcg gcttcttcct cttcgtggag ggtggtcgca tcgaccacgg tcatcatgaa 1320
agcaggactt accgggcact gactgaaacg atcatgttcg acgacgccat tgagaggggc 1380
ggccagctca ccagcgagga ggacacgctg agcctcgtca ctgccgacca ctcccacgtc 1440
ttctccttcg gaggctaccc cctgcgaggg agctccatct tcgggctggc ccctggcaag 1500
gcccgggaca ggaaggccta cacggtcctc ctatacggaa acggtccagg ctatgtgctc 1560
aaggacggc cccggccgga tgttaccgag agcgagagcg ggagcccgga gtatcggcag 1620
cagacggga actttacacg acgctgcagt cagcagtgcc cctggacgaa gagacacacg 1680
caggcgagga cgtggcggtg ttcgcgcgcg ccccgcaggc gcacctggtt cacggcgtgc 1740
aggagcagac cttcatagcg cacgtcatgg ccttcgccgc ctgcctggag ccctacaccg 1800
cctgcgacct ggcgcccccc gccggcacca ccgacgccgc gcaccgggt tactctagag 1860
tcggggcggc cggccgcttc gagcagacat ga                                1892
```

SEQ ID NO: 35          moltype = AA   length = 483
FEATURE                Location/Qualifiers
REGION                 1..483
                       note = truncated SEAP protein
source                 1..483
                       mol_type = protein
                       organism = synthetic construct
SEQUENCE: 35
```
MLLLLLLLGL RLQLSLGIIP VEEENPDFWN REAAEALGAA KKLQPAQTAA KNLIIFLGDG   60
MGVSTVTAAR ILKGQKKDKL GPEIPLAMDR FPYVALSKTY NVDKHVPDSG ATATAYLCGV  120
KGNFQTIGLS AAARFNQCNT TRGNEVISVM NRAKKAGKSV GVVTTTRVQH ASPAGTYAHT  180
VNRNWYSDAD VPASARQEGC QDIATQLISN MDIDVILGGG RKYMFRMGTP DPEYPDDYSQ  240
GGTRLDGKNL VQEWLAKRQG ARYVWNRTEL MQASLDPSVT HLMGLFEPGD MKYEIHRDST  300
LDPSLMEMTE AALRLLSRNP RGFFLFVEGG RIDHGHHESR AYRALTETIM FDDAIERAGQ  360
```

```
LTSEEDTLSL VTADHSHVFS FGGYPLRGSS IFGLAPGKAR DRKAYTVLLY GNGPGYVLKD  420
GARPDVTESE SGSPEYRQQT GNFTRRCSQQ CPWTKRHTQA RTWRCSRAAR RRTWFTACRS  480
RPS                                                                483

SEQ ID NO: 36          moltype = AA  length = 519
FEATURE                Location/Qualifiers
REGION                 1..519
                       note = full length SEAP protein
source                 1..519
                       mol_type = protein
                       organism = unidentified
SEQUENCE: 36
MLLLLLLLGL RLQLSLGIIP VEEENPDFWN REAAEALGAA KKLQPAQTAA KNLIIFLGDG  60
MGVSTVTAAR ILKGQKKDKL GPEIPLAMDR FPYVALSKTY NVDKHVPDSG ATATAYLCGV  120
KGNFQTIGLS AAARFNQCNT TRGNEVISVM NRAKKAGKSV GVVTTTRVQH ASPAGTYAHT  180
VNRNWYSDAD VPASARQEGC QDIATQLISN MDIDVILGGG RKYMFRMGTP DPEYPDDYSQ  240
GGTRLDGKNL VQEWLAKRQG ARYVWNRTEL MQASLDPSVT HLMGLFEPGD MKYEIHRDST  300
LDPSLMEMTE AALRLLSRNP RGFFLFVEGG RIDHGHHESR AYRALTETIM FDDAIERAGQ  360
LTSEEDTLSL VTADHSHVFS FGGYPLRGSS IFGLAPGKAR DRKAYTVLLY GNGPGYVLKD  420
GARPDVTESE SGSPEYRQQS AVPLDEETHA GEDVAVFARG PQAHLVHGVQ EQTFIAHVMA  480
FAACLEPYTA CDLAPPAGTT DAAHPGYSRV GAAGRFEQT                         519

SEQ ID NO: 37          moltype = RNA  length = 26
FEATURE                Location/Qualifiers
misc_feature           1..26
                       note = regulatable intron
source                 1..26
                       mol_type = other RNA
                       organism = synthetic construct
SEQUENCE: 37
cagacgggca actttacacg acgctg                                       26

SEQ ID NO: 38          moltype = DNA  length = 32
FEATURE                Location/Qualifiers
misc_feature           1..32
                       note = intron inserted in luciferase coding sequence
source                 1..32
                       mol_type = other DNA
                       organism = synthetic construct
SEQUENCE: 38
ccgcagacgg gcaactttac acgacgctgc ag                                32

SEQ ID NO: 39          moltype = AA  length = 501
FEATURE                Location/Qualifiers
REGION                 1..501
                       note = truncated luciferase protein
source                 1..501
                       mol_type = protein
                       organism = synthetic construct
SEQUENCE: 39
MEDAKNIKKG PAPFYPLEDG TAGEQLHKAM KRYALVPGTI AFTDAHIEVD ITYAEYFEMS  60
VRLAEAMKRY GLNTNHRIVV CSENSLQFFM PVLGALFIGV AVAPANDIYN ERELLNSMGI  120
SQPTVVFVSK KGLQKILNVQ KKLPIIQKII IMDSKTDYQG FQSMYTFVTS HLPPGFNEYD  180
FVPESFDRDK TIALIMNSSG STGLPKGVAL PHRTACVRFS HARDPIFGNQ IIPDTAILSV  240
VPFHHGFGMF TTLGYLICGF RVVLMYRFEE ELFLRSLQDY KIQSALLVPT LFSFFAKSTL  300
IDKYDLSNLH EIASGGAPLS KEVGEAVAKR FHLPGIRQGY GLTETTSAIL ITPEGDDKPG  360
AVGKVVPFFE AKVVDLDTGK TLGVNQRGEL CVRGPMIMSG YVNNPEATNA LIDKDGWLHS  420
GDIAYWDEDE HFFIVDRLKS LIKYKGYQVA PAELESILLQ HPNIFDAGVA GLPDDDAGEL  480
PAADGQLYTT LQTSCWNTVK P                                            501

SEQ ID NO: 40          moltype = AA  length = 550
FEATURE                Location/Qualifiers
REGION                 1..550
                       note = full length luciferase protein
source                 1..550
                       mol_type = protein
                       organism = unidentified
SEQUENCE: 40
MEDAKNIKKG PAPFYPLEDG TAGEQLHKAM KRYALVPGTI AFTDAHIEVD ITYAEYFEMS  60
VRLAEAMKRY GLNTNHRIVV CSENSLQFFM PVLGALFIGV AVAPANDIYN ERELLNSMGI  120
SQPTVVFVSK KGLQKILNVQ KKLPIIQKII IMDSKTDYQG FQSMYTFVTS HLPPGFNEYD  180
FVPESFDRDK TIALIMNSSG STGLPKGVAL PHRTACVRFS HARDPIFGNQ IIPDTAILSV  240
VPFHHGFGMF TTLGYLICGF RVVLMYRFEE ELFLRSLQDY KIQSALLVPT LFSFFAKSTL  300
IDKYDLSNLH EIASGGAPLS KEVGEAVAKR FHLPGIRQGY GLTETTSAIL ITPEGDDKPG  360
AVGKVVPFFE AKVVDLDTGK TLGVNQRGEL CVRGPMIMSG YVNNPEATNA LIDKDGWLHS  420
GDIAYWDEDE HFFIVDRLKS LIKYKGYQVA PAELESILLQ HPNIFDAGVA GLPDDDAGEL  480
PAADVVLEHG KTMTEKEIVD YVASQVTTAK KLRGGVVFVD EVPKGLTGKL DARKIREILI  540
KAKKGGKIAV                                                         550
```

```
SEQ ID NO: 41         moltype = DNA   length = 30
FEATURE               Location/Qualifiers
misc_feature          1..30
                      note = INTC9FP intron
source                1..30
                      mol_type = other DNA
                      organism = synthetic construct
SEQUENCE: 41
acgtcagacg ggcaacttta cacgacgctg                                     30

SEQ ID NO: 42         moltype = DNA   length = 30
FEATURE               Location/Qualifiers
misc_feature          1..30
                      note = INTC9RP intron sequence
source                1..30
                      mol_type = other DNA
                      organism = synthetic construct
SEQUENCE: 42
acgtcagcgt cgtgtaaagt tgcccgtctg                                     30

SEQ ID NO: 43         moltype = DNA   length = 32
FEATURE               Location/Qualifiers
misc_feature          1..32
                      note = Regulatable intron insered in caspase 9 coding
                      sequence
source                1..32
                      mol_type = other DNA
                      organism = synthetic construct
SEQUENCE: 43
cagcagacgg gcaactttac acgacgctgc tg                                  32

SEQ ID NO: 44         moltype = DNA   length = 8008
FEATURE               Location/Qualifiers
misc_feature          1..8008
                      note = SYNP-CASP9-INT vector with intron construct
source                1..8008
                      mol_type = other DNA
                      organism = synthetic construct
SEQUENCE: 44
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg agtacattta tattggctca tgtccaatat   240
gaccgccatg ttgacattga ttattgacta gttattaata gtaatcaatt acggggtcat   300
tagttcatag cccatatatg gagttccgcg ttacataact tacggtaaat ggcccgcctg   360
gctgaccgcc caacgacccc cgcccattga cgtcaataat gacgtatgtt cccatagtaa   420
cgccaatagg gactttccat tgacgtcaat gggtggagta tttacggtaa actgcccact   480
tggcagtaca tcaagtgtat catatgccaa gtccgccccc tattgacgtc aatgacggta   540
aatggcccgc ctggcattat gcccagtaca tgaccttacg ggactttcct acttggcagt   600
acatctacgt attagtcatc gctattacca tggtgatgcg gttttggcag tacaccaatg   660
ggcgtggata gcggtttgac tcacggggat ttccaagtct ccaccccatt gacgtcaatg   720
ggagtttgtt ttggcaccaa aatcaacggg actttccaaa atgtcgtaat aaccccgccc   780
cgttgacgca aatgggcggt aggcgtgtac ggtgggaggt ctatataagc agagctcgtt   840
tagtgaaccg tcagatcctc actctcttcc gcatcgctgt ctgcgagggc cagctgttgg   900
gctcgcggtt gaggacaaac tcttcgcggt ctttccagta ctcttggatc ggaaacccgt   960
cggcctccga acggtactcc gccaccgagg gacctgagcg agtccgcatc gaccggatcg  1020
gaaaacctct cgagaaaggc gtctaaccag tcacagtcgc aaggtaggct gagcaccgtg  1080
gcgggcggca gcgggtggcg gtcggggttg tttctggcgg aggtgctgct gatgatgtaa  1140
ttaaagtagg cggtcttgag acggcggatg gtcgaggtga ggtgtgggtt tagtgaaccg  1200
tcagatcctc actctcttcc gcatcgctgt ctgcgagggc cagctgtcag gcttgagatc  1260
cagctgttgg ggtgagtact ccctctcaaa agcgggcatt acttctgcgc taagattgtc  1320
agtttccaaa aacgaggagg atttgatatt cacctggccc gatctggcca tacacttgag  1380
tgacaatgac atccactttg cctttctctc cacaggtgtc cactcccagg tccaagttta  1440
aactttaata cgactcacta taggggccgc caccaagtct ggtacatgga cgaagcggat  1500
cggcggctcc tgcggcggtg ccggctgcgg ctggtggaag agctgcaggt ggaccagctc  1560
tgggacgccc tgctgagccg cgagctgttc aggccccata tgatcgagga catccagcgg  1620
gcaggctctg gatctcggcg ggatcaggcc aggcagctga tcatagatct ggagactcga  1680
gggagtcagg ctcttccttt gttcatctcc tgcttagagg acacaggcca ggacatgctg  1740
gcttcgtttc tgcgaactaa caggcaagca gcaaagttgt cgaagccaac cctagaaaac  1800
cttaccccag tggtgctcag accagagatt cgcaaaccag aggttctcag accggaaaca  1860
cccagaccag tggacattgg ttctggagga ttcggtgatg tcggtgctct tgagagtttg  1920
aggggaaatg cagatttggc ttacatcctg agcatggagc cctgtggcca ctgcctcatt  1980
atcaacaatg tgaacttctg ccgtgagtcc gggctccgca cccgcactgg ctccaacatc  2040
gactgtgaga agttgcggcg tcgcttctcc tcgctgcatt tcatggtgga ggtgaaggac  2100
gacctgactg ccaagaaaat ggtgctggct ttgctggagc tggcgcagca ggaccacggt  2160
gctctggact gctgcgtggt ggtcattctc tctcacggct gtcaggccag ccacctgcag  2220
ttcccagggg ctgtctacgg cacagatgga tgccctgtgt cggtcgagaa gattgtgaac  2280
atcttcaatg gaccagctg ccccagcctg ggagggaagc ccaagctctt tttcatccag  2340
gcctgtggtg gggagcagaa agaccatggg tttgaggtgg cctccacttc ccctgaagac  2400
```

-continued

```
gagtcccctg gcagtaaccc cgagccagat gccacccgt tccaggaagg tttgaggacc  2460
ttcgaccagc tggacgccat atctagtttg cccacaccca gtgacatctt tgtgtcctac  2520
tctactttcc caggttttgt ttcctggagg daccccaaga gtggctcctg gtcagacggg  2580
caactttaca cgacgctgga gaccctggac gacatctttg agcagtgggc tcactctgaa  2640
gacctgcagt ccctcctgct tagggtcgct aatgctgttt cggtgaaagg gatttataaa  2700
cagatgcctg gttgctttaa tttcctccga aaaaaacttt tctttaaaac atcaggggt  2760
ggaggctctg tgagcaaggg cgaggagctg ttcaccgggg tggtgcccat cctggtcgag  2820
ctggacggcg acgtaaacgg ccacaagttc agcgtgtccg gcgagggcga gggcgatgcc  2880
acctacggca agctgaccct gaagttcatc tgcaccaccg gcaagctgcc cgtgccctgg  2940
cccacccccg tgaccaccct gacctacggc gtgcagtgct tcagccgcta ccccgaccac  3000
atgaagaagc acgacttctt caagtccgcc atgcccgaag gctacgtcca ggagcgcacc  3060
atcttcttca aggacgacgg caactacaag acccgcgccg aggtgaagtt cgagggcgac  3120
accctggtga accgcatcga gctgaagggc atcgacttca aggaggacgg caacatcctg  3180
gggcacaagc tggagtacaa ctacaacagc cacaacgtct atatcatggc cgacaagcag  3240
aagaacggca tcaaggctaa cttcaaggtt cgccacaaca tcgaggacgg cagcgtgcag  3300
ctcgccgacc actaccagca gaacacccc atcggcgacg gccccgtgct gctgcccgac  3360
aaccactacc tgagcaccca gtccgccctg agcaaagacc ccaacgagaa gcgcgatcac  3420
atggtcctgc tggagttcgt gaccgccgcc gggatcactc tcggcatgga cgagctgtac  3480
aagtaaactc gagtctagag cggccgccga attcgggccc gtttaaaccc gctgatcagc  3540
ctcgactgtg ccttctagtt gccagccatc tgttgtttgc ccctccccg tgccttcctt  3600
gaccctggaa ggtgccactc ccactgtcct ttcctaataa aatgaggaaa ttgcatcgca  3660
ttgtctgagt aggtgtcatt ctattctggg gggtggggg gggcaggaca gcaagggggg  3720
ggattgggaa gacaatagca ggcatgctgg ggatgcggtg ggctctatgg cttctgaggc  3780
ggaaagaacc agctggggct ctagggggta tccccacgcg ccctgtagcg cgcattaag  3840
cgcggcgggt gtggtggtta cgcgcagcgt gaccgctaca cttgccagcg ccctagcgc  3900
cgctccttc gctttcttcc ttcctttct cgccacgttc gcaggctttc cccgtcaagc  3960
tctaaatcgg gggctccctt tagggttccg atttagtgct ttacggcacc tcgaccccaa  4020
aaaacttgat tagggtgatg gttcacgtag tgggccatcg ccctgataga cggttttcg  4080
cccttttgacg ttggagtcca cgttctttaa tagtggactc ttgttccaaa ctggaacaac  4140
actcaaccct atctcggtct attctttga tttataaggg attttgccga tttcggccta  4200
ttggttaaaa aatgagctga tttaacaaaa atttaacgcg aattaattct gtggaatgtg  4260
tgtcagttag ggtgtggaaa gtccccaggc tccccagcag gcagaagtat gcaaagcatg  4320
catctcaatt agtcagcaac caggtgtgga aagtccccag gctccccagc aggcagaagt  4380
atgcaaagca tgcatctcaa ttagtcagca accatagtcc cgcccctaac tccgcccatc  4440
ccgcccctaa ctccgcccag ttccgcccat tctccgcccc atggctgact aattttttt  4500
atttatgcag aggccgaggc cgcctctgcc tctgagctat tccagaagta gtgaggaggc  4560
ttttttggag gcctaggctt ttgcaaaaag ctctcgggag cttgtatatc cattttcgga  4620
tctgatcagc acgtgatgaa aaagcctgaa ctcaccgcga cgtctgtcga agtttctg  4680
atcgaaaagt tcgacagcgt ctccgacctg atgcagctct cggagggcga gaatctcgt  4740
gctttcagct tcgatgtagg agggcgtgga tatgtcctgc gggtaaatag ctgcgccgat  4800
ggtttctaca aagatcgtta tgtttatcgg cactttgcat cggccgcgct cccgattccg  4860
gaagtgcttg acattgggga attcagcgag agcctgacct attgcatctc ccgccgtgca  4920
cagggtgtca cgttgcaaga cctgcctgaa accgaactgc ccgctgttct gcagccggtc  4980
gcggaggcca tggatgcgat cgctgcggcc gatcttagcc agacgagcgg gttcggccca  5040
ttcggaccgc aaggaatcgg tcaatacact acatggcgtg atttcatatg cgcgattgct  5100
gatcccatg tgtatcactg gcaaactgtg atggacgaca ccgtcagtgc gtccgtcgcg  5160
caggctctcg atgagctgat gctttgggcc gaggactgcc gcaagtccg gcacctcgtg  5220
cacgcggatt tcggctccaa caatgtcctg acggacaatg gccgcataac agcggtcatt  5280
gactggagcg aggcgatgtt cggggattcc caatacgagg tcgccaacat cttcttctgg  5340
aggccgtggt tggcttgtat ggagcagcag acgcgctact tcgagcggag gcatccggag  5400
cttgcaggat cgccgcggct ccgggcgtat atgctccgca ttggtcttga ccaactctat  5460
cagagcttgg ttgacggcaa tttcgatgat gcagcttggg cgcagggtcg atgcgacga  5520
atcgtccgat ccggagccgg gactgtcggg cgtacacaaa tcgcccgcag aagcgcggcc  5580
gtctggaccg atggctgtgt agaagtactc gccgatagtg gaaaccgacg ccccagcact  5640
cgtccgaggg caaaggaata gcacgtgcta cgagatttcg attccaccgc cgccttctat  5700
gaaaggttgg gcttcggaat cgttttccgg gacgctggct ggatgatcct ccagcgcggg  5760
gatctcatgc tggagttctt cgcccacccc aacttgttta ttgcagctta taatggttac  5820
aaataaagca atagcatcac aaatttcaca aataaagcat tttttcact gcattctagt  5880
tgtggtttgt ccaaactcat caatgtatct tatcatgtct gtataccgtc gacctcatgc  5940
tagagcttgg cgtaatcatg gtcatagctg tttcctgtgt gaaattgtta tccgctcaca  6000
attccacaca acatacgagc cggaagcata aagtgtaaag cctggggtgc ctaatgagtg  6060
agctaactca cattaattgc gttgcgctca ctgcccgctt tccagtcggg aaacctgtcg  6120
tgccagctgc attaatgaat cggccaacgc gcggggagag gcggtttgcg tattgggcgc  6180
tcttccgctt cctcgctcac tgactcgctg cgctcggtcg ttcggctgcg gcgagcggta  6240
tcagctcact caaaggcggt aatacggtta tccacagaat caggggataa cgcaggaaag  6300
aacatgtgag caaaaggcca gcaaaaggcc aggaaccgta aaaaggccgc gttgctggcg  6360
tttttccata ggctccgccc ccctgacgag catcacaaaa atcgacgctc aagtcagagg  6420
tggcgaaacc cgacaggact ataaagatac caggcgtttc cccctggaag ctccctcgtg  6480
cgctctcctg ttccgaccct gccgcttacc ggatacctgt ccgcctttct cccttcggga  6540
agcgtggcgc tttctcatag ctcacgctgt aggtatctca gttcggtgta ggtcgttcgc  6600
tccaagctgg gctgtgtgca cgaacccccc gttcagcccg accgctgcgc cttatccggt  6660
aactatcgtc ttgagtccaa cccggtaaga cacgacttat cgccactggc agcagccact  6720
ggtaacagga ttagcagagc gaggtatgta ggcggtgcta cagagttctt gaagtggtgg  6780
cctaactacg gctacactag aagaacagta tttggtatct gcgctctgct gaagccagtt  6840
accttcggaa aaagagttgg tagctcttga tccggcaaac aaaccaccgc tggtagcggt  6900
ggtttttttg tttgcaagca gcagattacg cgcagaaaaa aaggatctca agaagatcct  6960
ttgatctttt ctacggggtc tgagcgcgga ccctatt gttattttt ctaaatacat  7020
tcaaatatgt atccgctcat gaattaattc ttagaaaaac tcatcgagca tcaaatgaaa  7080
ctgcaattta ttcatatcag gattatcaat accatatttt gaaaaagcc gtttctgtaa  7140
```

```
tgaaggagaa aactcaccga ggcagttcca taggatggca agatcctggt atcggtctgc   7200
gattccgact cgtccaacat caatacaacc tattaatttc ccctcgtcaa aaataaggtt   7260
atcaagtgag aaatcaccat gagtgacgac tgaatccggt gagaatggca aaagtttatg   7320
catttctttc cagacttgtt caacaggcca gccattacgc tcgtcatcaa aatcactcgc   7380
atcaaccaaa ccgttattca ttcgtgattg cgcctgacgg agacgaaata cgcgatcgat   7440
gttaaaagga caattacaaa caggaatcga atgcaaccgg cgcaggaaca ctgccagcgc   7500
atcaacaata ttttcacctg aatcaggata ttcttctaat acctggaatg ctgtttccc   7560
agggatcgca gtggtgagta accatgcatc atcaggagta cggataaaat gcttgatggt   7620
cggaagaggc ataaattccg tcagccagtt tagtctgacc atctcatctg taacatcatt   7680
ggcaacgcta cctttgccat gtttcagaaa caactctggc gcatcgggct tcccatacaa   7740
tcgatagatt gtcgcacctg attgcccgac attatcgcga gcccatttat acccatataa   7800
atcagcatcc atgttggaat ttaatcgcgg cctagagcaa gacgtttccc gttgaatatg   7860
gctcataaca ccccttgtat tactgtttat gtaagcagac agttttattg ttcatgacca   7920
aaatcccta acgtgagttt tcgttccact gagcgtcaga ccccgtagaa atccgcgcac   7980
atttccccga aaagtgccac ctgacgtc                                      8008

SEQ ID NO: 45                 moltype = AA   length = 371
FEATURE                       Location/Qualifiers
REGION                        1..371
                              note = truncated caspase 9
source                        1..371
                              mol_type = protein
                              organism = synthetic construct
SEQUENCE: 45
MDEADRRLLR RCRLRLVEEL QVDQLWDALL SRELFRPHMI EDIQRAGSGS RRDQARQLII   60
DLETRGSQAL PLFISCLEDT GQDMLASFLR TNRQAAKLSK PTLENLTPVV LRPEIRKPEV   120
LRPETPRPVD IGSGGFGDVG ALESLRGNAD LAYILSMEPC GHCLIINNVN FCRESGLRTR   180
TGSNIDCEKL RRRFSSLHFM VEVKGDLTAK KMVLALLELA QQDHGALDCC VVVILSHGCQ   240
ASHLQFPGAV YGTDGCPVSV EKIVNIFNGT SCPSLGGKPK LFFIQACGGE QKDHGFEVAS   300
TSPEDESPGS NPEPDATPFQ EGLRTFDQLD AISSLPTPSD IFVSYSTFPG FVSWRDPKSG   360
SWSAGDPGRH L                                                        371

SEQ ID NO: 46                 moltype = AA   length = 430
FEATURE                       Location/Qualifiers
REGION                        1..430
                              note = full length caspase 9
source                        1..430
                              mol_type = protein
                              organism = synthetic construct
SEQUENCE: 46
MDEADRRLLR RCRLRLVEEL QVDQLWDALL SRELFRPHMI EDIQRAGSGS RRDQARQLII   60
DLETRGSQAL PLFISCLEDT GQDMLASFLR TNRQAAKLSK PTLENLTPVV LRPEIRKPEV   120
LRPETPRPVD IGSGGFGDVG ALESLRGNAD LAYILSMEPC GHCLIINNVN FCRESGLRTR   180
TGSNIDCEKL RRRFSSLHFM VEVKGDLTAK KMVLALLELA QQDHGALDCC VVVILSHGCQ   240
ASHLQFPGAV YGTDGCPVSV EKIVNIFNGT SCPSLGGKPK LFFIQACGGE QKDHGFEVAS   300
TSPEDESPGS NPEPDATPFQ EGLRTFDQLD AISSLPTPSD IFVSYSTFPG FVSWRDPKSG   360
SWSADGQLYT TLLETLDDIF EQWAHSEDLQ SLLLRVANAV SVKGIYKQMP GCFNFLRKKL   420
FFKTSGGGGS                                                          430

SEQ ID NO: 47                 moltype = DNA   length = 154
FEATURE                       Location/Qualifiers
misc_feature                  1..154
                              note = UPR inducible promoter
source                        1..154
                              mol_type = other DNA
                              organism = synthetic construct
SEQUENCE: 47
tgacgtgctg atgatgcgta gctagtagtt gacgtgctga tgatgcgtag ctagtagttg   60
acgtgctgat gatgcgtagc tagtagttga cgtgctgatg atgcgtagct agtagttgac   120
gtgctgatga tgcgtagcta gtagttgacg tgct                               154

SEQ ID NO: 48                 moltype = DNA   length = 35
FEATURE                       Location/Qualifiers
misc_feature                  1..35
                              note = Regulatable intron
source                        1..35
                              mol_type = other DNA
                              organism = synthetic construct
SEQUENCE: 48
cagctgcagc actcagacta cgtgcacctc tgctg                              35

SEQ ID NO: 49                 moltype = RNA   length = 20
FEATURE                       Location/Qualifiers
misc_feature                  1..20
                              note = intron sequence inside cleavage sites
source                        1..20
                              mol_type = other RNA
                              organism = synthetic construct
SEQUENCE: 49
```

-continued

```
acgggcaact ttacacgacg                                                    20

SEQ ID NO: 50          moltype = RNA  length = 32
FEATURE                Location/Qualifiers
misc_feature           1..32
                       note = regulatable intron sequence
misc_difference        2
                       note = misc_feature - n is a, c, g, or u
misc_difference        31
                       note = misc_feature - n is a, c, g, or u
source                 1..32
                       mol_type = other RNA
                       organism = synthetic construct
SEQUENCE: 50
cngcagacgg gcaactttac acgacgctgc ng                                      32

SEQ ID NO: 51          moltype = AA  length = 5
FEATURE                Location/Qualifiers
REGION                 1..5
                       note = truncated EGFP protein - first stop codon to second
                        stop codon
source                 1..5
                       mol_type = protein
                       organism = synthetic construct
SEQUENCE: 51
APSPP                                                                    5

SEQ ID NO: 52          moltype = AA  length = 16
FEATURE                Location/Qualifiers
REGION                 1..16
                       note = truncated EGFP protein - from second stop codon to
                        third stop codon
source                 1..16
                       mol_type = protein
                       organism = synthetic construct
SEQUENCE: 52
AKTPTRSAIT WSCWSS                                                        16

SEQ ID NO: 53          moltype = AA  length = 13
FEATURE                Location/Qualifiers
REGION                 1..13
                       note = truncated EGFP protein from third stop codon to end
                        of protein
source                 1..13
                       mol_type = protein
                       organism = synthetic construct
SEQUENCE: 53
PPPGSLSAWT SCT                                                           13

SEQ ID NO: 54          moltype = DNA  length = 47
FEATURE                Location/Qualifiers
misc_feature           1..47
                       note = UPR-responsive CRE
misc_difference        8
                       note = misc_feature - optional spacer sequence
misc_difference        16
                       note = misc_feature - optional spacer sequence
misc_difference        24
                       note = misc_feature - optional spacer sequence
misc_difference        32
                       note = misc_feature - optional spacer sequence
misc_difference        40
                       note = misc_feature - optional spacer sequence
source                 1..47
                       mol_type = other DNA
                       organism = synthetic construct
SEQUENCE: 54
tgacgtgntg acgtgntgac gtgntgacgt gntgacgtgn tgacgtg                      47

SEQ ID NO: 55          moltype = DNA  length = 59
FEATURE                Location/Qualifiers
misc_feature           1..59
                       note = UPR-responsive CRE
misc_difference        10
                       note = misc_feature - optional spacer sequence
misc_difference        20
                       note = misc_feature - optional spacer sequence
misc_difference        30
                       note = misc_feature - optional spacer sequence
```

-continued

```
misc_difference        40
                       note = misc_feature - optional spacer sequence
misc_difference        50
                       note = misc_feature - optional spacer sequence
source                 1..59
                       mol_type = other DNA
                       organism = synthetic construct
SEQUENCE: 55
tgacgtgctg tgacgtgctn tgacgtgctn tgacgtgctg tgacgtgctn tgacgtgct   59

SEQ ID NO: 56          moltype = DNA   length = 154
FEATURE                Location/Qualifiers
misc_feature           1..154
                       note = UPR-responsive CRE
source                 1..154
                       mol_type = other DNA
                       organism = synthetic construct
SEQUENCE: 56
tgacgtgctg atgatgcgta gctagtagtt gacgtgctga tgatgcgtag ctagtagttg   60
acgtgctgat gatgcgtagc tagtagttga cgtgctgatg atgcgtagct agtagttgac   120
gtgctgatga tgcgtagcta gtagttgacg tgct                               154

SEQ ID NO: 57          moltype = DNA   length = 255
FEATURE                Location/Qualifiers
misc_feature           1..255
                       note = UPR-inducible promoter
source                 1..255
                       mol_type = other DNA
                       organism = synthetic construct
SEQUENCE: 57
tgacgtgctg atgatgcgta gctagtagtt gacgtgctga tgatgcgtag ctagtagttg   60
acgtgctgat gatgcgtagc tagtagttga cgtgctgatg atgcgtagct agtagttgac   120
gtgctgatga tgcgtagcta gtagttgacg tgctgatgat gcgtagctag tagtgcagtt   180
agcgtagctg aggtaccgtc gacgatatcg gatccaggtc tatataagca gagctcgttt   240
agtgaaccgt cagat                                                    255

SEQ ID NO: 58          moltype = DNA   length = 255
FEATURE                Location/Qualifiers
misc_feature           1..255
                       note = UPR-inducible promoter
source                 1..255
                       mol_type = other DNA
                       organism = synthetic construct
SEQUENCE: 58
tgacgtgctg atgatgcgta gctagtagtt gacgtgctga tgatgcgtag ctagtagttg   60
acgtgctgat gatgcgtagc tagtagttga cgtgctgatg atgcgtagct agtagttgac   120
gtgctgatga tgcgtagcta gtagttgacg tgctgatgat gcgtagctag tagtgcagtt   180
agcgtagctg aggtaccgtc gacgatatcg gatccttcgc atattaaggt gacgcgtgtg   240
gcctcgaaca ccgag                                                    255

SEQ ID NO: 59          moltype = DNA   length = 2269
FEATURE                Location/Qualifiers
misc_feature           1..2269
                       note = Construct ATF06-MP-001
source                 1..2269
                       mol_type = other DNA
                       organism = synthetic construct
SEQUENCE: 59
gaagttccta ttccgaagtt cctattctct agaaagtata ggaacttctg acgtgctgat   60
gatgcgtagc tagtagttga cgtgctgatg atgcgtagct agtagttgac gtgctgatga   120
tgcgtagcta gtagttgacg tgctgatgat gcgtagctag tagttgacgt gctgatgatg   180
cgtagctagt agttgacgtg ctgatgatgc gtagctagta gtgcagttag cgtagctgag   240
gtaccgtcga cgatatcgga tccttcgcat attaaggtgc gcgtgtggc ctcgaacacc    300
gagcgaaccct gcagcgaccc gcttaaatgg aagatgccaa aacattaag aagggcccag    360
cgccattcta cccactcgaa gacgggaccg ccggcgagca gctgcacaaa gccatgaagc   420
gctacgccct ggtgcccggc accatcgcct ttaccgacgc acatatcgag gtggacatta   480
cctacgccga gtacttcgag atgagcgttc ggctggcaga agctatgaag cgctatgggc   540
tgaatacaaa ccatcggatc gtggtgtgca gcgagaatag cttgcagttc ttcatgcccg   600
tgttgggtgc cctgttcatc ggtgtggctg tggccccagc taacgacatc tacaacgagc   660
gcgagctgct gaacagcatg ggcatcagcc agcccaccgt cgtattcgtg agcaagaaag   720
ggctgcaaaa gatcctcaac gtgcaaaaga agctaccgat catacaaaag atcatcatca   780
tggatagcaa gaccgactac cagggcttcc aaagcatgta caccttcgtg acttccattt   840
gccacccgg cttcaacgag tacgacttcg tgcccgagag cttcgaccgg acaaaaacca   900
tcgccctgat catgaacagt agtggcagta ccggattgcc caagggcgta gccctaccgc   960
accgcaccgc ttgtgtccga ttcagtcatg cccgcgaccc catcttcggc aaccagatca   1020
tccccgacac cgctatcctc agcgtggtgc catttcacca cggcttcggc atgttcacca   1080
cgctgggcta cttgatctgc ggctttcggg tcgtgctcat gtaccgcttc gaggaggagc   1140
tattcttgcg cagcttgcaa gactataaga ttcaatctgc cctgctggtg cccacactat   1200
ttagcttctt cgctaagagc actctcatcg acaagtacga cctaagcaac ttgcacgaga   1260
```

-continued

```
tcgccagcgg cggggcgccg ctcagcaagg aggtaggtga ggccgtggcc aaacgcttcc    1320
acctaccagg catccgccag ggctacggcc tgacagaaac aaccagcgcc attctgatca    1380
cccccgaagg ggacgacaag cctggcgcag taggcaaggt ggtgcccttc ttcgaggcta    1440
aggtggtgga cttggacacc ggtaagacac tgggtgtgaa ccagcgcggc gagctgtgcg    1500
tccgtggccc catgatcatg agcggctacg ttaacaaccc cgaggctaca aacgctctca    1560
tcgacaagga cggctggctg cacacgcggc acatcgccta ctgggacgag gacgagcact    1620
tcttcatcgt ggaccggctg aagagcctga tcaaatacaa gggctaccag gtagccccag    1680
ccgaactgga gagcatcctg ctgcaacacc ccaacatctt cgacgccggg gtcgccggcc    1740
tgcccgacga cgatgccggc gagctgcccg ccgcagtcgt cgtgctggaa cacggtaaaa    1800
ccatgaccga gaaggagatc gtggactatg tggccagcca ggttacaacc gccaagaagc    1860
tgcgcggtgg tgttgtgttc gtggacgagg tgcctaaagg actgaccggc aagttggacg    1920
cccgcaagat ccgcgagatt ctcattaagg ccaagaaggg cggcaagatc gccgtgtaat    1980
gaaagcttgg tctctacgag taatagacgc ccagttgaat tccttcgagc agacatgata    2040
agatacattg atgagtttgg acaaaccaca actagaatgc agtgaaaaaa atgctttatt    2100
tgtgaaattt gtgatgctat tgctttattt gtaaccatta taagctgcaa taaacaagtt    2160
aacaacaaca attgcattca ttttatgttt caggttcagg gggaggtgtg ggaggttttt    2220
taaagcaagt aaaacctcta caaatgtggt aaaatcgata aggatccgt               2269
```

SEQ ID NO: 60          moltype = DNA  length = 2425
FEATURE                Location/Qualifiers
misc_feature           1..2425
                       note = Costruct ATF06-MP-002
source                 1..2425
                       mol_type = other DNA
                       organism = synthetic construct
SEQUENCE: 60

```
gcgacgtaat acgactcact atagggcgaa ttggcggaag gccgtcaagg ccgcatgcat    60
aataaaatat ctttattttc attacatctg tgtgttggtt ttttgtgtgt gacgtgctga    120
tgatgcgtag ctagtagttg acgtgctgat gatgcgtagc tagtagttga cgtgctgatg    180
atgcgtagct agtagttgac gtgctgatga tgcgtagcta gtagttgac tgctgatgat    240
gcgtagctag tagttgacgt gctgatgatg cgtagctagt agtgcagtta gcgtagctga    300
ggtaccgtcg acgatatcgg atccaggtct atataagcag agctcgttta gtgaaccgtc    360
agatcgccta gatacgccat ccacgctgtt ttgacctcca tagaagatcg ccaccatgga    420
agatgccaaa aacattaaga agggcccagc gccattctac caactcgaag acgggaccgc    480
cggcgagcag ctgcacaaag ccatgaagcg ctacgccctg gtgcccggca ccatcgcctt    540
taccgacgca catatcgagg tggacattac ctacgccgag tacttcgaga tgagcgttcg    600
gctggcagaa gctatgaagc gctatgggct gaatacaaac catcggatcg tggtgtgcag    660
cgagaatagc ttgcagttct tcatgcccgt gttgggtgcc ctgttcatcg gtgtggctgt    720
ggcccagct aacgacatct acaacgagcg cgagctgctg aacagcatgg gcatcagcca    780
gcccaccgtc gtattcgtga gcaagaaagg gctgcaaaag atcctcaacg tgcaaaagaa    840
gctaccgatc atacaaaaga tcatcatcat ggatagcaag accgactacc agggcttcca    900
aagcatgtac accttcgtga cttcccattt gccacccggc ttcaacgagt acgacttcgt    960
gcccgagagc ttcgaccggg acaaaaccat cgccctgatc atgaacagta gtggcagtac    1020
cggattgccc aagggcgtag ccctaccgca ccgcaccgct tgtgtccgat tcagtcatgc    1080
ccgcgacccc atcttcggca accagatcat ccccgacacc gctatcctca gcgtggtgcc    1140
atttcaccac ggcttcggca tgttcaccac gctgggctac ttgatctgcg gctttcgggt    1200
cgtgctcatg taccgcttcg aggaggagct attcttgcac agctgcaag actataagat    1260
tcaatctgcc ctgctggtgc ccacactatt tagcttcttc gctaagagca ctctcatcga    1320
caagtacgac ctaagcaact tgcacgagat cgccagcggc ggggcgccgc tcagcaagga    1380
ggtaggtgag gccgtggcca aacgcttcca cctaccaggc atccgccagg ctacggcct    1440
gacagaaaca accagcgcca ttctgatcac ccccgacacc gacgacaagc ctggcgcagt    1500
aggcaaggtg gtgcccttct cgaggctaa ggtggtggac ttggacaccg gtaagacact    1560
gggtgtgaac cagcgcggcg agctgtgcgt ccgtggcccc atgatcatga gcggctacgt    1620
taacaacccc gaggctacaa acgctctcat cgacaaggac ggctggctgc acacgcggcga    1680
catcgcctac tgggacgagg acgagcactt cttcatcgtg gaccggctga agagcctgat    1740
caaatacaag ggctaccagg tagccccagc cgaactggag agcatcctgc tgcaacaccc    1800
caacatcttc gacgccgggg tcgccggcct gcccgacgac gatgccggcg agctgcccgc    1860
cgcagtcgtc gtgctggaac acggtaaaac catgaccgag aaggagatcg tggactatgt    1920
ggccagccag gttacaaccg ccaagaagct gcgcggtggt gttgtgttcg tggacgaggt    1980
gcctaaagga ctgaccggca agttggacgc ccgcaagatc cgcgagattc tcattaaggc    2040
caagaagggc ggcaagatcg ccgtgtaatg aaagcttggt ctctacgagt aatagacgcc    2100
cagttgaatt ccttcgagca gacatgataa gatacattga tgagtttgga caaaccacaa    2160
ctagaatgca gtgaaaaaaa tgctttattt gtgaaatttg tgatgctatt gctttatttg    2220
taaccattat aagctgcaat aaacaagtta acaacaacaa ttgcattcat tttatgtttc    2280
aggttcaggg ggaggtgtgg gaggtttttt aaagcaagta aaacctctac aaatgtggta    2340
aaatcgataa ggatccgtct gggcctcatg ggccttccgc tcactgcccg ctttccagtc    2400
gggaaacctg tcgtgccagc tgcat                                          2425
```

SEQ ID NO: 61          moltype = DNA  length = 20
FEATURE                Location/Qualifiers
misc_feature           1..20
                       note = Spacer sequence
source                 1..20
                       mol_type = other DNA
                       organism = synthetic construct
SEQUENCE: 61

```
gatgatgcgt agctagtagt                                                20
```

SEQ ID NO: 62          moltype = RNA  length = 72

-continued

```
FEATURE              Location/Qualifiers
misc_feature         1..72
                     note = Description of Artificial Sequence: Synthetic
                      oligonucleotide
source               1..72
                     mol_type = other RNA
                     organism = synthetic construct
SEQUENCE: 62
ggagccccga gtatcggcag cagacgggca actttacacg acgctgcagt cagcagtgcc   60
cctggacgaa ga                                                        72

SEQ ID NO: 63        moltype = RNA   length = 96
FEATURE              Location/Qualifiers
misc_feature         1..96
                     note = Description of Artificial Sequence: Synthetic
                      oligonucleotide
source               1..96
                     mol_type = other RNA
                     organism = synthetic construct
SEQUENCE: 63
cgccacaaca tcgaggacgg cagcgtgcag ctgcagcact cagactacgt gcacctctgc   60
tggccgacca ctaccagcag aacaccccca tcggcg                             96

SEQ ID NO: 64        moltype = RNA   length = 73
FEATURE              Location/Qualifiers
misc_feature         1..73
                     note = Description of Artificial Sequence: Synthetic
                      oligonucleotide
source               1..73
                     mol_type = other RNA
                     organism = synthetic construct
SEQUENCE: 64
gggaccccaa gagtggctcc tggtcagacg ggcaacttta cacgacgctg gagaccctgg   60
acgacatctt tga                                                      73

SEQ ID NO: 65        moltype = RNA   length = 72
FEATURE              Location/Qualifiers
misc_feature         1..72
                     note = Description of Artificial Sequence: Synthetic
                      oligonucleotide
source               1..72
                     mol_type = other RNA
                     organism = synthetic construct
SEQUENCE: 65
atgccggcga gctgcccgcc gcagacgggc aactttacac gacgctgcag acgtcgtgct   60
ggaacacggt aa                                                       72
```

EXPRESSION CONTROL USING A REGULATABLE INTRON

CROSS REFERENCE TO RELATED APPLICATIONS

This Application is a Continuation application under 35 U.S.C. § 120 of co-pending U.S. National Stage application Ser. No. 16/640,434 filed Feb. 20, 2020 (Allowed), which is a 35 U.S.C. § 371 National Phase Entry of International Patent Application No. PCT/GB2018/052387 filed Aug. 22, 2018, which designates the U.S. and claims benefit of foreign priority under 35 U.S.C. § 119(b) of GB Application Number 1713545.0 filed Aug. 23, 2017, the contents of which are incorporated herein in their entireties by reference.

SEQUENCE LISTING

The instant application contains a Sequence Listing which has been submitted electronically in XML format and is hereby incorporated by reference in its entirety. Said XML copy, created on May 22, 2023, is named 046192-096130USC1_SL.xml and is 118,061 bytes in size.

The present invention relates to the use of a regulatory nucleic acid sequences that are able to regulate gene expression in eukaryotic cells and which are responsive to the unfolded protein response (UPR). In some aspects, the invention relates to the use of regulatable introns to control gene expression. In other aspects it relates to UPR-inducible promoters. The invention also relates to recombinant expression constructs comprising such regulatory nucleic acid sequences, whereby expression of the encoded expression product can be induced by invoking the unfolded protein response (UPR) in a eukaryotic cell containing the construct, and to methods of using such constructs and associated vectors, cells and suchlike.

BACKGROUND OF THE INVENTION

Regulatable gene expression is desirable in a great many circumstances, where it is beneficial or necessary to control the expression levels of an expression product. For example, in the case of industrial biotechnology, it can be highly advantageous to be able to induce production of an expression product (e.g. a protein) at the desired time in a fermentation process. In another example, in gene therapy it can be desirable to be able to induce expression of a therapeutic product (e.g. a therapeutic protein) at the desired time and/or location of location of treatment.

Inducible promoters are known in the art, for example the tetracycline (Tet)-on and -off inducible expression systems (Gossen M & Bujard H. *PNAS.* 1992 Jun. 15; 89(12):5547-51; Gossen M, Freundlieb S, Bender G, Müller G, Hillen W, & Bujard H. *Science.* 1995 Jun. 23; 268(5218)).

Inducible promoters work by regulating expression at the transcription level, controlling the amount of mRNA produced from the relevant expression system. While this can provide useful levels of gene expression, there is a need for additional, and ideally improved systems for controlling expression.

In particular, there is a need for improved expression control systems for the expression of toxic proteins, i.e. proteins that are toxic to the cell in which they are produced. In the case of toxic proteins, the expression of even small amounts of the protein can often cause cell death or very poor production.

Moreover, in the case of gene of cell therapy, there is a need for systems to allow expression of a therapeutic protein or RNA, or other expression product, to be induced at a desired time and/or location.

The present invention relates to regulation of expression that acts at the point of translation. In particular, it relates to the use of an intron that is spliced out as a result of the unfolded protein response (UPR) in eukaryotic cells to control expression.

The unfolded protein response (UPR) is a cellular coping mechanism for endoplasmic reticulum stress. The UPR is activated in response to an accumulation of unfolded or misfolded proteins in the lumen of the endoplasmic reticulum (ER). The UPR aims to restore normal function of the cell through various mechanisms. If these objectives are not achieved within a certain time span or the disruption is prolonged, the UPR aims towards apoptosis. The UPR can be triggered by increased protein synthesis and folding such as heterologous protein production or via other cellular stresses, e.g. chemically induced stresses such as blocking glycosylation pathways or disulphide bond formation. The UPR is highly conserved across all eukaryotes.

In mammalian cells there exists three mechanisms for ER stress to be sensed and the UPR to be activated:

1) IRE-1 Splicing of XBP-1 mRNA

ER-stress from increased protein folding demand or via chemical inhibition of ER-processes is detected by the ER transmembrane protein IRE1 via disassociation of the chaperone BiP. This disassociation of BiP activates IRE1 by allowing oligomerisation and phosphorylation of the protein which leads to an ER lumen facing RNase domain being exposed. Subsequently, the RNase domain catalyses the removal of a non-canonical intron from XBP-1 mRNA in a spliceosome-independent manner. Under non-stress conditions XBP1 mRNA is un-spliced (XBP1u) which, when translated, forms a 261 amino acid ORF that is a non-functional protein. However, when ER-stress is detected XBP1u is spliced by the IRE1 RNase to form XBP1s which encodes a functional 376 amino acid protein. This functional protein, XBP1 is a transcription factor that controls the expression of several genes involved in protein homeostasis such as chaperones, disulphide isomerases and enzymes involved in phospholipid biosynthesis. It regulates these processes by binding to specific sequences, ER stress response elements (ERSEs) or unfolded protein response elements (UPREs), and enhancing gene expression. Therefore, the control of gene expression is the removal of the mRNA intron from XBP1u by IRE1. A very similar system operates in non-mammalian eukaryotic cells.

2) ATF6

Activated transcription factor (ATF6) ATF6 is a type-2 transmembrane protein that has a transcription factor domain in the cytosolic region of the protein. It is synthesized as an inactive precursor and retained in the ER by association with BiP/GRP78. In response to stress conditions, ATF6 disassociates and is transported to the Golgi apparatus, where processing occurs to release the transcription factor domain. This domain is then transported to the nucleus where it can bind to ERSEs and UPREs to enhance expression of genes involved in protein homeostasis.

3) Double Stranded RNA-Activated Protein Kinase (PERK)

PERK is a type-1 ER transmembrane protein that contains an ER luminal stress sensor and cytosolic protein kinase domain. PERK is activated in response to ER stress and inhibits normal protein translation in the ER of mammalian cells by inactivating eukaryotic initiation factor (elF2a) via phosphorylation.

Mechanisms 1) and 2) are of most relevance to the present invention.

STATEMENTS OF THE INVENTION

According to the present invention there is provided a synthetic nucleic acid expression construct for producing an expression product in a cell, the nucleic acid expression construct comprising a promoter sequence operably linked to a nucleic acid sequence encoding an expression product, the nucleic acid sequence encoding the expression product comprising a sequence which encodes a regulatable intron, said regulatable intron being an intron which comprises an excisable sequence which is capable of being spliced out of a transcript produced from the synthetic expression construct via the unfolded protein response (UPR) system in the cell, thereby resulting in a transcript encoding a functional expression product.

Thus, the present invention is based upon the use of a regulatable intron which is capable of being spliced out of an RNA transcript of a nucleic acid sequence encoding an expression product via the UPR mechanism to regulate expression. The UPR mechanism is ubiquitous across eukaryotes, and the mechanism and relevant sequences are remarkably conserved. Thus, the invention can be practised across all eukaryotic cells. The regulatable intron is preferably capable of being spliced out by the IRE1 protein or a homologue or orthologue thereof (homologues or orthologues of IRE1 are present in all eukaryotes, including fungi, plants and mammals).

The promoter is typically heterologous to the nucleic acid sequence encoding the expression product. That is to say, the promoter is not naturally found operatively linked to sequence encoding the expression product. For example, the promoter and nucleic acid sequence encoding the expression product are typically not found together in a naturally occurring gene. In some embodiments of the invention the promoter is a synthetic promoter, i.e. a promoter that is not naturally occurring. There are a wide range on constitutive and non-constitutive promoters known in the art suitable for use in eukaryotic cells, and mention can be made of CAG promoter, CMV promoter, SV40 as non-limiting examples.

In preferred embodiments the expression product is a protein. In such embodiments the un-spliced transcript produced from the nucleic acid sequence encoding the expression product encodes a truncated or otherwise defective version of the protein as a result of the presence of the regulatable intron, but when the transcript is processed by the UPR mechanism in the cell the excisable sequence of the intron is spliced out and the functional protein can be produced from the transcript. Thus, splicing out of the regulatable intron results in a functional mRNA encoding the functional protein expression product.

However, in some cases the expression product can be a product other than a protein. Suitably the expression product can be an RNA molecule, for example ribozyme, RNA aptamer, siRNA, antisense RNA, or miRNA. In such embodiments a non-functional form of the RNA molecule is produced as the un-spliced transcript, and splicing out of the excisable portion of the intron converts the RNA molecule to an active form.

In preferred embodiments of the present invention, splicing out of the excisable sequence of the regulatable intron permits correct translation of the transcript from the nucleic acid sequence encoding the expression product, thereby allowing the desired expression product (e.g. protein) to be produced. In such embodiments the presence of the intron in the transcript from the nucleic acid sequence encoding the expression product results in a protein being translated from the transcript which is non-functional. Typically, this results either from the insertion in the translated protein of amino acids coded for by the intron, or, more preferably, as a result of introduction of a stop codon or frame shift (relative to the normal transcript coding for the functional protein) in the transcript 3' of the intron. The protein encoded by the un-spliced transcript can be non-functional for many reasons, for example:

The intron may result in a frame shift downstream (i.e. in a 3' direction) of the intron. This typically results when the excisable sequence of the intron is not a multiple of three nucleotides in length. Such a frame shift often results in introduction of a stop codon, resulting in a truncated protein. In other cases it can simply result in a complete alteration in the encoded amino acid sequence downstream of the intron.

Introduction of a coding sequence which results in amino acids being present in the translated protein which are disruptive to function of the protein. In this case the amino acid sequence downstream of the intron is not altered, but the amino acid sequence encoded by the intron, which in the un-spliced form will be present in the translated protein, disrupts the function of the protein.

Introduction of a stop codon in the intron sequence. In this case, the intron itself may comprise a stop codon, which will result in premature termination of translation, and the production of a truncated protein.

In certain preferred embodiments of the present invention the synthetic nucleic acid expression construct is configured such that splicing out of the excisable sequence of the intron eliminates a premature stop codon in the transcript. "Premature" in the present context means a stop codon which occurs upstream (i.e. in a 5' direction) of the stop codon in the normal transcript, i.e. the transcript encoding the functional protein (e.g. the wild type mRNA).

Preferably the regulatable intron is configured such that splicing out of the excisable sequence of the intron results in a shift of reading frame for sequences in the transcript located downstream (i.e. 3') of the regulatable intron.

In certain preferred embodiments of the present invention the regulatable intron is configured such that, when splicing occurs, a sequence having a length in nucleotides which is not a multiple of 3 is excised from the transcript. In other words, the excisable sequence has a length of n nucleotides, wherein n is not divisible by three.

In preferred embodiments of the present invention the regulatable intron comprises the sequence CNG/CNG-Xn-CNG/CNG, wherein Xn represents a sequence of length n bases, wherein/represents a cleavage site and wherein the sequence CNG-Xn-CNG is excised from the transcript.

Thus, in other words, the regulatable intron suitably comprises a central sequence (Xn) flanked by two splice site target sequences, each having the sequence CNG/CNG, wherein/represents a cleavage site.

CNG/CNG is a consensus splice site sequence targeted in a highly-conserved manner by the UPR system in eukaryotic cells. As is known in the art, this splice site consensus sequence is targeted by the IRE1 protein (homologues or orthologues of which are present in all eukaryotes, including fungi, plants and mammals) when the UPR response is induced. In nature, introns having this consensus splice site target sequence are found in the mRNA encoding transcription factors that are activated in the UPR, e.g. the XBP1 protein (in metazoa), the Hac1 protein (in yeast), and the bZIP60 protein (in plants). The endoribonuclease activity of IRE1 or homologues or orthologues thereof acts to cleave the RNA transcript at the position indicated by /, to remove the excisable intron sequence, and the cleaved RNA is then ligated together by an RNA ligase protein (RNA ligase RIg1p in *S. cerevisiae*, RNA ligase RtcB in mammalian cells). The UPR systems in mammalian, yeast and plant cells have been widely investigated, and the mechanisms are comparatively well-characterised (see, for example, Yoshida et al., Cell, Vol. 107, 881-891, Dec. 28, 2001; Lu, et al. *Mol Cell.* 2014 Sep. 4; 55(5): 758-770; Samali et al., International Journal of Cell Biology, Vol. 2010, Article ID 830307, 11 pages doi:10.1155/2010/830307; Chakraborty et al., Appl Biol Chem DOI, 10.1007/s13765-016-0167-6, Online ISSN 2468-0842, Print ISSN 2468-0834; and Nagashima et al., Scientific Reports 1, Article number: 29 (2011), DOI: 10.1038/srep00029). Accordingly, the mechanisms of the UPR will not be discussed in depth here. However, it is important to note that, in view of the high level of conservation of IRE1-mediated splicing, introns originating from one species can be successfully spliced by another species which is evolutionary highly diversified; for example, Yoshida et al. (id.) explains that mammalian cells can successfully splice out the intron from the yeast Hac1 mRNA (Hac1 corresponding to XBP1 in mammalian cells).

It should be noted that the length of the regulatable intron can vary considerably. For example, the XBP1 intron in mammals and plants is typically 26 nucleotides in length, though variants of 20 and 23 nucleotides have been observed. The Hac1 intron of yeast is considerably longer, typically in the order of 252 nucleotides in length (though, as mentioned above, this much longer Hac1 intron can still be spliced out in mammalian cells).

Accordingly, in various embodiments of the present invention the regulatable intron or Xn can be from 10 to 500 nucleotides in length, more preferably 15 to 350 nucleotides in length, yet more preferably 15 to 100 nucleotides in length, yet more preferably 15 to 35 nucleotides in length, and yet more preferably 20 to 25 nucleotides in length. The excisable sequence of the regulatory intron thus suitably has a length of 16 to 506 nucleotides, more preferably 21 to 356 nucleotides in length, yet more preferably 21 to 106 nucleotides in length, yet more preferably 21 to 41 nucleotides in length, and yet more preferably 26 to 31 nucleotides in length. As mentioned above, in some embodiments of the present invention it is preferred that the length Xn is selected such that the length of the excisable sequence is not divisible by 3.

There is considerable freedom regarding the specific sequence of Xn. Preferred sequences are set out below, but many other variants could of course be used provided that the regulatable intron remains functional, i.e. it is spliced out of the transcript by the UPR system at suitable levels. Of course, some possible sequences may be sub-optimal or interfere with the splicing process, e.g. as the result of the formation of undesirable secondary structures, but the person skilled in the art can readily assess the effect of any given sequence to determine whether it has any adverse effect on splicing.

Assessment of the functionality of a regulatable intron, i.e. its ability of the regulatable intron to be successfully spliced out of a transcript upon induction of the UPR, can readily be assessed by the skilled person using a wide range of approaches, and these can be tailored for the particular expression system in which the construct is intended to be used. As one preferred example, the methodology described in the examples below can be used, e.g. Example 1. For example, the functionality of any candidate regulatable intron to be assessed can be substituted into the construct described in Example 1 (referred to as SYNP-XBP-01) in place of the exemplary intron used in Example 1, and the ability of said intron to be successfully spliced out when the UPR is induced can be measured by assessing the level of EGFP expression before and after UPR induction by 2 mM DTT, exactly as carried out in Example 1. A functional regulatable intron is one which is able to be successfully spliced out after induction of the UPR to result in the expression of functional EGFP. Preferably a functional intron confers at least a 5-fold increase in expression 24 hours after induction of the UPR with 2 mM DTT, more preferably at least a 10-fold increase in expression, more preferably at least a 100-fold increase in expression, and yet more preferably at least a 1000-fold increase in expression of EGFP. It is preferred that before induction of the UPR the expression levels of EGFP are minimal, and preferably negligible. Minimal expression can be defined as, for example, less than 50% of the expression levels of a control construct as used in Example 1 (i.e. a construct without the regulatable intron in which expression of the sequence encoding the EGFP is driven by CMV-mp), preferably less than 20%, more preferably less than 10%, yet more preferably less than 5%, yet more preferably less than 1%. Negligible expression levels are those that are essentially undetectable using the methodology of Example 1.

However, it will be appreciated the skilled person could readily modify the approach taken in Example 1. For example, this might involve using different cell types, using a different expression product, using a different indicator of successful splicing (e.g. measuring levels of spliced mRNA encoding the functional expression product, or using a different reporter protein), and using a different inducer of the UPR. In such modified approaches, it remains the case that a functional regulatable intron is one which is able to be successfully spliced out after induction of the UPR to result in expression of a functional expression product after induction of the UPR. Preferably this results in at least a 5-fold increase in expression of the transcript encoding a functional expression product 24 hours after induction of the UPR, more preferably a 10-fold increase, more preferably a 100-fold increase, and yet more preferably at least a 1000-fold increase. It is preferred that before induction of the UPR the expression levels of the transcript encoding the functional expression product are minimal or negligible.

CNG/CNG[CG] is a preferred splice site consensus target sequence for mammalian cells, in which the presence of a C or G at the indicated location is preferred (though not required). The presence of a C at this location is typically preferred to a G. Accordingly, in some preferred embodiments of the invention, especially when the synthetic nucleic acid expression construct is intended for use in mammalian cells, the intron comprises the sequence CNG/CNG[CG] at one, other, or both (preferably both) ends of the intron.

Thus, in some preferred embodiments of the invention, the regulatable intron comprises the sequence CNG/CNG-Xn-CNG/CNG[CG], wherein Xn represents a sequence of length n nucleotides, wherein/represents the cleavage site such that the excisable sequence CNG-Xn-CNG is excised from the transcript upon splicing, and wherein the nucleotide at the 5' end of the sequence Xn is a C or G. Suitable lengths for Xn are set out above.

In some preferred embodiments of the invention Xn comprises the sequence CACUCAGACUACGUGCACCU (SEQ ID NO: 1) or a sequence which is at least 60% identical thereto, more preferably at least 70% identical thereto, yet more preferably at least 80% identical thereto, yet more preferably at least 90% identical thereto, and yet more preferably at least 95%, 96%, 97%, 98% or 99% identical thereto.

In some preferred embodiments of the invention Xn consists of the sequence CACUCAGACUACGUGCACCU (SEQ ID NO: 1) or a sequence which is at least 60% identical thereto, more preferably at least 70% identical thereto, yet more preferably at least 80% identical thereto, yet more preferably at least 90% identical thereto, and yet more preferably at least 95%, 96%, 97%, 98% or 99% identical thereto.

The sequence CACUCAGACUACGUGCACCU (SEQ ID NO: 1) corresponds to the region of the mammalian XBP1 intron lying inside of the IRE1 cleavage sites as set out above. Accordingly, this represents a preferred embodiment of the invention, particularly when the synthetic nucleic acid expression construct is intended for use in mammalian cells. However, sequences which are highly similar to this are also found across a range of non-mammalian XBP1 introns.

In some embodiments of the invention Xn comprises or consists of one of the following sequences:

```
                                      (SEQ ID NO: 1)
    CACUCAGACUACGUGCACCU;

(SEQ ID NO: 2)
    CACUCAGACUACGUGCUCCU;

(SEQ ID NO: 3)
    CACUCAGACUACGUGCCCCU;

(SEQ ID NO: 4)
    CACUCAGACUACGUGCGCCU;
    and (SEQ ID NO: 5)
    CACUCAGACUAUGUGCACCU.
```

In other embodiments of the invention Xn comprises or consists of the sequence ACGGGCAACUUUACACGACG (SEQ ID NO: 49) or a sequence which is at least 60% identical thereto, more preferably at least 70% identical thereto, yet more preferably at least 80% identical thereto, yet more preferably at least 90% identical thereto, and yet more preferably at least 95%, 96%, 97%, 98% or 99% identical thereto.

In a particularly preferred embodiment of the invention the regulatable intron comprises or consists of the sequence CNG/CNGCACUCAGACUACGUGCACCUCNG/CNGC (SEQ ID NO: 6), or a sequence which is at least 60% identical thereto, more preferably at least 70% identical thereto, yet more preferably at least 80% identical thereto, yet more preferably at least 90% identical thereto, and yet more preferably at least 95%, 96%, 97%, 98% or 99% identical thereto, wherein/represents a cleavage site. In variant sequences according to the above sequence identity levels, the splice site target sequence preferably remains as CNG/CNGC, and sequence variation occurs in the other regions.

Suitably the regulatable intron comprises or consists of the sequence CAG/CAGCACUCAGACUACGUGCAC-CUCUG/CUGC (SEQ ID NO: 7), or a sequence which is at least 60% identical thereto, more preferably at least 70% identical thereto, yet more preferably at least 80% identical thereto, yet more preferably at least 90% identical thereto, and yet more preferably at least 95%, 96%, 97%, 98% or 99% identical thereto, wherein/represents a cleavage site. In variant sequences according to the above sequence identity levels, the splice site target sequence preferably remains as CAG/CUGC, and sequence variation occurs in the other regions.

In some preferred embodiments of the invention the regulatable intron comprises or consists of one of the following sequences:

```
                                      (SEQ ID NO: 8)
    CNG/CAGCACUCAGACUACGUGCACCUCUG/CNG;

(SEQ ID NO: 9)
    CNG/CAGCACUCAGACUACGUGCUCCUCUG/CNG;

(SEQ ID NO: 10)
    CNG/CAGCACUCAGACUACGUGCCCCUCUG/CNG;

(SEQ ID NO: 11)
    CNG/CAGCACUCAGACUACGUGCGCCUCUG/CNG;
    and (SEQ ID NO: 12)
    CNG/CAGCACUCAGACUAUGUGCACCUCUG/CNG.
```

In further preferred embodiments of the invention the regulatable intron comprises or consists of one of the following sequences:

```
                                      (SEQ ID NO: 7)
    CAG/CAGCACUCAGACUACGUGCACCUCUG/CUGC;

(SEQ ID NO: 13)
    CAG/CAGCACUCAGACUACGUGCUCCUCUG/CUGC;

(SEQ ID NO: 14)
    CAG/CAGCACUCAGACUACGUGCCCCUCUG/CUGC;

(SEQ ID NO: 15)
    CAG/CAGCACUCAGACUACGUGCGCCUCUG/CUGC;
    and (SEQ ID NO: 16)
    CAG/CAGCACUCAGACUAUGUGCACCUCUG/CUGC.
```

In another embodiment of the invention the regulatable intron comprises the sequence CAG/CUGCAGCACUCA-GACUACGUGCACCUCUG/CAG (SEQ ID NO: 17) or CAG/CUGCAGCACUCAGACUACGUGCACCUCUG/ CUGG (SEQ ID NO: 27), wherein/represents a cleavage site. This sequence results from the addition of the trinucleotide CUG to the mammalian XBP1 intron sequence at the underlined position. Addition of this trinucleotide is believed to slightly de-optimise splicing of the intron to reduce any undesirable splicing (and hence background expression of the expression product) in cells.

Accordingly, in some preferred embodiments of the invention Xn comprises or consists of

```
                                      (SEQ ID NO: 23)
    CAGCACUCAGACUACGUGCACCU.
```

In another embodiment of the invention the regulatable intron comprises the sequence: CNG/CAGACGGGCAAC-UUUACACGACGCUG/CNG (SEQ ID NO: 50), or a sequence which is at least 60% identical thereto, more preferably at least 70% identical thereto, yet more preferably at least 80% identical thereto, yet more preferably at least 90% identical thereto, and yet more preferably at least 95%, 96%, 97%, 98% or 99% identical thereto, wherein/represents a cleavage site. In variant sequences according to the above sequence identity levels, the splice site target sequence preferably remains as CNG/CNG, and sequence variation occurs in the other regions.

For the avoidance of doubt, it is noted that in the intron sequences of the present invention, it is preferred that the splice site target sequences at each end of the intron are constrained as CNG/CNG, and more preferably as CNG/CNG[CG]. Thus, while some variation in the splice site target sequences is provided by these sequences, further variation, if required, should be accommodated by the central sequence lying between the two splice site target sequences.

In some preferred embodiments of the invention the regulatable intron is the XBP1 intron, the Hac1 intron, the bZIP60 intron, or a homologue thereof. By this it is meant that the intron can be a wild type form of the XBP1, Hac1 or bZIP60 intron, or a naturally occurring homologue thereof.

In some embodiments of the invention it may be preferable that the splice site target sequence (i.e. comprising the sequence CNG/CNG) in the transcript is flanked by sequences which are able to interact to form a stem-loop structure. Thus, the splice site target sequence is preferably flanked by sequences which are complementary to one another, such that they will hybridise with each other to form a stem-loop structure in which the splice site target sequence is located at least partially, preferably entirely, within the loop region of the stem-loop structure that is formed in the transcript.

With regard to the wild type XBP1, HAC1 and bZIP60 introns, it has been hypothesised that a stem loop structure is formed at the splice sites in the mRNA transcripts. This involves hybridisation between sequences in the intron and the exon adjacent to the splice site target sequence that are complementary in nucleotide sequence when read in opposite directions. The experiments reported herein show that splicing is successfully carried out when the intron is inserted into a coding sequence in a situation where such a stem loop structure is not expected to form. Thus, formation of a stem-loop structure does not appear to be necessary for successful splicing of the regulatable intron of the present invention. Nevertheless, in some cases it may be desirable that a stem-loop structure is formed as this may, for example, result in optimal splicing activity. In the alternative, it may in some cases be desirable to avoid providing a sequence which is amendable to forming a stem-loop structure, as that may lead to undesirably active splicing of the intron, thus potentially leading to expression leakage.

In certain embodiments of the present invention, where a stem-loop structure is to be formed, the stem-loop structure formed by the transcript preferably comprises a loop which comprises from 6 to 9 nucleotides, and a stem which is from 3 to 10 nucleotides in length. More preferably the stem-loop structure comprises a loop which comprises from 7 to 8 nucleotides, and a stem which is from 4 to 8 nucleotides in length.

In certain embodiments of the present invention, where a stem-loop structure is to be formed, the intron may suitably comprise a sequence at the splice target site as follows:

-Yn-CNG/CNG-A-Zn-
    wherein A is an sequence having a length of from 0 to 3
        nucleotides (preferably 1 or 2 nucleotides),
    wherein/represents the cleavage site,
    and wherein Yn and Zn represent sequences that are
        complementary in nucleotide sequence when read in
        opposite directions, and are thus are able to hybridise to
        form the stem of the stem-loop structure. Yn and Zn are preferably from 3 to 10 nucleotides in length, more preferably from 4 to 8 nucleotides in length.

In some embodiments the intron may suitably comprise a sequence at the splice target site as follows:

-Zn-CNG/CNG[CG]-A-Yn-, where the components have the same meaning as above. In this case A preferably has a length of 0, 1 or 2 nucleotides.

It will be apparent that providing suitable complementary sequences (e.g. Yn and Zn in the structures above) to provide the stem structure can be achieved by adapting the sequence of the intron to provide a suitable region which is complementary to the corresponding sequence in the adjacent coding (i.e. exon) sequence. It may also be possible or desirable to alter the sequence of the coding region to some extent, e.g. by utilising redundancy in the genetic code to alter the nucleic acid sequence without affecting the encoded amino acid sequence; typically an alteration in amino acid sequence of the expression product should be avoided.

In some embodiments of the invention the nucleic acid expression construct comprises an inducible promoter operably linked to the nucleic acid sequence encoding the expression product comprising a sequence which encodes a regulatable intron. As mentioned above, inducible promoters are known in the art. By combining an inducible promoter and the regulatable intron of the present invention, a dual level of expression can be achieved, i.e. control at both the transcription level and at the translation level. This can allow for very tight control of expression, e.g. to avoid any expression "leakage". This can be important, for example, during the expression of toxic proteins, or in any case where the amount of background expression has to be kept to an absolute minimum prior to induction of expression at the desired time.

In a preferred embodiment the inducible promoter is an unfolded protein response (UPR) inducible promoter, i.e. a promoter which itself is induced by the UPR. In such an embodiment induction of the UPR serves to both induce expression in terms of driving transcription and in permitting expression of a functional expression product as a result of splicing of the regulatable intron.

In embodiments of the present invention, the UPR inducible promoter suitably comprises at least one binding site for ATF6, XBP1, bZIP60, or homologous or otherwise equivalent transcription factors, which drive protein expression in the UPR.

Suitably the UPR inducible promoter comprises one or more copies of the at least one of the following sequences:

```
TGACGTG (the ATF6 consensus sequence),

TGACGTGCT (a variant of the above),

TGACGTG[TG] (known as the UPRE site), (SEQ ID NO: 18)
CCAAT-N9-CCACG (known as the ERSE1 site),
and (SEQ ID NO: 19)
ATTGG-N-CCACG (known as the ERSE2 site).
```

These sites are bound by ATF6, XBP1 and bZIP60.

Suitably the promoter comprises one or more copies of the sequence TGACGTG (optionally as part of TGACGTGCT or TGACGTG[TG]), preferably 3 or more copies of the sequence TGACGTG[TG] (optionally as part of TGACGTGCT or TGACGTG[TG]), and preferably 5 or more copies of the sequence TGACGTG[TG] (optionally as part of TGACGTGCT or TGACGTG[TG]).

An exemplary UPR inducible promoter sequence comprises the following sequence

```
(SEQ ID NO: 20):
TGACGTGCTTGACGTGCTTGACGTGCTTGACGTGCTTGACGTGCTTGACG

TGCT.
```

This sequence comprises 6 tandem copies of the UPRE site.

Another exemplary UPR inducible promoter sequence comprises the following sequence

```
(SEQ ID NO: 47):
TGACGTGCTGATGATGCGTAGCTAGTAGTTGACGTGCTGATGATCGCCGT

ACGCTACGTAGTTGACGTGCTGATGATGCGTAGCTAGTAGTTGACGTGCT

GATGATCGCCGTAGCTACGTAGTTGACGTGCTGATCGATGCGTAGCTAGT

AGTTGACGTGCT.
```

This sequence comprises 6 copies of the UPRE site, each spaced by 20 nucleotides.

Suitably the UPR inducible promoter comprises said at least one binding site for ATF6, XBP1 or homologous or otherwise equivalent transcription factors which drive the UPR operatively linked to a minimal promoter sequence (e.g. the CMV-minimal promoter). Other suitable minimal promoters are known in the art.

The CMV-minimal promoter has the following sequence

```
(SEQ ID NO: 21):
AGGTCTATATAAGCAGAGCTCGTTTAGTGAACCGTCAGATCGCCTAGATA

CGCCATCCACGCTGTTTTGACCTCCATAGAAGAT
```

An exemplary inducible promoter thus comprises a nucleic acid comprising a sequence according to SEQ ID NO: 20 positioned upstream of, and operatively linked to, a nucleic acid having a sequence according to SEQ ID NO: 21.

For example, the inducible promoter can suitably comprise the following sequence

```
(SEQ ID NO: 22):
TGACGTGCTTGACGTGCTTGACGTGCTTGACGTGCTTGACGTGCTTGACG

TGCTGGTACCGTCGACGATATCGGATCCAGGTCTATATAAGCAGAGCTCG

TTTAGTGAACCGTCAGATCGCCTAGATACGCCATCCACGCTGTTTTGACC

TCCATAGAAGATCGCCACC
```

Further details of UPR-inducible promoters that can be used in conjunction with the regulatable intron are provided below.

The nucleic acid sequence encoding an expression product is suitably a transgene. The transgene typically encodes a gene expression product such as RNA or a polypeptide (protein). The transgene may be a full-length cDNA or genomic DNA sequence, or any fragment, subunit or mutant thereof that has at least some biological activity. The transgene may suitably be a minigene, i.e. a gene sequence lacking part, most or all of its native intronic sequences. The transgene optionally may comprise conventional intron sequences (i.e. in addition to the regulatable intron). Optionally, the transgene may be a hybrid nucleic acid sequence, i.e., one constructed from homologous and/or heterologous cDNA and/or genomic DNA fragments. By 'mutant' is meant a nucleic acid sequence that contains one or more nucleotides that are different from the wild-type or naturally occurring sequence, i.e., the mutant nucleic acid sequence contains one or more nucleotide substitutions, deletions, and/or insertions. The nucleotide substitution, deletion, and/or insertion can give rise to a gene product (i.e., protein or nucleic acid) that is different in its amino acid/nucleic acid sequence from the wild type amino acid/nucleic acid sequence. In some cases, the transgene may also include a sequence encoding a leader peptide or signal sequence such that the transgene product will be secreted from the cell.

A conventional (i.e. non-regulatable) intron can be utilized in the nucleic acid sequence encoding an expression product in addition to the regulatable intron discussed above. The term "conventional intron" encompasses any portion of a whole intron that is large enough to be recognized and spliced by the nuclear splicing apparatus. Typically, short, functional, intron sequences are preferred in order to keep the size of the expression cassette as small as possible, which facilitates the construction and manipulation of the expression cassette. In some embodiments, the intron is obtained from a gene that encodes the protein that is encoded by the nucleic acid sequence encoding an expression product. The conventional intron can be located 5' to the sequence encoding an expression, 3' to the sequence encoding an expression, or within the sequence encoding an expression. Thus, in some embodiments, the nucleic acid sequence encoding an expression product further comprises a conventional intron. Non-limiting examples of suitable introns are Minute Virus of Mice (MVM) intron, beta-globin intron (betaIVS-II), factor IX (FIX) intron A, Simian virus 40 (SV40) small-t intron, and beta-actin intron. Introns can have benefits in terms of improved expression levels, as is well-known in the art.

In some preferred embodiments of the present invention the nucleic acid sequence encoding an expression product encodes a protein. Essentially any protein can be used, and by way of non-limiting example the protein can be an enzyme, an antibody or antibody fragment (e.g. a monoclonal antibody), a viral protein (e.g. REP-CAP, REV, VSV-G, or RD114), a therapeutic protein, or a toxic protein (e.g. Caspase 3, 8 or 9).

In some preferred embodiments of the present invention the nucleic acid sequence encoding an expression product encodes a toxic protein. A "toxic protein" in this case means a protein that is toxic to the cells in which the expression product are, in use, produced. For example, the toxic protein might be one of the following: Caspase 3, caspase 8, caspase 9, and a toxic viral protein (such as VSV-G or the AAV REP protein).

In some preferred embodiments of the present invention the nucleic acid sequence encoding an expression product encodes a therapeutic expression product. The therapeutic expression product can be a protein, e.g. a secretable protein such as, e.g., a clotting factor, e.g., factor IX or factor VIII, a cytokine, a growth factor, an antibody or nanobody, a chemokine, a plasma factor, insulin, erythropoietin, lipoprotein lipase, or a toxic protein.

Alternatively, the therapeutic expression product may be RNA, such as siRNA or miRNA. Various therapeutic siRNAs have been described in the art, and, by way of non-limiting example, the siRNA may be on that is intended to treat to treat FTDP-17 (frontotemporal dementia), DYT1 dystonia, growth hormone deficiency, BACE1 in Alzheimer's, Leukaemia (e.g. targeting c-raf, bcl-2), melanoma (e.g. targeting ATF2, BRAF), prostate cancer (e.g. targeting P110B), and pancreatic carcinoma (e.g. targeting K-Ras). SiRNA therapies are summarised in "Therapeutic potentials of short interfering RNAs", Appl Microbiol Biotechnol, DOI 10.1007/s00253-017-8433-z. Similarly, for miRNA, various miRNA therapeutic approaches that could be implemented according to the present invention are summarised in "MicroRNA therapeutics: towards a new era for the management of cancer and other diseases", Nature Reviews Drug Discovery; 16, 203-222 (2017).

Suitably the nucleic acid expression construct comprises sequences providing or coding for one or more of, and preferably all of, a ribosomal binding site, a start codon, a stop codon, and a transcription termination sequence.

In a further aspect the present invention provides a nucleic acid comprising a sequence encoding an expression product (e.g. a gene), the sequence encoding an expression product comprising a sequence which encodes a regulatable intron, said regulatable intron being an intron which comprises an excisable sequence which is capable of being spliced out of a transcript produced from the synthetic expression construct via the unfolded protein response (UPR) system in the cell, thereby resulting in a transcript encoding a functional expression product, and wherein the expression product is not the XBP1 protein, Hac1 protein, bZIP60 protein or a homologue thereof.

Accordingly, the sequence encoding an expression product is not a gene which naturally contains a regulatable intron according to the present invention. In other words, the regulatable intron is heterologous to the sequence encoding an expression product in which it is found.

Preferred features of the regulatable intron and the sequence encoding an expression product are as set out above.

Such a nucleic acid can be inserted into any suitable expression construct, e.g. an expression vector such that is operatively linked to a promoter and any other elements required to drive transcription of the nucleic acid. Expression of the functional expression product will be controlled by the regulatable intron.

In a further aspect, the invention provides a vector comprising a synthetic nucleic acid expression construct as set out above.

The term "vector" is well known in the art, and as used in the application refers to nucleic acid molecules, e.g. double-stranded DNA, which may have inserted into it a nucleic acid expression construct according to the present invention. A vector is suitably used to transport an inserted nucleic acid molecule into a suitable host cell. A vector typically contains all of the necessary elements that permit transcribing the insert nucleic acid molecule, and, preferably, translating the transcript into a polypeptide. A vector typically contains all of the necessary elements such that, once the vector is in a host cell, the vector can replicate independently of, or coincidental with, the host chromosomal DNA; several copies of the vector and its inserted nucleic acid molecule may be generated. Vectors of the present invention can be episomal vectors (i.e., that do not integrate into the genome of a host cell), or can be vectors that integrate into the host cell genome. This definition includes both non-viral and viral vectors. Non-viral vectors include but are not limited to plasmid vectors (e.g. pMA-RQ, pUC vectors, bluescript vectors (pBS) and pBR322 or derivatives thereof that are devoid of bacterial sequences (minicircles)) transposons-based vectors (e.g. PiggyBac (PB) vectors or Sleeping Beauty (SB) vectors), etc. Larger vectors such as artificial chromosomes (bacteria (BAC), yeast (YAC), or human (HAC)) may be used to accommodate larger inserts. Viral vectors are derived from viruses and include but are not limited to retroviral, lentiviral, adeno-associated viral, adenoviral, herpes viral, hepatitis viral vectors or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis. Virosomes are a non-limiting example of a vector that comprises both viral and non-viral elements, in particular they combine liposomes with an inactivated HIV or influenza virus (Yamada et al., 2003). Another example encompasses viral vectors mixed with cationic lipids.

In some preferred embodiments, the vector is a viral vector, such as a retroviral, lentiviral, adenoviral, or adeno-associated viral (AAV) vector, more preferably an AAV vector. AAV vectors are preferably used as self-complementary, double-stranded AAV vectors (scAAV) in order to overcome one of the limiting steps in AAV transduction (i.e. single-stranded to double-stranded AAV conversion) (Mc-Carty, 2001, 2003; Nathwani et al., 2002, 2006, 2011; Wu et al., 2008), although the use of single-stranded AAV vectors (ssAAV) are also encompassed herein.

In some preferred embodiments, the vector is a plasmid. Such a plasmid may include a variety of other functional nucleic acid sequences, such as one or more selectable markers, one or more origins of replication, polycloning sites and the like.

In some preferred embodiments of the invention the vector is an expression vector for expression in eukaryotic cells. Examples of eukaryotic expression vectors include, but are not limited to, pW-LNEO, pSV2CAT, pOG44, pXTI and pSG available from Stratagene; pSVK3, pBPV, pMSG and pSVL available from Amersham Pharmacia Biotech; and pCMVDsRed2-express, pIRES2-DsRed2, pDsRed2-Mito, pCMV-EGFP available from Clontech. Many other vectors are well-known and commercially available. For mammalian cells adenoviral vectors, the pSV and the pCMV series of vectors are particularly well-known non-limiting examples. There are many well-known yeast expression vectors including, without limitation, yeast integrative plasmids (Ylp) and yeast replicative plasmids (YRp). For plants the Ti plasmid of *agrobacterium* is an exemplary expression vector, and plant viruses also provide suitable expression vectors, e.g. tobacco mosaic virus (TMV), potato virus X, and cowpea mosaic virus.

In some preferred embodiments the vector is a gene therapy vector. Various gene therapy vectors are known in the art, and mention can be made of AAV vectors, adenoviral vectors, retroviral vectors and lentiviral vectors. Where the vector is a gene therapy vector the nucleic acid, sequence encoding an expression product suitably encodes a therapeutic protein. The therapeutic protein may be a secretable protein. Non-limiting examples of secretable proteins, in particular secretable therapeutic proteins, include clotting factors, such as factor VII I or factor IX, insulin, erythropoietin, lipoprotein lipase, antibodies or nanobodies, growth factors, cytokines, chemokines, plasma factors, toxic proteins, etc.

The nucleic acid expression construct and vectors of the present invention may be formulated in a pharmaceutical composition with a pharmaceutically acceptable excipient, i.e., one or more pharmaceutically acceptable carrier substances and/or additives, e.g., buffers, carriers, excipients, stabilisers, etc. The pharmaceutical composition may be provided in the form of a kit. The term "pharmaceutically acceptable" as used herein is consistent with the art and means compatible with the other ingredients of the pharmaceutical composition and not deleterious to the recipient thereof.

Accordingly, a further aspect of the invention provides a pharmaceutical composition comprising a nucleic acid expression construct or a vector described herein.

In a further aspect of the invention there is provided the use of nucleic acid expression constructs and vectors according to various aspects of the present invention for the manufacture of a pharmaceutical composition.

According to a further aspect of the present invention there is provided a cell comprising a synthetic nucleic acid expression construct or vector according to the present invention.

Preferably the cell is a eukaryotic cell. The eukaryotic cell can suitably be a fungal cell (e.g. yeast cell), an animal (metazoan) cell (e.g. mammalian cells), or a plant cell.

In some embodiments of the invention the cell may be a prokaryotic cell; although prokaryotic cells do not possess the UPR, prokaryotic cells may nonetheless be useful in production of the synthetic nucleic acid expression construct or other steps in handling the synthetic nucleic acid expression construct.

In some preferred embodiments of the invention the cell is ex vivo, e.g. in cell culture. In other embodiments of the invention the cell may be part of a tissue or multicellular organism.

In some preferred embodiments, the expression product is toxic to the cell in which the construct or vector is present. In one such embodiment, the cell is a cell for use in cell therapy (e.g. a therapeutic immune cell, such as a therapeutic T cell) which comprises a synthetic nucleic acid expression construct of vector according to the present invention, wherein the expression product is toxic to the cell. In such an embodiment induction of the UPR can be sued to induce death of the cell, i.e. as a kill switch. Suitable toxic expression products include caspases, e.g. caspase 3, caspase 8, or caspase 9.

The synthetic nucleic acid expression construct may be inserted into the genome of the cell, or may be present in an episomal vector.

In a further aspect the present invention provides a method for producing an expression product, the method comprising:

a) providing a population of eukaryotic cells comprising a synthetic nucleic acid expression construct according to the present invention;

b) treating said population of cells so as to induce the unfolded protein response, thereby inducing splicing of the excisable sequence out of the regulatable intron;

c) incubating said population of cells under suitable conditions for production of the expression product; and d) isolating the expression product from said population of cells.

The method is suitable a cell culture method. The cells may therefore be provided under suitable cell culture condition for the cell type being used. Suitable cell culture conditions are well known to the skilled person.

The synthetic nucleic acid expression construct can be present in the genome or can be episomal.

It will be apparent the present invention allows for the production of the expression product (or the active form of the expression product) to be delayed until a desired point in a cell culture process. This can, for example, permit the population of cells to be expanded until such time as a desired cell number or concentration is reached, or a desired growth phase is reached.

For example, in the case of toxic proteins, the production of a functional (i.e. toxic) expression product can be avoided until a cell culture system is at a desired stage. Once the toxic protein is expressed the cells will of course be adversely affected or killed.

The method suitably comprises incubating said population of cells under conditions suitable for growth of the cells prior to step b) of treating said population of cells so as to induce the unfolded protein response (UPR).

Typically step b) comprises applying a stress to said cells, said stress being suitable to induce the UPR. There is a wide range of stresses that can be used to induce the UPR, and they are described extensively in the literature.

In some preferred embodiments the step of inducing the UPR suitably comprises administering a chemical agent that is able to induce the UPR in said cells (i.e. a UPR-inducing chemical agent).

The person skilled in the art can readily assess the ability of any particular stress (e.g. a chemical agent) to induce the UPR. For example, the person skilled in the art can suitably apply the stress (e.g. by administering a candidate chemical agent) in the method of Example 1 in place of DTT. The ability of the agent to induce the UPR will be identified by the effect that the application of stress (e.g. the chemical agent) has upon the expression of the functional expression product, i.e. EGFP in the case of Example 1. Of course, the method of example 1 can be modified as required, e.g. using a different cell type or a different construct. Example 4, in particular, demonstrates how various candidate chemical agents can be tested for their ability to induce the UPR. Various other methods to assess the ability of a stress (e.g. a chemical agent) to induce the UPR will be apparent to the skilled person.

Many chemical agents that can induce ER stress and induce the UPR are known in the art. UPR-inducing chemical agents that are able to induce the IRE1 pathway are suitable for use in the present invention as they will lead to splicing of the regulatable intron.

Exemplary UPR-inducing chemical agents that can be used to induce the UPR include:

Dithiothreitol (DTT)—this agent reduces the disulfide bridges of proteins. The denatured proteins accumulated inside the ER.

Tunicamycin—this agent inhibits N-linked glycosylation.

Brefeldin A—this is a commonly used as an inducer of the unfolded protein response.

Thapsigargin—this agent leads to ER $Ca^{2+}$ depletion due to inhibition of the Sarco/Endoplasmic Reticulum $Ca^{2+}$-ATPase (SERCA).

2-deoxyglucose

A23187 (CAS Number 52665-69-7)

Bortezomib (Velcade)

Quercetin

Agents that disrupts the lipid balance in the cells such that UPR is induced, e.g. saturated fatty acids (e.g. palmitic acid)—i.e. those agents that induce lipid-induced ER stress response/UPR.

Such UPR-inducing chemical agents can be administered at suitable concentrations, and such concentrations can readily be determined by the skilled person though routine experimentation and consultation of the literature. Suitable concentrations for administration of the various agents are as follows: DTT 2 mM; Tunicamycin 2.5-5 µg/ml; Brefeldin A 0.5 µg/ml; Thapsigargin 0.1-1 µM; 2-deoxyglucose 4 mM; A23187 (CAS Number 52665-69-7) 0.5 µM; Bortezomib (Velcade) 5-30 nM; and palmitic acid (or other fatty acids) 100 µM. These concentrations refer to the concentration of the agent in the medium to which the cells are exposed.

Another UPR-inducing chemical agents for use in the present invention is forskolin. Forskolin (coleonol) is a labdane diterpene that is produced by the Indian *Coleus* plant (*Plectranthus barbatus*). Other names for forskolin include pashanabhedi, Indian *coleus*, makandi, HL-362, and NKH477.

Dithiothreitol (DTT), tunicamycin and thapsigargin are used extensively in the literature to induce the UPR, and thus represent preferred UPR-inducing chemical agents in some embodiments of the invention. Forskolin is another preferred UPR-inducing chemical agent, particularly but not exclusively in view of its safety profile for use in vivo.

In a particularly preferred embodiment of the present invention, an UPR-inducing chemical agent that is able to disrupt the lipid balance in said cells is administered in order to induce the UPR. The role of lipids and lipid metabolism in inducing the UPR has been extensively reported in the literature, and the phenomenon is termed "lipid-induced ER stress response/UPR". See, for example, lwao and Shidoj, PLOS ONE|DOI:10.1371/journal.pone.0132761 Jul. 17, 2015; Robblee et al. "Saturated Fatty Acids Engage an IRE1a-Dependent Pathway to Activate the NLRP3 Inflammasome in Myeloid Cells"—Cell Reports 14, 2611-2623, Mar. 22, 2016; Ariyama et al., "Decrease in Membrane Phospholipid Unsaturation Induces Unfolded Protein Response"—THE JOURNAL OF BIOLOGICAL CHEMISTRY VOL. 285, NO. 29, pp. 22027-22035, Jul. 16, 2010; Basseri and Austin "Endoplasmic Reticulum Stress and Lipid Metabolism: Mechanisms and Therapeutic Potential"—Biochemistry Research International Volume 2012, Article ID 841362, 13 pages, doi:10.1155/2012/841362; Kitai et al. "Membrane lipid saturation activates IRE1a without inducing clustering"—Genes to Cells (2013) 18, 798-809. Accordingly, suitably the UPR-inducing chemical agent is able to alter the lipid balance of the cells in such a way that UPR is induced. There are a wide range of agents that can achieve this. For example, it has been shown that disruption of the lipid balance in cells in such a way that lipid saturation levels are increased (and thus desaturated lipid levels are decreased) results in induction of the UPR. Accordingly, suitably the UPR-inducing chemical agent is able to alter the lipid balance of the cells in such a way that lipid saturation levels are increased.

Preferably the UPR-inducing chemical agent is able to alter the ratio of saturated fatty acids to unsaturated fatty acids in cell membranes such that the proportion of saturated fatty acids is increased. This can be achieved in several ways, e.g. introducing saturated fatty acids to the cells or inhibiting the activity of enzymes which convert saturated fatty acids to unsaturated fatty acids.

Thus, in one particularly preferred embodiment the UPR-inducing chemical agent comprises a saturated fatty acid, suitably a medium or long chain saturated fatty acid. In certain embodiments of the invention the fatty acid has an aliphatic chain length of from 6 to 26 carbons, more preferably from 9 to 22 carbons, yet more preferably from 12 to 20 carbons, and yet more preferably from 14 to 20 carbons.

Suitably the UPR-inducing chemical agent comprises at least one fatty acid selected from the list consisting of: Caproic acid, Enanthic acid, Caprylic acid, Pelargonic acid, Capric acid, Undecylic acid, Lauric acid, Tridecylic acid, Myristic acid, Pentadecylic acid, Palmitic acid, Margaric acid, Stearic acid, Nonadecylic acid, Arachidic acid, Heneicosylic acid, Behenic acid, Tricosylic acid, Lignoceric acid, Pentacosylic acid, and Cerotic acid. More preferably the UPR-inducing chemical agent comprises at least one fatty acid selected from the list consisting of: Pelargonic acid, Capric acid, Undecylic acid, Lauric acid, Tridecylic acid, Myristic acid, Pentadecylic acid, Palmitic acid, Margaric acid, Stearic acid, Nonadecylic acid, Arachidic acid, Heneicosylic acid, and Behenic acid. Yet more preferably the UPR-inducing chemical agent comprises at least one fatty acid selected from the list consisting of: Lauric acid, Tridecylic acid, Myristic acid, Pentadecylic acid, Palmitic acid, Margaric acid, Stearic acid, Nonadecylic acid and Arachidic acid. Yet more preferably the UPR-inducing chemical agent comprises at least one fatty acid selected from the list consisting of: Myristic acid, Pentadecylic acid, Palmitic acid, Margaric acid, Stearic acid, Nonadecylic acid and Arachidic acid.

In a particularly preferred embodiment the UPR-inducing chemical agent comprises palmitic acid or stearic acid.

It should be noted that where fatty acids are referred to, these can be provided in any suitable form, e.g. as a salt (palmitate, stearate or suchlike).

In another preferred embodiment, the UPR-inducing chemical agent comprises an agent that is able to downregulate stearoyl-CoA desaturase enzyme activity in the cell. Stearoyl-CoA desaturase is an ER resident enzyme which introduces a double-bond in saturated fatty acids. For example, the UPR-inducing chemical agent suitably comprises an inhibitor of stearoyl-CoA desaturase. MF-43 is an example of a suitable inhibitor of Stearoyl-CoA desaturase. Alternatively, the UPR-inducing chemical agent may be able to downregulate expression of stearoyl-CoA desaturase, e.g. through knockdown of stearoyl-CoA desaturase expression (e.g. via RNA interference), or knockout of the stearoyl-CoA desaturase gene. Other genes involved in desaturation of fatty acids can also be targeted.

Other exemplary UPR-inducing chemical agents include geranylgeranoic acid (GGA), 2,3-dihydro GGA, 9-cis retinoic acid and all-trans retinoic acid (see—Chieko lwao and Yoshihiro Shidoj, PLOS ONE|DOI:10.1371/journal.pone.0132761 Jul. 17, 2015).

Combinations of several UPR-inducing chemical agents can be used in some embodiments of the invention. For example, a saturated fatty acid (e.g. palmitic acid) can be used in combination with an agent that is able to downregulate stearoyl-CoA desaturase enzyme activity (e.g. MF-43).

In another embodiment of the present invention, inducing the UPR in step b) suitably comprises expressing an inducer protein in said population of eukaryotic cells so as to induce the UPR response in the population of cells. Such a protein is referred to as an "inducer protein" as when it is expressed in the population of cells it acts to induce the UPR response, typically by creating ER stress. The inducer protein is typically a different protein to that encoded by the synthetic nucleic acid expression construct according to the first aspect of the invention. The inducer protein is suitably a heterologous protein, but in some embodiments it could be a homologous protein that is overexpressed. What matters is that expression of the inducer protein in the cells induces the UPR, which results in splicing of the regulatable intron. There are many ways in which expression of an inducer protein can be achieved in the population of cells. In suitable embodiments, the population of cells is transfected with an expression vectors that is adapted to express the inducer protein in the cells. In one embodiment, the cells can be infected with a virus which results in expression of viral proteins that lead to ER stress and induction of the UPR. A recombinant viral vector encoding viral or non-viral proteins could also be used, and an example is described below in which AAV is expressed in the cells to induce the UPR; this forms one preferred embodiment of the present invention. Alternatively, essentially any other form of expression vector (e.g. a plasmid) could be introduced into the cells in order to express a heterologous protein. Suitable methods of transfecting cells in with suitable expression vectors are well-known in the art. The nature of the inducer protein is typically not of particular concern, though it is generally preferable that the protein is non-toxic; rather, it is the ER-stress that heterologous protein production creates in the cell that is of consequence.

In some embodiments step b) comprises transfecting said population of cells with an expression vector that is capable of expressing an inducer protein, preferably a heterologous protein, in said cells. Alternatively, step b) can comprise inducing expression of the inducer protein from an expression vector that was previously introduced into the cells, e.g. prior to step a).

Expression of the inducer protein can be under control of a constitutive or non-constitutive promoter. An exemplary non-constitutive promoter is an inducible promoter (in this case the inducible promoter would not be a UPR-inducible promoter).

Other methods of inducing the unfolded protein response comprise exposing the cells to hypoxia, or carbohydrate (e.g. glucose) deprivation.

As mentioned above, in view of the ubiquitous nature of IRE1-mediated intron slicing across the eukaryotes, the method can be performed with any type of eukaryotic cell. Accordingly the method can be carried out, for example, in fungal cells (e.g. yeast cells), animal (metazoan) cells (e.g. mammalian cells), and plant cells.

In certain preferred embodiments, the population of eukaryotic cells is a population of animal (metazoan) cells. Suitably the animal cells can be cells from an invertebrate animal or a vertebrate animal.

In some preferred embodiments, the population of eukaryotic cells is a population of mammalian cells. There a wide range of mammalian cells that can be used, including without limitation Chinese hamster ovary (CHO), human embryonic kidney (HEK) cells (e.g. HEK-293), human embryonic retinal cells, human amniocyte cells, Mouse myeloma lymphoblstoid cells. In such embodiments, it may be preferred that the regulatable intron is an intron which comprises the sequence CNG/CNG[CG] at one, other, or both (preferably both) ends of the intron, i.e. the mammalian splice target consensus sequence. Suitably, for example, the regulatable intron has the sequence

```
                              (SEQ ID NO: 6)
CNG/CNGCACUCAGACUACGUGCACCUCNG/CNGC, (SEQ ID NO: 7)
CAG/CAGCACUCAGACUACGUGCACCUCUG/CUGC or (SEQ ID NO: 17)
CAG/CUGCAGCACUCAGACUACGUGCACCUCUG/CUGC.
```

In other embodiments, the population of eukaryotic cells is a population of insect cells. Suitable insect cells for use in the method include baculovirus infected and non-infected cell, such as cells from the following insect species: *Spo-* doptera frugiperda (e.g. Sf9 or Sf21), *Trichoplusia ni* (e.g. Hi-5), *Drosophila melanogaster* (e.g. Schneider 2 cells and Schneider 3 cells).

In other embodiments of the present invention the population of eukaryotic cells is suitably a population of fungal cells, preferably yeast cells. Suitable fungal cells for use in the present method include without limitation *Saccharomyces cerevisiae, Pichia pastoris, Aspergillus* spp., *Trichoderma* spp. and *Myceliophthora thermophila.*

In other embodiments of the present invention, the population of eukaryotic cells is suitably a population of plant cells or plant protoplasts.

In other embodiments of the present invention the population of eukaryotic cells is suitably a population of protozoan cells, e.g. *Leishmania tarentolae.*

Step d), i.e. isolating the expression product from said population of cells, can be carried out using conventional techniques well-known in the art. Such techniques will of course vary depending on the nature of the expression product.

The method may suitably comprise the step of introducing the nucleic acid expression construct into the cells. There are many well-known methods of transfecting eukaryotic cells, and the skilled person could readily select a suitable method for any cell type. The nucleic acid expression construct can of course be provided in any suitable vector.

In a further aspect, the invention provides the nucleic acid expression constructs, vectors, cells or pharmaceutical compositions according to the various aspects of the present invention for use in a method of treatment or therapy.

As used herein, the terms "treat" or "treatment" refer to both therapeutic treatment and prophylactic or preventative measures. Beneficial or desired clinical results include, but are not limited to, prevention of an undesired clinical state or disorder, reducing the incidence of a disorder, alleviation of symptoms associated with a disorder, diminishment of extent of a disorder, stabilized (i.e., not worsening) state of a disorder, delay or slowing of progression of a disorder, amelioration or palliation of the state of a disorder, remission (whether partial or total), whether detectable or undetectable, or combinations thereof. "Treatment" can also mean prolonging survival as compared to expected survival if not receiving treatment.

As used herein, the terms "therapeutic treatment" or "therapy" and the like, refer to treatments wherein he object is to bring a subject's body or an element thereof from an undesired physiological change or disorder to a desired state, such as a less severe or unpleasant state (e.g., amelioration or palliation), or back to its normal, healthy state (e.g., restoring the health, the physical integrity and the physical well-being of a subject), to keep it at said undesired physiological change or disorder (e.g., stabilization, or not worsening), or to prevent or slow down progression to a more severe or worse state compared to said undesired physiological change or disorder.

As used herein the terms "prevention", "preventive treatment" or "prophylactic treatment" and the like encompass preventing the onset of a disease or disorder, including reducing the severity of a disease or disorder or symptoms associated therewith prior to affliction with said disease or disorder. Such prevention or reduction prior to affliction refers to administration of the nucleic acid expression constructs, vectors, or pharmaceutical compositions described herein to a patient that is not at the time of administration afflicted with clear symptoms of the disease or disorder. "Preventing" also encompasses preventing the recurrence or relapse-prevention of a disease or disorder for instance after a period of improvement. In embodiments, the nucleic acid expression constructs, vectors, or pharmaceutical compositions described herein may be for use in gene therapy.

The present invention also provides the use of the nucleic acid expression constructs, the vectors, or the pharmaceutical compositions described herein for the manufacture of a medicament for gene therapy.

Also disclosed herein is a method for gene therapy in a subject in need of said gene therapy comprising:

> introducing into the subject a gene therapy vector comprising a pharmaceutical composition comprising a nucleic acid expression construct according to the present invention, the nucleic acid expression construct comprising a sequence encoding a therapeutic expression product such that the gene therapy vector delivers the nucleic acid expression construct to target cells of the subject; and
>
> expressing a therapeutically effective amount of the functional therapeutic expression product in target cells of subject.

It will be apparent that the expression of a therapeutically effective amount of the functional therapeutic expression product will only occur when the expression product is expressed in a cell where the UPR is active. In many cases the UPR will be active in cells which are under stress, e.g. cells which are cancerous or which are infected with a pathogen (e.g. a virus). Accordingly, it is an advantage of the present invention that expression of the functional therapeutic product (which could be, for example, a toxic protein or other cytotoxic agent) will only occur in cells where the UPR is active. This can be useful to mitigate or avoid undesirable off-target expression of the functional therapeutic expression product.

Accordingly, in the various aspects of the invention directed to therapy, it a preferred that the condition to be treated is cancer or infection (e.g. infection with a virus).

Alternatively, UPR can be induced in cells using a suitable UPR-inducing agent. Various UPR-inducing agents are discussed above, and suitable UPR-inducing agents include pharmaceutically acceptable agents that induce the UPR (e.g. Bortezomib, forskolin) and agents that disturb the lipid balance in the cells to induce the UPR (e.g. saturated fatty acids as discussed above). The UPR-inducing agent can be deliver directly to a target suite (e.g. by injection) or given systemically.

The therapeutic expression product may be a polypeptide/protein, e.g. a secretable protein or peptide such as, e.g., clotting factors, such as factor VII I or factor IX, insulin, erythropoietin, lipoprotein lipase, antibodies or nanobodies, growth factors, cytokines, chemokines, plasma factors, toxic proteins, etc. Alternatively, the therapeutic expression product may be RNA, such as siRNA or miRNA.

In some preferred embodiments, the therapeutic expression product may be toxic for the cells into which the gene therapy vector has been introduced. In such embodiments, induction of the UPR can be used to induce toxicity in cells, e.g. leading to cell death.

Accordingly, induction of the UPR and consequent expression of the therapeutic expression product can be used to induce a kill switch in said cells. Suitable toxic expression products, such as proteins, are well known in the art, and mention can be made of caspase 3, caspase 8, and caspase 9, for example.

Suitable gene therapy vectors for use in this aspect of the invention are discussed above.

Gene therapy protocols have been extensively described in the art. These include, but are not limited to, intramuscular injection of a suitable vector, hydrodynamic gene delivery in various tissues, including muscle, interstitial injection, instillation in airways, application to endothelium, intrahepatic parenchyme, and intravenous or intra-arterial administration. Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure. These delivery paradigms can also be used to deliver vectors. Another approach to targeted gene delivery is the use of molecular conjugates, which consist of protein or synthetic ligands to which a nucleic acid- or DNA-binding agent has been attached for the specific targeting of nucleic acids to cells (Cristiano et al., 1993).

The terms "subject" and "patient" are used interchangeably herein and refer to animals, preferably vertebrates, more preferably mammals, and specifically include human patients and non-human mammals. "Mammalian" subjects include, but are not limited to, humans. Preferred patients or subjects are human subjects.

A "therapeutic amount" or "therapeutically effective amount" as used herein refers to the amount of expression product effective to treat a disease or disorder in a subject, i.e., to obtain a desired local or systemic effect. The term thus refers to the quantity of an expression product that elicits the biological or medicinal response in a tissue, system, animal, or human that is being sought by a researcher, veterinarian, medical doctor or other clinician. Such amount will typically depend on the gene product and the severity of the disease, but can be decided by the skilled person, possibly through routine experimentation.

Expression levels of the expression product (e.g. protein) can be measured by various conventional means, such as by antibody-based assays, e.g. a Western Blot or an ELISA assay, for instance to evaluate whether therapeutic expression of the expression product is achieved. Expression of the expression product may also be measured in a bioassay that detects an enzymatic or biological activity of the gene product.

In a further aspect the present invention provides a synthetic UPR-inducible promoter comprising a synthetic UPR-responsive cis-regulatory element. Suitably the UPR-responsive cis-regulatory element comprises at least one binding site for ATF6, XBP1 or bZIP60, or homologous or otherwise equivalent transcription factors that drive gene expression as part of the UPR.

Such a promoter can be used to selectively drive expression of a desired expression product in eukaryotic cells upon induction of the UPR. While it is may be advantageous in terms of tight control of gene expression that such a promoter is used in combination with a regulatable intron discussed above, in other circumstances a UPR-inducible promoter could be used without the regulatable intron.

A UPR-responsive cis-regulatory element is a sequence that contains functional transcription factor binding site(s) (TFBS) for one or more transcription factors that drive gene expression as part of the UPR. As discussed above, these include, but are not limited to, ATF6, XBP1 and bZIP60. UPR-responsive cis-regulatory elements comprising TFBS for ATF6 are of particular interest in the present invention. Preferably the UPR-responsive cis-regulatory element is UPR-specific, i.e. it only enhances expression during the UPR. For example, it is generally preferred that it does not contain any TFBS for transcription factors that are not involved in the UPR.

The synthetic UPR-inducible promoter typically comprises at least one synthetic UPR-responsive cis-regulatory element operably linked to a minimal promoter or proximal promoter. Where the cis-regulatory element is operably linked to a proximal promoter, the proximal promoter should itself be a UPR-inducible promoter that does not drive transcription of an operably linked gene in a eukaryotic cell when the UPR has not been induced. Minimal promoters cannot typically drive expression without the presence of additional regulatory elements. Examples of suitable minimal promoters for use in the present invention include, but are not limited to the CMV-minimal (SEQ ID NO: 21) promoter and the MinTk minimal promoter. Other suitable minimal promoters are known in the art.

Suitably the UPR-inducible promoter comprises a UPR-responsive cis-regulatory element comprising one or more copies of the at least one of the following transcription factor target sequences:

```
TGACGTG (the ATF6 transcription factor binding
site consensus sequence),

TGACGTGCT (a variant of the above)

(known as the UPRE site)
TGACGTG[TG], (SEQ ID NO: 18)
CCAAT-N9-CCACG (known as the ERSE1 site),
and (SEQ ID NO: 19)
ATTGG-N-CCACG (known as the ERSE2 site).
```

Suitably the synthetic UPR-responsive cis-regulatory element comprises two or more, preferably three or more, suitably five or more, copies of at least one of the transcription factor target sequences listed above. Alternatively, or additionally, the synthetic UPR-responsive cis-regulatory element suitably comprises one or more copies of at least two of the transcription factor target sequences listed above.

The transcription factor target sequences may be directly adjacent to each other (tandem repeats) or may be spaced apart, for example by a spacer sequence or another functional sequence (e.g. another transcription factor target sequence). Typically, the spacer sequence, if present, is from 5-50 nucleotides in length, but it can be longer or shorter in some cases. For example, the spacer sequence is suitably from 2 to 50 nucleotides in length, suitably from 4 to 30 nucleotides in length, or suitably from 5 to 20 nucleotides in length. It may be preferred that the spacer sequence is a multiple of 5 nucleotides in length, as this provides an integer number of half-turns of the DNA double helix (a full turn corresponding to approximately 10 nucleotides in chromatin). A spacer sequence length that is a multiple of 10 nucleotides in length may be more preferable, as it provides an integer number of full-turns of the DNA double helix. The spacer sequence can have essentially any sequence, provided it does not prevent the UPR-responsive cis-regulatory element from functioning as desired (e.g. it includes a silencer sequence, prevents binding of the desired transcription factor, or suchlike). The spacer sequences between each transcription factor target sequence can be identical or they can be different.

In a preferred embodiment the UPR-responsive cis-regulatory element comprises one or more copies of the transcription factor target sequence TGACGTG (i.e. the ATF6 consensus sequence), preferably 3 or more copies of the transcription factor target sequence TGACGTG, and preferably 5 or more copies of the transcription factor target sequence TGACGTG, for example 6 or more copies of the transcription factor target sequence TGACGTG. As mentioned above, these transcription factor target sequences may be in tandem repeat or may be spaced from each other. Generally, it is preferred that at least two, and preferably all, of the transcription factor target sequences present in the UPR-responsive cis-regulatory element are spaced from each other, e.g. by a spacer sequence as discussed above.

Suitably the UPR-responsive cis-regulatory element comprises one or more copies of the transcription factor target sequence TGACGTGCT, preferably 3 or more copies of the transcription factor target sequence TGACGTGCT, preferably 5 or more copies of the transcription factor target sequence TGACGTGCT, for example 6 or more copies of the transcription factor target sequence TGACGTGCT. As mentioned above, these may be in tandem repeat, or may be spaced from each other. Generally, it is preferred that at least two, and preferably all, of the transcription factor target sequences present in the UPR-responsive cis-regulatory element are spaced from each other, e.g. by a spacer sequence as discussed above. The transcription factor target sequence TGACGTGCT has been found to be particularly effective when used in multiple copy number in a UPR-responsive cis-regulatory element, whether as a tandem repeat or including spacer sequences.

In some embodiments of the present invention the UPR-responsive cis-regulatory element comprises the sequence

```
                                       (SEQ ID NO: 54)
TGACGTG-S-TGACGTG-S-TGACGTG-S-TGACGTG-S-TGACGTG-

S-TGACGTG
``` where S represents an optional spacer sequence as defined above. Preferably spacer sequences as defined above are present between at least two, and preferably all, of the transcription factor target sequences (TGACGTG).

In some embodiments of the present invention the UPR-responsive cis-regulatory element comprises the sequence

```
                                       (SEQ ID NO: 20)
TGACGTGCTTGACGTGCTTGACGTGCTTGACGTGCTTGACGTGCTT

GACGTGCT.
```

In other embodiments of the present invention the UPR-responsive cis-regulatory element comprises the sequence

```
                                       (SEQ ID NO: 55)
TGACGTGCT-S-TGACGTGCT-S-TGACGTGCT-S-TGACGTGCT-

S-TGACGTGCT-S-TGACGTGCT
``` where S represents an optional spacer sequence as defined above. Preferably spacer sequences as defined above are present between at least two, and preferably all, of the transcription factor target sequences.

In other embodiments of the present invention the UPR-responsive cis-regulatory element comprises the sequence

```
                                       (SEQ ID NO: 56)
TGACGTGCTGATGATGCGTAGCTAGTAGTTGACGTGCTGATGATGC

GTAGCTAGTAGTTGACGTGCTGATGATGCGTAGCTAGTAGTTGACG
```

-continued

```
TGCTGATGATGCGTAGCTAGTAGTTGACGTGCTGATGATGCGTAGC

TAGTAGTTGACGTGCT
``` or a sequence that is at least 50% identical thereto, yet more preferably at least 70% identical thereto, yet more preferably at least 80% identical thereto, and yet more preferably at least 85%, 90%, 995%, 98% or 99% identical thereto. It is highly preferred that sequence variation only occurs in sequences which are not the transcription factor target sequences, i.e. those having the sequence TGACGTGCT. It is generally preferred that sequence variation only occurs in spacer sequences (i.e. those having the sequence

```
                                        (SEQ ID NO: 61))
        GATGATGCGTAGCTAGTAGT.
```

In some embodiments of the present invention the UPR-inducible promoter comprises the following sequence

```
                                        (SEQ ID NO: 22)
TGACGTGCTTGACGTGCTTGACGTGCTTGACGTGCTTGACGTGCT

TGACGTGCTGGTACCGTCGACGATATCGGATCCAGGTCTATATAA

GCAGAGCTCGTTTAGTGAACCGTCAGATCGCCTAGATACGCCATC

CACGCTGTTTTGACCTCCATAGAAGATCGCCACC
``` or a sequence that is at least 70% identical thereto, yet more preferably at least 80% identical thereto, yet more preferably at least 90% identical thereto, and yet more preferably at least 95%, 96%, 97%, 98% or 99% identical thereto. This UPR-inducible promoter comprises the UPR-responsive cis-regulatory element of SEQ ID NO: 20 operably linked to the CMV-MP minimal promoter. It is highly preferred that sequence variation only occurs in sequences which are not the transcription factor target sequences, i.e. those having the sequence TGACGTGCT, nor in the CMV-MP sequence.

In other embodiments of the present invention the UPR-inducible promoter comprises the following sequence:

```
                                        (SEQ ID NO: 57)
TGACGTGCTGATGATGCGTAGCTAGTAGTTGACGTGCTGATGATG

CGTAGCTAGTAGTTGACGTGCTGATGATGCGTAGCTAGTAGTTGA

CGTGCTGATGATGCGTAGCTAGTAGTTGACGTGCTGATGATGCGT

AGCTAGTAGTTGACGTGCTGATGATGCGTAGCTAGTAGTGCAGTT

AGCGTAGCTGAGGTACCGTCGACGATATCGGATCCAGGTCTATAT

AAGCAGAGCTCGTTTAGTGAACCGTCAGAT
``` or a sequence that is at least 50% identical thereto, yet more preferably at least 70% identical thereto, yet more preferably at least 80% identical thereto, and yet more preferably at least 85%, 90%, 995%, 98% or 99% identical thereto. This UPR-inducible promoter comprises the UPR-responsive cis-regulatory element of SEQ ID NO: 56 operably linked to the CMV-MP minimal promoter. It is highly preferred that sequence variation only occurs in sequences which are not the transcription factor target sequences, i.e. those having the sequence TGACGTGCT, nor in the CMV- MP sequence. It is generally preferred that sequence variation only occurs in spacer sequences (i.e. those having the sequence

```
                                        (SEQ ID NO: 61))
        GATGATGCGTAGCTAGTAGT.
```

In other embodiments of the present invention the UPR-inducible promoter comprises the following sequence:

```
                                        (SEQ ID NO: 58)
TGACGTGCTGATGATGCGTAGCTAGTAGTTGACGTGCTGATGAT

GCGTAGCTAGTAGTTGACGTGCTGATGATGCGTAGCTAGTAGTT

GACGTGCTGATGATGCGTAGCTAGTAGTTGACGTGCTGATGATG

CGTAGCTAGTAGTTGACGTGCTGATGATGCGTAGCTAGTAGTGC

AGITAGCGTAGCTGAGGTACCGTCGACGATATCGGATCCTTCGC

ATATTAAGGTGACGCGTGTGGCCTCGAACACCGAG
``` or a sequence that is at least 50% identical thereto, yet more preferably at least 70% identical thereto, yet more preferably at least 80% identical thereto, and yet more preferably at least 85%, 90%, 995%, 98% or 99% identical thereto. This UPR-inducible promoter comprises the UPR-responsive cis-regulatory element of SEQ ID NO: 56 operably linked to the MinTK minimal promoter. It is highly preferred that sequence variation only occurs in sequences which are not the transcription factor target sequences, i.e. those having the sequence TGACGTGCT, nor in the MinTK sequence. It is generally preferred that sequence variation only occurs in spacer sequences (i.e. those having the sequence

```
                                        (SEQ ID NO: 61))
        GATGATGCGTAGCTAGTAGT.
```

The UPR-inducible promoter preferably does not drive transcription of an operably linked gene when present in a eukaryotic cell in the absence of the UPR. The UPR-inducible promoter drives transcription of an operably linked gene when present in a eukaryotic cell when the UPR is occurring in the cell. Assessment of the ability of a UPR-inducible promoter to selectively drive transcription upon induction of the UPR can readily be assessed by the skilled person using a wide range of approaches, and these can be tailored for the particular expression system in which the construct is intended to be used. As one preferred example, the methodology described in the examples below can be used, e.g. Example 8. For example, any candidate UPR-inducible promoter to be assessed can be substituted into the construct described in Example 8 in place of the exemplary ATF6-containing UPR-inducible promoter used in Example 8, and the ability of said candidate UPR-inducible promoter to selectably drive transcription when the UPR is induced can be measured by assessing the level of luciferase expression before and after UPR induction by 2 mM DTT, exactly as carried out in Example 8. A UPR-inducible promoter is one which is able to be successfully induced to significantly increase transcription of an operably linked gene (in the case of Example 8, the luciferase gene) upon induction of the UPR to result in the expression of the gene. Preferably a UPR-inducible promoter confers at least a 5-fold increase in expression 24 hours after induction of the UPR with 2 mM DTT, more preferably at least a 10-fold increase in expression, more preferably at least a 100-fold increase in expression, and yet more preferably at least a 1000-fold increase in expression of the gene (e.g. luciferase). It is preferred that before induction of the UPR the expression levels of the gene (e.g. luciferase) are minimal, and preferably negligible. Minimal expression can be defined as, for example, equal to or less than the expression levels of a negative control construct as used in Example 8 (i.e. a construct without in which expression of the sequence encoding the luciferase is driven by CMV-MP alone), preferably less than 50%, preferably less than 20%, more preferably less than 10%, yet more preferably less than 5%, yet more preferably less than 1% of the expression levels of a negative control construct. Negligible expression levels are, for example, those that are essentially undetectable using the methodology of Example 8.

The present invention also provides an expression construct or vector comprising a synthetic UPR-inducible promoter as set out above, operably linked to a nucleic acid sequence encoding an expression product. The expression construct or vector can be any expression construct or vector as discussed above for the other aspects of the invention. The expression product can be any expression product as discussed above for the other aspects of the invention (e.g. encoding a protein).

In preferred embodiments the expression product is not a reporter protein, i.e. it does not encode a protein that is used conventionally as an indicator of expression levels. Many reporter genes are known in the art, including, in particular, fluorescent, luminescent proteins and chromogenic proteins. Thus, in some preferred embodiments the expression product is not a fluorescent or luminescent protein, e.g. it is not a luciferase. As set out above, preferred expression products include therapeutic proteins and toxic proteins.

In a further aspect the present invention provides a method for producing an expression product, the method comprising:

a) providing a population of eukaryotic cells comprising a synthetic nucleic acid expression construct comprising a UPR-inducible promoter operably linked to a nucleic acid sequence encoding an expression product according to the present invention;

b) treating said population of cells so as to induce the unfolded protein response, thereby inducing transcription from the UPR-inducible promoter;

c) incubating said population of cells under suitable conditions for production of the expression product; and d) isolating the expression product from said population of cells.

Further optional and preferred features of methods for producing an expression product are discussed above for the other aspects of the invention, and these apply to the present aspect mutatis mutandis. It is preferred that the expression product is a therapeutic protein or a toxic protein. It is preferred that the expression product is not a reporter protein Accordingly, a further aspect of the invention provides a pharmaceutical composition comprising a nucleic acid expression construct or a vector comprising a UPR-inducible promoter operably linked to a nucleic acid sequence encoding an expression product according to the present invention. Further optional and preferred features of pharmaceutical composition are discussed above for the other aspects of the invention, and these apply to the present aspect mutatis mutandis.

In a further aspect of the invention there is provided the use of nucleic acid expression constructs and vectors comprising a UPR-inducible promoter operably linked to a nucleic acid sequence encoding an expression product according to the present invention for the manufacture of a pharmaceutical composition.

According to a further aspect of the present invention there is provided a cell comprising a synthetic nucleic acid expression construct or vector comprising a UPR-inducible promoter according to the present invention. Further optional and preferred features of such cells are discussed above for the other aspects of the invention, and these apply to the present aspect mutatis mutandis.

In a further aspect, the invention provides the nucleic acid expression constructs, vectors, cells or pharmaceutical compositions comprising a UPR-inducible promoter according to the present invention for use in a method of treatment or therapy. Further optional and preferred features of such methods are discussed above for the other aspects of the invention, and these apply to the present aspect mutatis mutandis.

To facilitate the understanding of this invention, a number of terms are defined below. Terms defined herein have meanings as commonly understood by a person of ordinary skill in the areas relevant to the present invention. The terminology herein is used to describe specific embodiments of the invention, but their usage does not delimit the invention, except as set out in the claims.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Ausubel, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); U.S. Pat. No. 4,683,195; Nucleic Acid Hybridization (Harries and Higgins eds. 1984); Transcription and Translation (Hames and Higgins eds. 1984); Culture of Animal Cells (Freshney, Alan R. Liss, Inc., 1987); Immobilized Cells and Enzymes (IRL Press, 1986); Perbal, A Practical Guide to Molecular Cloning (1984); the series, Methods in Enzymology (Abelson and Simon, eds. -in-chief, Academic Press, Inc., New York), specifically, Vols. 154 and 155 (Wu et al. eds.) and Vol. 185, "Gene Expression Technology" (Goeddel, ed.); Gene Transfer Vectors For Mammalian Cells (Miller and Calos eds., 1987, Cold Spring Harbor Laboratory); Immunochemical Methods in Cell and Molecular Biology (Mayer and Walker, eds., Academic Press, London, 1987); Handbook of Experimental Immunology, Vols. I-IV (Weir and Blackwell, eds., 1986); and Manipulating the Mouse Embryo, (Cold Spring Harbor Laboratory Press, Cold Spring Harbor, N.Y., 1986).

Terms such as "a", "an" and "the" are not intended to refer to only a singular entity, but include the general class of which a specific example may be used for illustration.

The terms "comprising", "comprises" and "comprised of" as used herein are synonymous with "including", "includes" or "containing", "contains", and are inclusive or open-ended and do not exclude additional, non-recited features, elements or method steps.

The recitation of numerical ranges by endpoints includes all numbers and fractions subsumed within the respective ranges, as well as the recited endpoints.

The term "nucleic acid" as used herein typically refers to an oligomer or polymer (preferably a linear polymer) of any length composed essentially of nucleotides. A nucleotide unit commonly includes a heterocyclic base, a sugar group, and at least one, e.g. one, two, or three, phosphate groups, including modified or substituted phosphate groups. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups. Nucleic acids as intended herein may include naturally occurring nucleotides, modified nucleotides or mixtures thereof. A modified nucleotide may include a modified heterocyclic base, a modified sugar moiety, a modified phosphate group or a combination thereof. Modifications of phosphate groups or sugars may be introduced to improve stability, resistance to enzymatic degradation, or some other useful property. The term "nucleic acid" further preferably encompasses DNA, RNA and DNA RNA hybrid molecules, specifically including hnRNA, pre-mRNA, mRNA, cDNA, genomic DNA, amplification products, oligonucleotides, and synthetic (e.g., chemically synthesised) DNA, RNA or DNA RNA hybrids. A nucleic acid can be naturally occurring, e.g., present in or isolated from nature; or can be non-naturally occurring, e.g., recombinant, i.e., produced by recombinant DNA technology, and/or partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

"Nucleic acid expression construct" as used herein refers to nucleic acid molecules that include one or more transcriptional control elements (such as, but not limited to promoters, enhancers and/or regulatory elements, polyadenylation sequences, and introns) that direct expression in one or more desired cell types, tissues or organs. Nucleic acid expression constructs of the present invention are synthetic nucleic acid molecules.

"Synthetic" in the present application means a nucleic acid molecule that does not occur in nature. Synthetic nucleic acid expression constructs of the present invention are produced artificially, typically by recombinant technologies. Such synthetic nucleic acids may contain naturally occurring sequences (e.g. promoter, enhancer, intron, and other such regulatory sequences), but these are present in a non-naturally occurring context. For example, a synthetic gene (or portion of a gene) typically contains one or more nucleic acid sequences that are not contiguous in nature (chimeric sequences), and/or may encompass substitutions, insertions, and deletions and combinations thereof.

The term "operably linked", "operably connected" or equivalent expressions as used herein refer to the arrangement of various nucleic acid elements relative to each such that the elements are functionally connected and are able to interact with each other in the manner intended. Such elements may include, without limitation, a promoter, an enhancer and/or a regulatory element, a polyadenylation sequence, one or more introns and/or exons, and a coding sequence of a gene of interest to be expressed. The nucleic acid sequence elements, when properly oriented or operably linked, act together to modulate the activity of one another, and ultimately may affect the level of expression of an expression product. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements. As understood by the skilled person, operably linked implies functional activity, and is not necessarily related to a natural positional link. Indeed, when used in nucleic acid expression cassettes, cis-regulatory elements will typically be located immediately upstream of the promoter (although this is generally the case, it should definitely not be interpreted as a limitation or exclusion of positions within the nucleic acid expression cassette), but this needs not be the case in vivo. E.g., a regulatory element sequence naturally occurring downstream of a gene whose transcription it affects is able to function in the same way when located upstream of the promoter. Hence, according to a specific embodiment, the regulatory or enhancing effect of the regulatory element is position-independent.

"Consensus sequence"—the meaning of consensus sequence is well-known in the art. In the present application, the following notation is used for the consensus sequences, unless the context dictates otherwise. Considering the following exemplary DNA sequence:

A[CT] N{A}YR

A means that an A is always found in that position; [CT] stands for either C or T in that position; N stands for any base in that position; and {A} means any base except A is found in that position. Y represents any pyrimidine, and R indicates any purine.

"Regulatable intron" in the present application, unless the context dictates otherwise, refers to a nucleic acid sequence occurring in an RNA molecule (typically a transcript) comprising an excisable sequence flanked by target sites for a ribonuclease, generally IRE1 or a homologue or orthologue thereof, wherein the excisable sequence can be excised from the RNA molecule by the action of said ribonuclease as a result of the unfolded protein response. In some cases in the art the term intron is used to refer exclusively to the sequence which is excised (i.e. spliced out) from the RNA molecule, but in the case of the regulatable introns of the present invention that is less appropriate.

The terms "identity" and "identical" and the like refer to the sequence similarity between two polymeric molecules, e.g., between two nucleic acid molecules, e.g., two DNA molecules. Sequence alignments and determination of sequence identity can be done, e.g., using the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250).

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, MD), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method. Typically, the percentage sequence identity is calculated over the entire length of the sequence.

For example, a global optimal alignment is suitably found by the Needleman-Wunsch algorithm with the following scoring parameters: Match score: +2, Mismatch score: –3; Gap penalties: gap open 5, gap extension 2. The percentage identity of the resulting optimal global alignment is suitably calculated by the ratio of the number of aligned bases to the total length of the alignment, where the alignment length includes both matches and mismatches, multiplied by 100.

"Cell culture", as used herein, refers to a proliferating mass of cells that may be in either an undifferentiated or differentiated state.

"Cis-regulatory element" or "CRE", as used herein, is a term known to the skilled person; it relates to a region of non-coding DNA which regulates the transcription of a neighbouring gene (i.e. in cis). CREs typically regulate gene transcription by binding to transcription factors. A CRE can be an enhancer, promoter, insulator or silence, for example. In the present case the UPR-inducible CRE is typically an enhancer element which binds to transcription factors that act to induce transcription as part of the UPR. In the present context, when the CRE is provided as part of a promoter and a gene encoding an expression product, it is preferred that the UPR-inducible CRE is located 1500 nucleotides or less from the transcription start site (TSS), more preferably 1000 nucleotides or less from the TSS, more preferably 500 nucleotides or less from the TSS, and suitably 250, 200, 150, or 100 nucleotides or less from the TSS.

"Complementary" or "complementarity", as used herein, refers to the Watson-Crick base-pairing of two nucleic acid sequences. For example, for the sequence 5'-AGT-3' binds to the complementary sequence 3'-TCA-5'. Complementarity between two nucleic acid sequences may be "partial", in which only some of the bases bind to their complement, or it may be complete as when every base in the sequence binds to its complementary base. The degree of complementarity between nucleic acid strands has significant effects on the efficiency and strength of hybridization between nucleic acid strands.

"Conventional intron" as used herein refers to introns that are conventionally present in pre-mRNA, typically spliceosomal introns, that do not encode information for protein synthesis and is removed from an mRNA molecule before translation of the mRNA. The term is used to differentiate such introns from the non-canonical regulatory introns of the present invention.

"Transfection" in the present application refers broadly to any process of deliberately introducing nucleic acids into cells, and covers introduction of viral and non-viral vectors, and includes transformation, transduction and like terms. Examples include, but are not limited to: transfection with viral vectors; transformation with plasmid vectors; electroporation (Fromm et al. (1986) Nature 319:791-3); lipofection (Feigner et al. (1987) Proc. Natl. Acad. Sci. USA 84:7413-7); microinjection (Mueller et al. (1978) Cell 15:579-85); *Agrobacterium*-mediated transfer (Fraley et al. (1983) Proc. Natl. Acad. Sci. USA 80:4803-7); direct DNA uptake; whiskers-mediated transformation; and microprojectile bombardment (Klein et al. (1987) Nature 327:70).

As used herein, the phrase "transgene" refers to an exogenous nucleic acid sequence. In one example, a transgene is a gene sequence, a gene encoding an industrially or pharmaceutically useful compound, or a gene encoding a desirable trait. In yet another example, the transgene is an antisense nucleic acid sequence, wherein expression of the antisense nucleic acid sequence inhibits expression of a target nucleic acid sequence.

As used herein, the phrase "promoter" refers to a region of DNA that generally is located upstream of a nucleic acid sequence to be transcribed that is needed for transcription to occur. Promoters permit the proper activation or repression of transcription of sequence under their control. A promoter typically contains specific sequences that are recognized and bound by transcription factors, e.g. enhancer sequences. Transcription factors bind to the promoter DNA sequences and result in the recruitment of RNA polymerase, an enzyme that synthesizes RNA from the coding region of the gene. A great many promoters are known in the art.

As used herein, "minimal promoter" refers to a short DNA segment which is inactive or largely inactive by itself, but can mediate strong transcription when combined with other transcription regulatory elements. Minimum promoter sequence can be derived from various different sources, including prokaryotic and eukaryotic genes. Examples of minimal promoters are dopamine beta-hydroxylase gene minimum promoter and cytomegalovirus (CMV) immediate early gene minimum promoter (CMV-MP) and the herpes thymidine kinase minimal promoter (MinTK).

"RNA transcript" or "transcript" refers to the product resulting from RNA polymerase-catalysed transcription of a DNA sequence. When the RNA transcript is a, typically perfect, complementary copy of the DNA sequence, it is referred to as the primary transcript or it may be a RNA sequence derived from post-transcriptional processing of the primary transcript and is referred to as the mature RNA.

"Messenger RNA" or "(mRNA)" refers to the processed form of the transcript RNA that is without introns and that can be translated into protein by the cell.

Embodiments of the present invention will now be described, by way of non-limiting example, with reference to the accompanying drawings.

BRIEF DESCRIPTION OF THE FIGURES

FIG. 7 shows EGFP fluorescence from HEK293F cells before and after induction with wtAAV. Zs Green is a recombinant AAV makes a variant of GFP that is used as a control, pre-AS-green is no transfection (i.e. blank).

FIG. 11 shows a graph of expression of SEAP after induction with DTT in CHO and HEK293 cells, compared with expression of SEAP under control of the CMV-IE promoter (results shown are in HEK293). (X-axis shows hours after induction) FIG. 12A shows a graph of expression of luciferase after induction with DTT or palmitate in CHO (A) and HEK293 (B) cells (X-axis units are hours). FIG. 12B shows expression of luciferase under control of the CMV-IE promoter and CMV minimal promoter (CMV-MP).

FIG. 15 shows a graph of HEK293 cell viability following induction of caspase 9 with DTT compared with a negative control (HEK293 cells plus DTT) and CASP9 under control of the CMV-IE promoter.

FIG. 16A-D shows the predicted secondary structures formed when the introns as used in:

```
A. SEAP
                                  (SEQ ID NO: 33)
(CAG/CAGACGGGCAACTTTACACGACGCTG/CAG)

B. EGFP
                                  (SEQ ID NO: 48)
(CAG/CTGGAGCACTCAGACTACGTGCACCTCTG/CTG)
```

```
-continued
C. CASP9
                                  (SEQ ID NO: 43)
(CAG/CAGACGGGCAACTTTACACGACGCTG/CTG)

D. Luciferase
                                  (SEQ ID NO: 38)
(CCG/CAGACGGGCAACTTTACACGACGCTG/CAG)
```

FIGS. 16A-D disclose SEQ ID NOS 62-65, respectively, in order of appearance.

Figure 17:
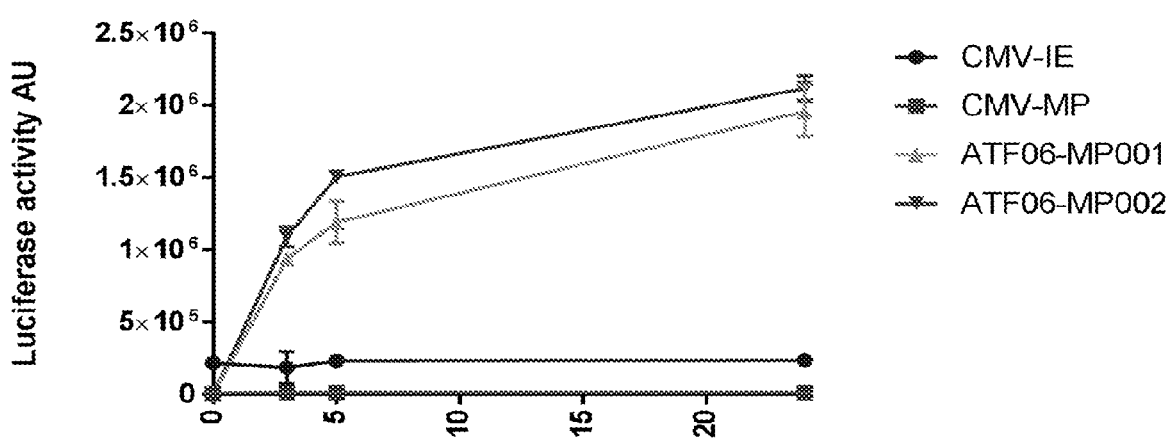

FIG. 17 shows a graph of expression of luciferase after induction with DDT (X-axis units are hours after induction) when a UPR-responsive cis-regulatory element containing 5×ATF6 binding sites combined with two different minimal promoters. Controls were the CMV-IE promoter and the CMV-minimal promoter without any additional regulatory sequences.

SPECIFIC DESCRIPTION OF EMBODIMENTS OF THE INVENTION

Example 1: Use of the XBP1 Intron as Regulation Mechanism for Protein Expression A 26 bp non-conventional intron (regulatable) is present in the mRNA of XBP1 which, prior to splicing, codes for a nonsense protein. Once endoplasmic reticulum (ER) stress has been sensed via the IRE1 protein, the non-conventional intron is removed via unique splicing sites and the mRNA subsequently re-ligated to form an mRNA transcript that can be translated to make the XBP1 protein. ER stress can be induced in many ways, e.g. via chemical addition or via expression of heterologous proteins.

The inventors have recognised that this process can be adapted for regulating protein expression at the mRNA/translation level by including the regulatable intron, including suitable splice sites in the sequence of a gene of interest. Under the control of a suitable promoter, the mRNA is made but cannot be processed to form the functional expression product of the gene of interest. However, once the UPR is induced, e.g. via administration of DTT or expression of another heterologous protein, the mRNA is processed, the regulatable intron is spliced out and the mRNA can be translated into a functional protein.

By using this mechanism, the production of proteins (e.g. toxic proteins) can be tailored to fit the manufacturing process as induction is required before the protein is made. Thus, for example, translation of the protein can be delayed until a desired stage in fermentation has been reached. This method can also be used for non-protein expression products, such as functional RNAs (e.g. siRNA or miRNAs).

Splice Sites and Intron

Consensus Splice Recognition Site Sequence for IRE1:

CNG/CNG

This consensus sequence is conserved across eukaryotes. The consensus sequence CNG/CNG[CG], with a preference for CNG/CNGC, is typically found in mammalian cells, thought the CNG/CNG consensus sequence can be used.

WT Mammalian XBP1 Splice Recognition Site Sequence:

```
5' site:
CCG/CAGC

3' site:
CUG/CAGC
```

WT Intron Sequence from Mammals:

(SEQ ID NO: 23):
cagcacucagacuacgugcaccucug

WT Mammal Intron Including Excised Sequence Flanked by Splice Recognition Site Sequences:

(SEQ ID NO: 24)
CCG/cagcacucagacuacgugcaccucug/CAGC

Construction of the EGFP sequence including regulatable intron The region chosen for insertion of the intron was due to sequence similarity to the splice recognition sites. Only a single silent mutation, CTCG to CTGG, was required at the 3' recognition site to allow for the insertion of the intron.

EGFP gene sequence with underlined region for intron insertion (SEQ ID NO: 25):
ATGGTGAGCAAGGGCGAGGAGCTGTTCACCGGGGTGGTGCCCATCCTG

GTCGAGCTGGACGGCGACGTAAACGGCCACAAGTTCAGCGTGTCCGGC

GAGGGCGAGGGCGATGCCACCTACGGCAAGCTGACCCTGAAGTTCATC

TGCACCACCGGCAAGCTGCCCGTGCCCTGGCCCACCCTCGTGACCACC

CTGACCTACGGCGTGCAGTGCTTCAGCCGCTACCCCGACCACATGAAG

CAGCACGACTTCTTCAAGTCCGCCATGCCCGAAGGCTACGTCCAGGAG

CGCACCATCTTCTTCAAGGACGACGGCAACTACAAGACCCGCGCCGAG

GTGAAGTTCGAGGGCGACACCCTGGTGAACCGCATCGAGCTGAAGGGC

ATCGACTTCAAGGAGGACGGCAACATCCTGGGGCACAAGCTGGAGTAC

AACTACAACAGCCACAACCTCTATATCATGGCCGACAAGCAGAAGAAC

GGCATCAAGGTGAACTTCAAGATCCGCCACAACATCGAGGACGGCAGC

GTGCAG/CTCGCCGACCACTACCAGCAGAACACCCCCATCGGCGACGG

CCCCGTGCTGCTGCCCGACAACCACTACCTGAGCACCCAGTCCGCCCT

GAGCAAAGACCCCAACGAGAAGCGCGATCACATGGTCCTGCTGGAGTT

CGTGACCGCCGCCGGGATCACTCTCGGCATGGACGAGCTGTACAAG

EGFP protein sequence (SEQ ID NO: 26):
MVSKGEELFT GVVPILVELD GDVNGHKFSV SGEGEGDATY

GKLTLKFICT TGKLPVPWPT LVTTLTYGVQ CFSRYPDHMK

QHDFFKSAMP EGYVQERTIF FKDDGNYKTR AEVKFEGDTL

VNRIELKGID FKEDGNILGH KLEYNYNSHN VYIMADKQKN

GIKVNFKIRH NIEDGSVQLA DHYQQNTPIG DGPVLLPDNH

YLSTQSALSK DPNEKRDHMV LLEFVTAAGI TLGMDELYK

The sequence used in this study is shown below. GFP is underlined and the intron and splice sites are indicated in bold. In the present example, an additional 3 bp sequence was added to 5' end of the intron to create an intron that was expected to have slightly sub-optimal splicing. The intention was to keep the background expression levels, i.e. when UPR has not yet been induced, to a minimum. Suspension adapted cells are known to typically be in a slightly more stressed state than adherent cells, and thus this alight modification was expected to have benefits in avoiding background expression. The wild type intron can of course be used, and may be preferred in some cases. The intron sequence as used in the present example was as follows (additional 3 bp sequence is underlined):

(SEQ ID NO: 27)
CAG/cugcagcacucagacuacgugcaccucug/CUGG

EGFP sequence with regulatable XBP1 intron, CMV minimal promoter (CMV-MP) and SV40 polyA tail, the XBP1 intron sequence is in bold and the EGFP and the intron encoding sequence is underlined (this construct is named SYNP-XBP-01)

(SEQ ID NO: 28):
GGTACCGTCGACGATATCGGATCCAGGTCTATATAAGCAGAGCTCGTTTAGTGAACCGTCAGATCGCC

TAGATACGCCATCCACGCTGTTTTGACCTCCATAGAAGATCGCCACCATGGTGAGCAAGGGCGAGGAG

CTGTTCACCGGGGTGGTGCCCATCCTGGTCGAGCTGGACGGCGACGTAAACGGCCACAAGTTCAGCGT

GTCCGGCGAGGGCGAGGGCGATGCCACCTACGGCAAGCTGACCCTGAAGTTCATCTGCACCACCGGCA

AGCTGCCCGTGCCCTGGCCCACCCTCGTGACCACCCTGACCTACGGCGTGCAGTGCTTCAGCCGCTAC

CCCGACCACATGAAGCAGCACGACTTCTTCAAGTCCGCCATGCCCGAAGGCTACGTCCAGGAGCGCAC

CATCTTCTTCAAGGACGACGGCAACTACAAGACCCGCGCCGAGGTGAAGTTCGAGGGCGACACCCTGG

TGAACCGCATCGAGCTGAAGGGCATCGACTTCAAGGAGGACGGCAACATCCTGGGGCACAAGCTGGAG

TACAACTACAACAGCCACAACGTCTATATCATGGCCGACAAGCAGAAGAACGGCATCAAGGTGAACTT

CAAGATCCGCCACAACATCGAGGACGGCAGCGTGCAG/ctgcagcactcagactacgtgcacctctg/

CTGGCCGACCACTACCAGCAGAACACCCCCATCGGCGACGGCCCCGTGCTGCTGCCCGACAACCACTA

-continued

```
CCTGAGCACCCAGTCCGCCCTGAGCAAAGACCCCAACGAGAAGCGCGATCACATGGTCCTGCTGGAGT

TCGTGACCGCCGCCGGGATCACTCTCGGCATGGACGAGCTGTACAAGTGAGACGATCCTTATCGGATT

TTACCACATTTGTAGAGGTTTTACTTGCTTTAAAAAACCTCCCACATCTCCCCCTGAACCTGAAACAT

AAAATGAATGCAATTGTTGTTGTTAACTTGTTTATTGCAGCTTATAATGGTTACAAATAAAGCAATAG

CATCACAAATTTCACAAATAAAGCATTTTTTTCACTGCATTCTAGTTGTGGTTTGTCCAAACTCATCA

ATGTATCTTATCATGTCTGCTCGAAGGCGCGCCCTGGGCCTCATGGGCCTTCCGCTCACTGCCC
```

It can be seen that EGFP with the regulatable XBP1 intron inserted as set out above codes for a truncated protein (SEQ ID NOs: 29, 51, 52, 53— SEQ ID NOs: 51, 52, 53 refer to the fragmentary sequences falling after the initial stop codon, thought these will not be translated):

```
MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIEDGSVQLEHSDYVHLCWPTTTSRTPPSA

TAPCCCPTTTTStopAPSPPStopAKTPTRSAITWSCWSSStopPPPGSL

SAWTSCT
```

Figure 10:
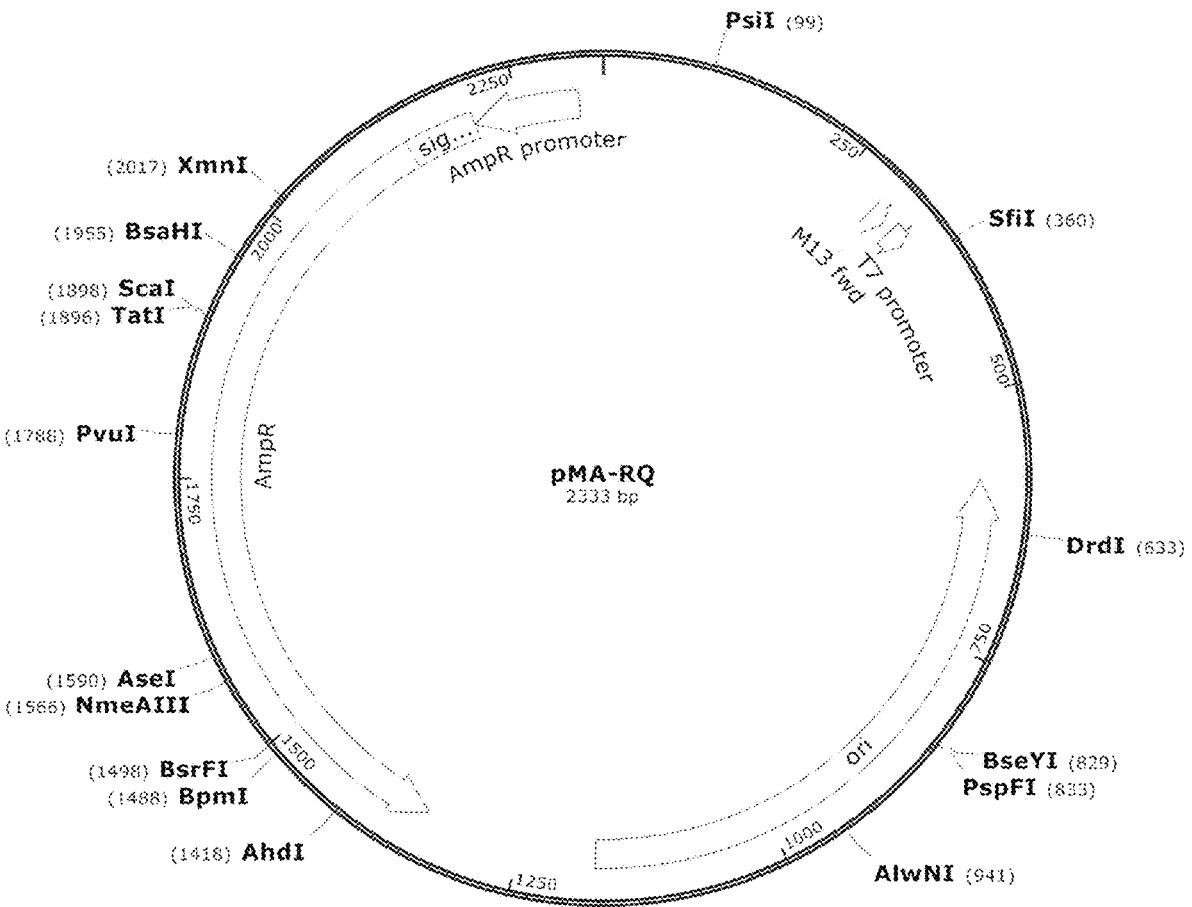
FIG. 10 shows a plasmid map of pMA-RQ.

DNA constructs used in this example:
CMV-MP-GFP: CMV-MP controlling expression of EGFP.
SYNP-XBP-01: CMV-MP controlling expression of EGFP with XBP1 intron.
These constructs are identical except for the presence of the intron in the EGFP coding sequence, as set out above.
All of these constructs were synthesised by Geneart and were provided in plasmid pMA-RQ (see FIG. 10 for a plasmid map). Plasmid pMA-RQ containing these constructs was directly transfected into the relevant cells.
Cell lines used in this example:
Freestyle HEK293F, Invitrogen cat no: R790-07.
Freestyle CHO-S, Invitrogen cat no: R80007.
Growth of HEK293F and CHO-S Cells:
Cells were maintained according the manufacturer's instructions.
Cells were transfected using MAX reagent, Invitrogen cat no: 16447100.
The standard protocol for transfection of these cells was modified for 24 well plates as follows:
40 ml of cells were grown in a 250 ml vented Erlenmeyer flask (Sigma-Aldrich CLS431144) at 37° C., 8% $CO_2$ with agitation at 100 rpm. Cells were seeded as described in the manufacturer's instructions.
1 day before transfection cells were counted using a haemocytometer and split to 500,000 cells/ml.
On the day of transfection cells are seeded to 1 million cells/ml in 500 μl of appropriate medium in a 24 well plate.
0.625 μg of DNA/well was then added to 10 μl of OptiMem medium (Thermofisher; 11058021) and incubated for 5 minutes at room temperature.
Concurrently 0.625 μl of Max reagent was made up to 10 μl by addition of OptiMem and incubated for 5 minutes at room temperature.
After this incubation both mixes were added to the same tube and incubated at room temperature for 25-30 minutes.

Figure 1:
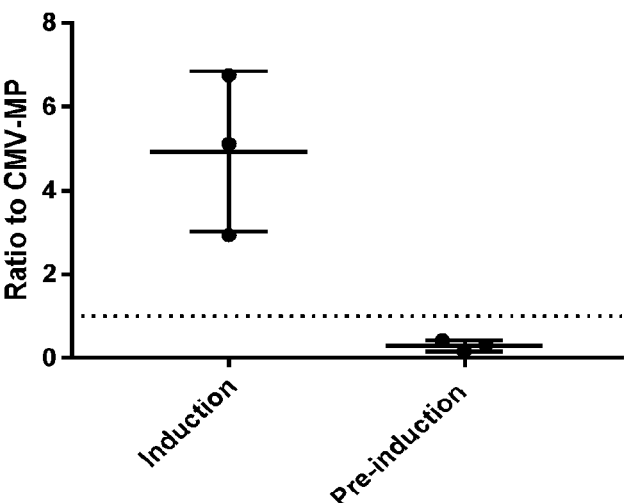
FIG. 1 shows ratio of GFP fluorescence from SYNP-XBP-01 transfected cells before and after induction by 2 mM DTT.

The DNA/Max reagent mix (20 μl/well) was then added directly to the cells and the cells incubated as described previously.
Cells were then measured for GFP fluorescence after 24 hrs.
Intron splicing from the GFP construct was measured via addition of 2 mM DTT and monitoring of GFP fluorescence after 1 hr. DTT is a strong reducing agent which induces ER stress by disrupting the formation of disulphide bonds within the ER.
Measurement of GFP Fluorescence:
Cell lysis buffer was prepared from the luciferase assay system (Promega; E1500) by diluting 1 in 5 with sterile water.
Cells were pelleted at 900×g for 5 minutes and re-suspended in 100 μl/1×10$^6$ cells of cell lysis buffer from the Luciferase kit.
This was then incubated for 10-15 minutes at room temperature for lysis to occur.
Cellular nuclei and debris was harvested at 900×g for 5 minutes.
The supernatant was collected and a max of 100 μl/sample to a 96 well black plate.
The supernatant was diluted 1 in 2 with PBS (this is to dilute out the mercaptoethanol from the lysis buffer which effects the GFP signal; GFP signal is decreased in the presence of reducing agents).
Sample was incubated for 5 minutes at room temperature.
GFP fluorescence was measured using a plate reader with excitation and emission set at 485 nm and 520 nm respectively.
GFP fluorescence was also visualised directly under a fluorescent microscope.
Results
SYNP-XBP-01 Experiments
HEK293F experiments:
24 well transfections were set-up as described above. Each condition was performed in duplicate/triplicate.
24 hrs after transfection the cells were treated with either 2 mM DTT or by mock treatment with an equivalent volume of water.
1 hr after treatment the cells GFP fluorescence was measured as described above.
The ratio of GFP fluorescence to the control plasmid was calculated before and after induction. FIG. 1 shows the cumulative results of 3 independent experiments.
FIG. 1 shows ratio of GFP fluorescence from SYNP-XBP-01 transfected cells before and after induction by 2 mM DTT. The results clearly show that upon inducing ER-Stress GFP production is induced 4-10-fold with the resultant activity 2.5-7-fold higher than the positive control. In addition, the background is considerably lower than the control (dashed line), clearly showing that expression of EGFP is being controlled by the regulatable intron. This indicates that intron is functional when placed in a heterologous gene (i.e. a gene other than XBP1), and facilitates inducible gene expression and higher expression levels.

Cho-S Experiments:

An experiment using CHO-S cells was performed in an identical manner as described for HEK293F cells. The result of the experiment can be seen in FIG. 2a and FIG. 2b.

Figure 2A:
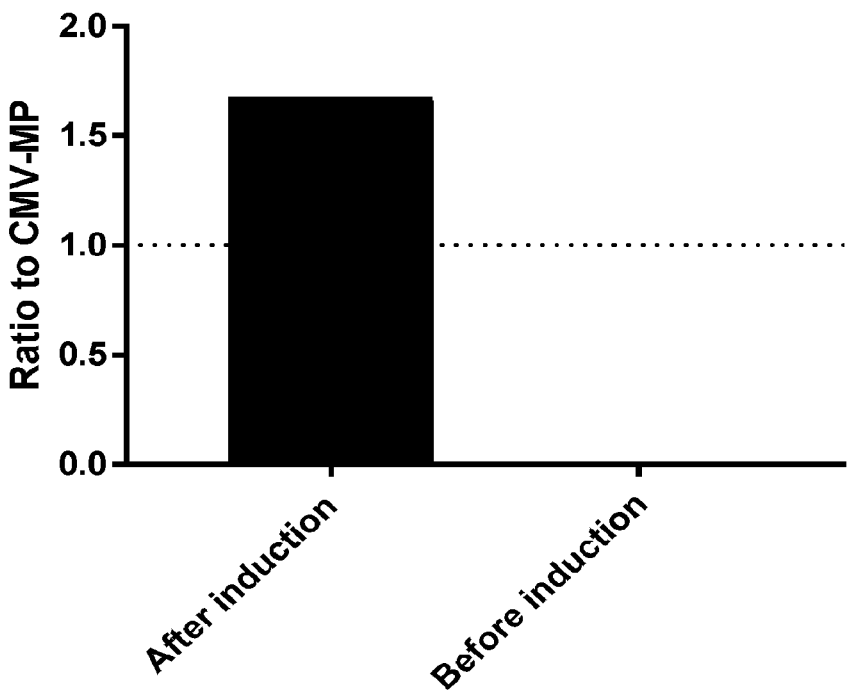
FIG. 2A shows the ratio of GFP fluorescence positive control before and after induction.
Figure 2B:
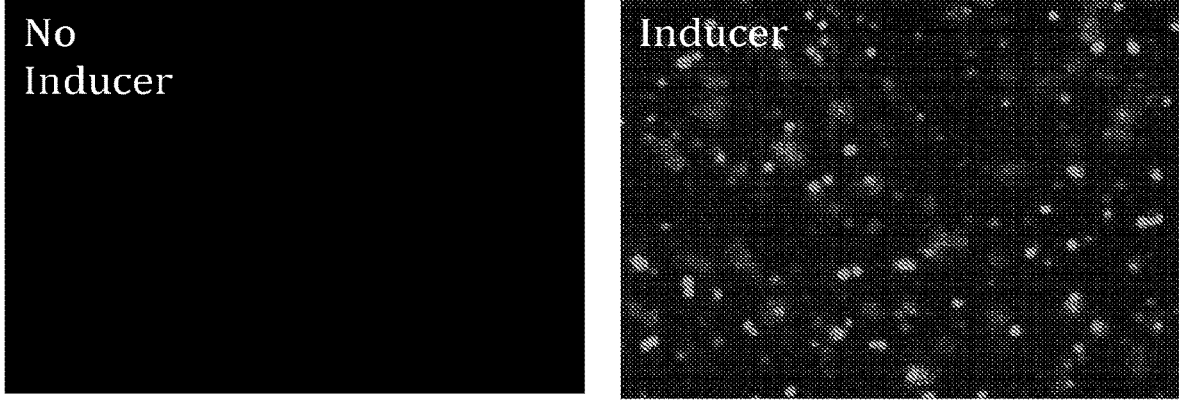
FIG. 2B shows fluorescence microscopy of SYNP-XBP-01 with and without 2 mM DTT.

FIG. 2a shows the ratio of GFP fluorescence positive control before and after induction. FIG. 2b shows fluorescence microscopy of SYNP-XBP-01 with and without 2 mM DTT. These data show that in CHO-S cells there is no background at all before induction and GFP fluorescence is therefore induced by >1000-fold upon addition of 2 mM DTT. Control in CHO-S cells may potentially be even tighter than that observed in HEK293F cells.

Example 2: Use of ATF6 Response Elements to Enhance Qene Expression and to Provide Exquisite Qene Control in Presence of the Requlatable XBP1 Intron ATF6 is a transcription factor that is activated by ER-stress. Once activated this transcription factor binds to ERSEs or UPREs and activates gene transcription of important components of protein homeostasis (see Yoshida et al., Cell, Vol. 107, 881-891, Dec. 28, 2001).

In this study, the inventors investigated the binding and gene expression enhancement of the ATF6 binding site, the mammalian UPRE, in the presence and absence of the XBP1 intron. This UPRE has a consensus sequence of TGACGTG and, in addition to ATF6, is also bound by XBP-1, therefore creating a potentially powerful feedback loop of gene expression based on ER-stress. The addition of the intron also allows the investigation of whether control at transcription and translation level confers better inducibility than each on its own.

For this study two constructs were prepared:

1) 6×ATF6 elements (having the sequence TGACGTGCT) upstream of the CMV-minimal promoter (CMV-MP) and EGFP; this construct was named SYNP-ATF6-01 (see below, SEQ ID NO: 30).

2) 6×ATF6 elements upstream of the CMV-MP and EGFP with XBP1 intron insertion; this construct was named SYNP-ATF6-02 (see below, SEQ ID NO: 31).

The intron was inserted into EGFP as described in Example 1.

HEK293F cells were used in this study. All growth conditions, transfections and analyses were carried out as described in Example 1.

Plasmids used in this study:

pMA-RQ containing the CMV-IE-GFP construct.

pMA-RQ containing the CMV-MP-GFP construct.

pMA-RQ containing the SYNP-ATF6-01 construct.

pMA-RQ containing the SYNP-ATF6-02 construct.

Sequence of SYNP-ATF6-01, the 6×ATF6 sites are underlined (SEQ ID NO: 30):
TGACGTGCTTGACGTGCTTGACGTGCTTGACGTGCTTGACGTGCTTGACG

TGCTGGTACCGTCGACGATATCGGATCCAGGTCTATATAAGCAGAGCTCG

TTTAGTGAACCGTCAGATCGCCTAGATACGCCATCCACGCTGTTTTGACC

TCCATAGAAGATCGCCACCATGGTGAGCAAGGGCGAGGAGCTGTTCACCG

GGGTGGTGCCCATCCTGGTCGAGCTGGACGGCGACGTAAACGGCCACAAG

-continued

TTCAGCGTGTCCGGCGAGGGCGAGGGCGATGCCACCTACGGCAAGCTGAC

CCTGAAGTTCATCTGCACCACCGGCAAGCTGCCCGTGCCCTGGCCCACCC

TCGTGACCACCCTGACCTACGGCGTGCAGTGCTTCAGCCGCTACCCCGAC

CACATGAAGCAGCACGACTTCTTCAAGTCCGCCATGCCCGAAGGCTACGT

CCAGGAGCGCACCATCTTCTTCAAGGACGACGGCAACTACAAGACCCGCG

CCGAGGTGAAGTTCGAGGGCGACACCCTGGTGAACCGCATCGAGCTGAAG

GGCATCGACTTCAAGGAGGACGGCAACATCCTGGGGCACAAGCTGGAGTA

CAACTACAACAGCCACAACGTCTATATCATGGCCGACAAGCAGAAGAACG

GCATCAAGGTGAACTTCAAGATCCGCCACAACATCGAGGACGGCAGCGTG

CAGCTCGCCGACCACTACCAGCAGAACACCCCCATCGGCGACGGCCCCGT

GCTGCTGCCCGACAACCACTACCTGAGCACCCAGTCCGCCCTGAGCAAAG

ACCCCAACGAGAAGCGCGATCACATGGTCCTGCTGGAGTTCGTGACCGCC

GCCGGGATCACTCTCGGCATGGACGAGCTGTACAAGTGA

Sequence of SYNP-ATF6-02 the 6×ATF6 sites are underlined and the excised intron sequence is shown in lower case and bold (SEQ ID NO: 31):
TGACGTGCTTGACGTGCTTGACGTGCTTGACGTGCTTGACGTGCTTGACG

TGCTGGTACCGTCGACGATATCGGATCCAGGTCTATATAAGCAGAGCTCG

TTTAGTGAACCGTCAGATCGCCTAGATACGCCATCCACGCTGTTTTGACC

TCCATAGAAGATCGCCACCATGGTGAGCAAGGGCGAGGAGCTGTTCACCG

GGGTGGTGCCCATCCTGGTCGAGCTGGACGGCGACGTAAACGGCCACAAG

TTCAGCGTGTCCGGCGAGGGCGAGGGCGATGCCACCTACGGCAAGCTGAC

CCTGAAGTTCATCTGCACCACCGGCAAGCTGCCCGTGCCCTGGCCCACCC

TCGTGACCACCCTGACCTACGGCGTGCAGTGCTTCAGCCGCTACCCCGAC

CACATGAAGCAGCACGACTTCTTCAAGTCCGCCATGCCCGAAGGCTACGT

CCAGGAGCGCACCATCTTCTTCAAGGACGACGGCAACTACAAGACCCGCG

CCGAGGTGAAGTTCGAGGGCGACACCCTGGTGAACCGCATCGAGCTGAAG

GGCATCGACTTCAAGGAGGACGGCAACATCCTGGGGCACAAGCTGGAGTA

CAACTACAACAGCCACAACGTCTATATCATGGCCGACAAGCAGAAGAACG

GCATCAAGGTGAACTTCAAGATCCGCCACAACATCGAGGACGGCAGCGTG

CAGctgcagcactcagactacgtgcacctctgCTGGCCGACCACTACCAG

CAGAACACCCCCATCGGCGACGGCCCCGTGCTGCTGCCCGACAACCACTA

CCTGAGCACCCAGTCCGCCCTGAGCAAAGACCCCAACGAGAAGCGCGATC

ACATGGTCCTGCTGGAGTTCGTGA

Results 24 well transfections were set-up as described above. Each condition was performed in duplicate/triplicate. 24 hrs after transfection the cells were treated with either 2 mM DTT, to induce the UPR, or by mock treatment with an equivalent volume of water. 1, 3, 5 and 24 hrs after treatment of the cells GFP fluorescence was measured as previously described.

Figure 3:
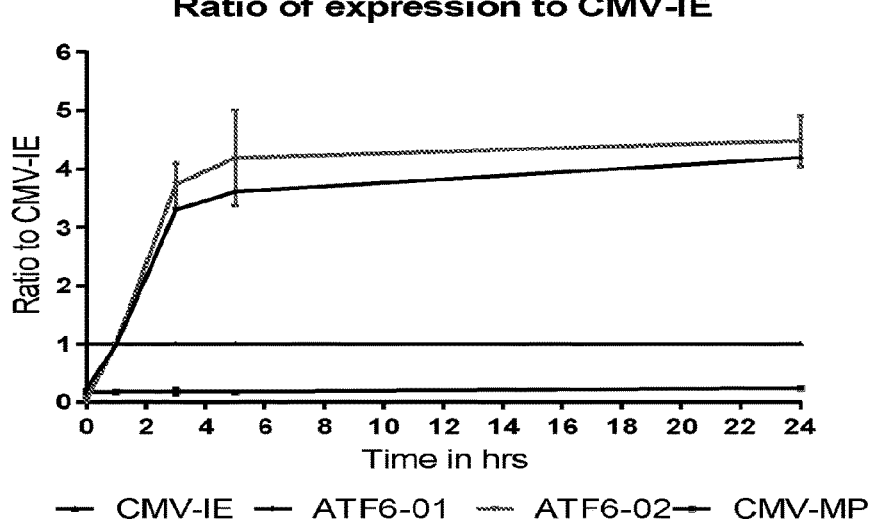
FIG. 3 shows expression of GFP from both plasmids after induction by 2 mM DTT. Figures are ratio to CMV-IE.

The ratio of GFP fluorescence to the control plasmid was calculated before and after induction. FIG. 3 shows the cumulative results of 3 independent experiments.

Figure 4:
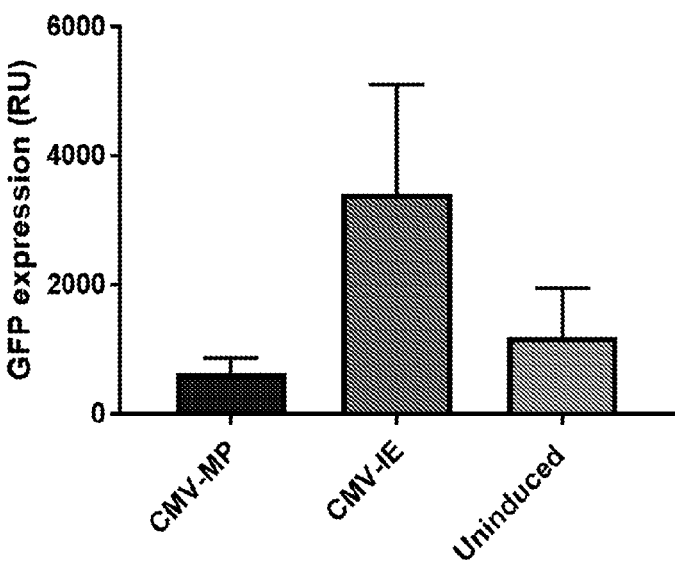
FIG. 4 shows raw data of expression from SYNP-ATF6-01 before and after addition of 2 mM DTT.
Figure 5:
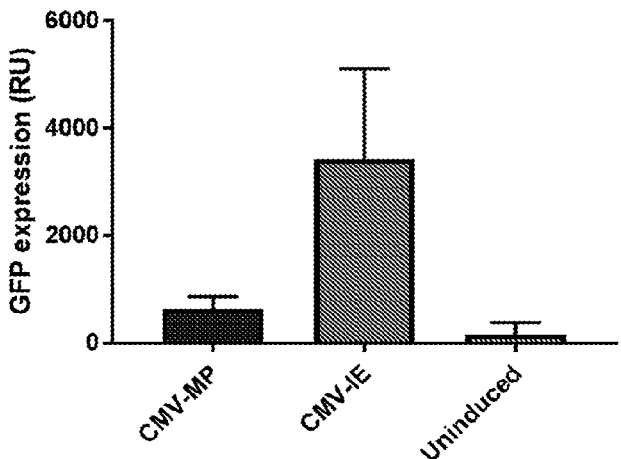
FIG. 5 shows raw data of expression from SYNP-ATF6-02 before and after addition of 2 mM DTT.
Figure 6:
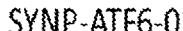
FIG. 6 shows fluorescence microscopy of HEK293F cells transfected with SYNP-ATF6-01 or SYNP-ATF6-02 before and after treatment with 2 mM DTT.
Figure 6:
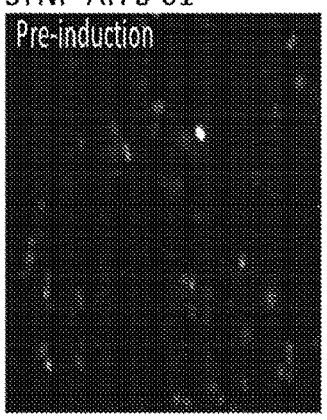
Figure 6:
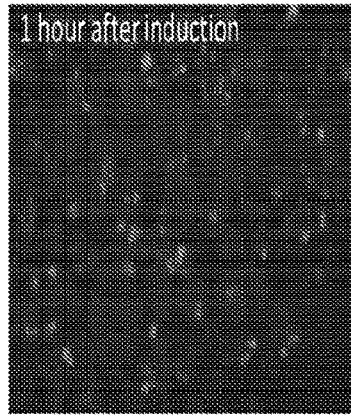
Figure 6:
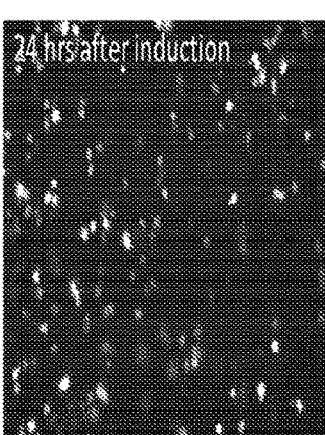
Figure 6:
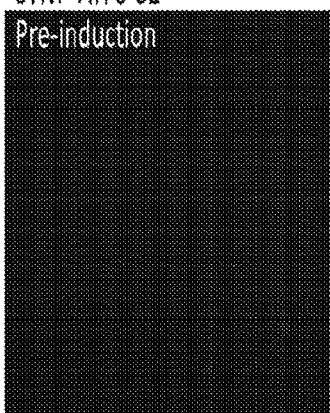
Figure 6:
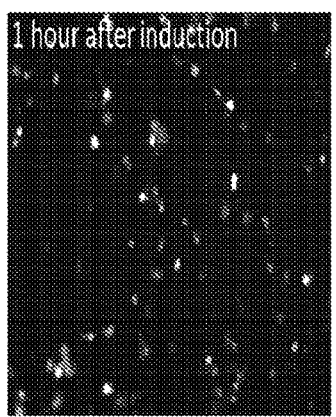
Figure 6:
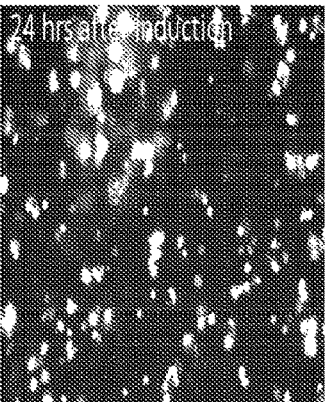

FIG. 3 shows Expression of GFP from both plasmids after induction by 2 mM DTT. Figures are ratio to CMV-IE. This demonstrates that the 6×ATF6 elements are highly inducible by ER-stress, and can enhance gene expression to 3 times the level of CMV-IE. Furthermore, addition of the XBP1 intron to EGFP increases the expression to 4 times the level of CMV-IE. When the raw background data was analysed, it was revealed that SYNP-ATF6-01 had background activity equivalent to CMV-MP and that addition of the intron to EGFP decreases the background level of GFP fluorescence to practically zero (FIGS. 4 and 5). This was confirmed via fluorescence microscopy (FIG. 6). This indicates that a dual-control approach to protein expression provided herein, i.e. transcriptional through the regulatable promoter and translational through the regulatable intron, can provide tight regulated control and high expression levels.

Example 3: Inducible Expression of EGFP from SYNP-ATF6-01 and -02 During wtAAV Production The purpose of this example was to determine whether the ER-stress response could be activated by production of heterologous proteins, as an alternative (or addition) to chemical ER-stress, as used previously. An experiment was performed whereby the GFP expression from SYNP-ATF6-01 and SYNP-ATF6-02 was measured during AAV production.

HEK293F cells were used in this study. All growth conditions, transfections and analyses were carried out as described in Example 1.

Figure 7:
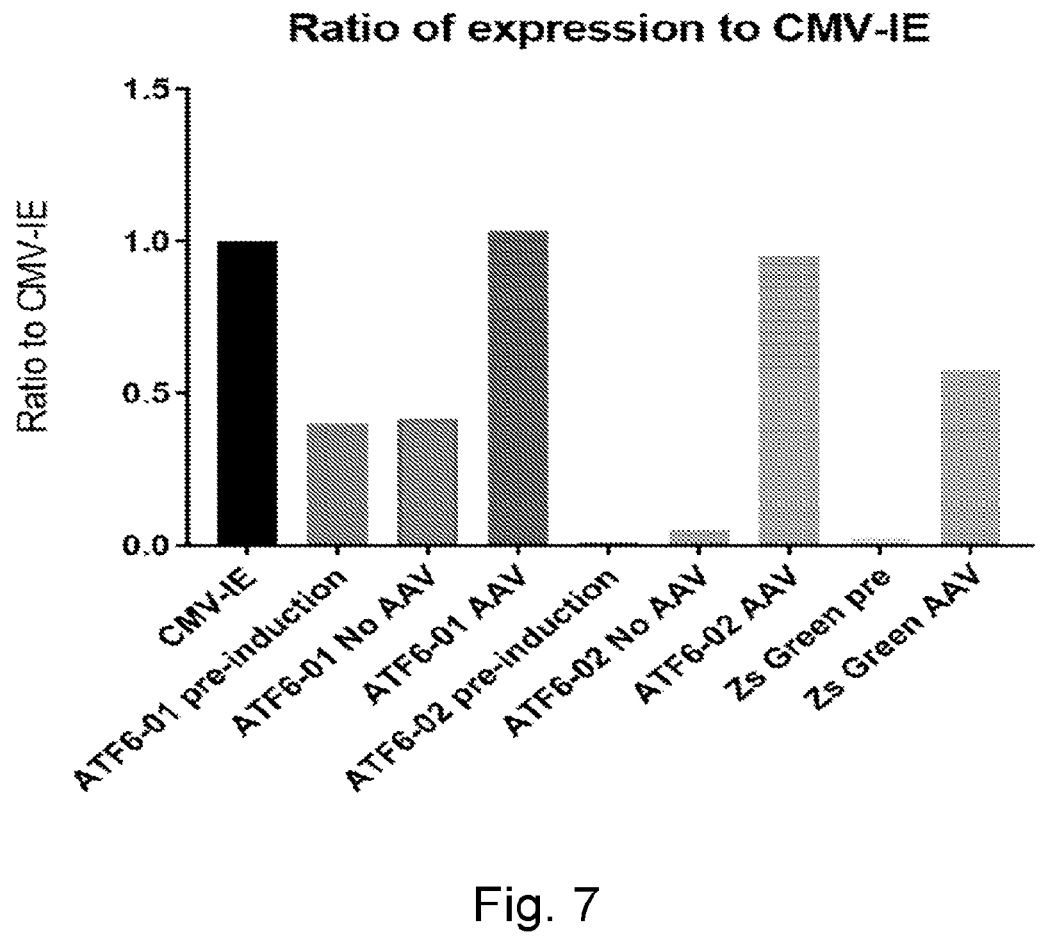
Figure 8:
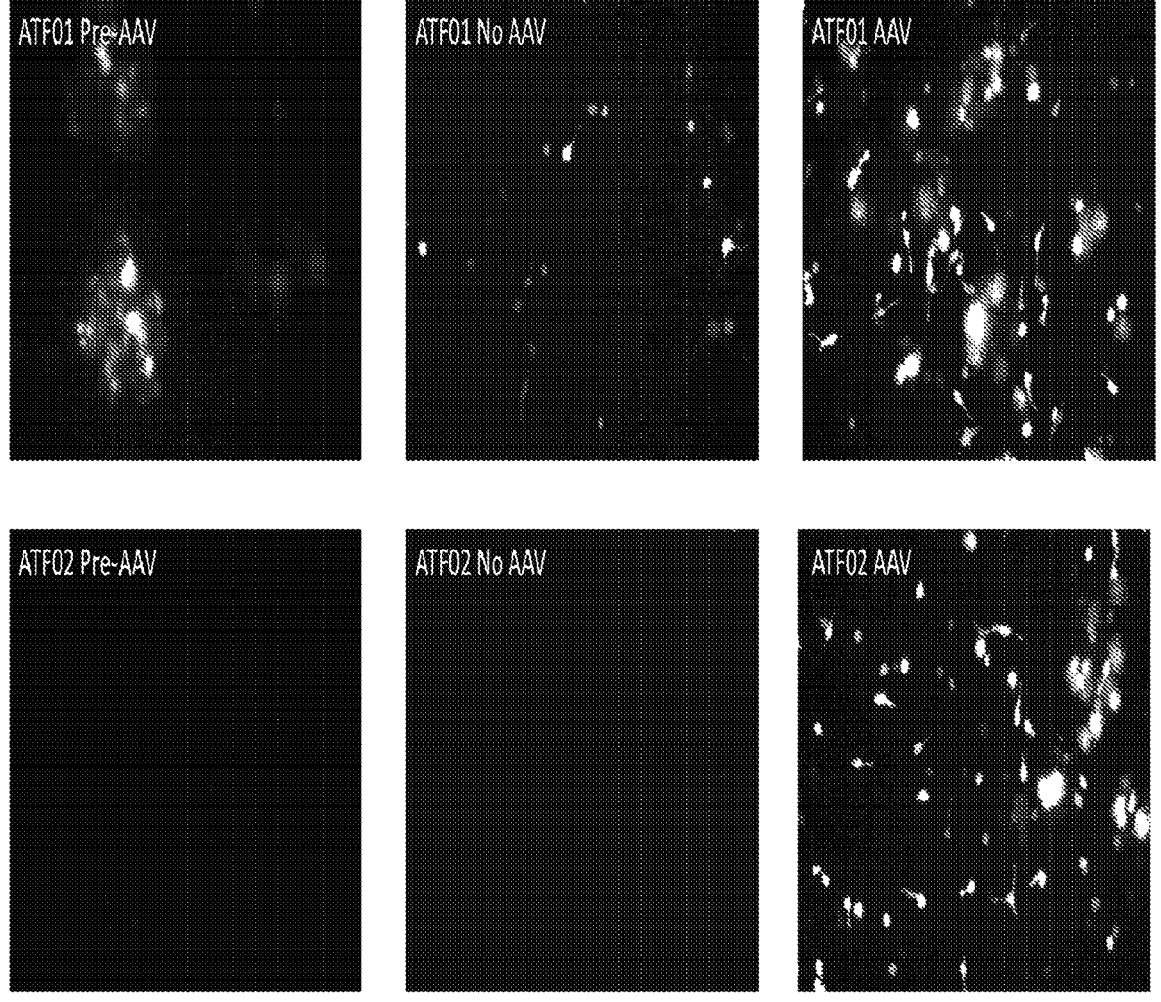
FIG. 8 shows EGFP expression from HEK293F cells before and after wtAAV production.

In this experiment transfections were carried out in 24-well plates as previously described. The ATF6 plasmids (SYNP-ATF6-01 and SYNP-ATF6-02 constructs in the pMA-RQ vector) were transfected into HEK293F cells (using MAX reagent, as above) and after 24 hrs GFP was measured. After GFP measurement the same cells were transfected with the plasmids for wtAAV production pGRG25AAV2 (provided by Adrien Savvy) and pHelper plasmid from Takara/Clonetech in a 1:1 ratio. EGFP fluorescence was then measured after 1, 3, 5 and 24 hrs (FIGS. 7 and 8—not all data is shown). Both plasmids are required for wtAAV production, with the pGRG25AAV2 providing the wtAAV2 genome and the pHelper plasmid providing the E2, VA and E4 helper functions required for virus replication.

The wtAAV2 virus genome is well-known in the art (see Srivastava et al. "Nucleotide sequence and organization of the adeno-associated virus 2 genome", J Virol. 1983 February; 45(2): 555-564), and expression systems for AAV are also well-known in the art. In the present case the wtAAV2 virus genome was inserted into plasmid pGRG25, which is described in McKenzie and Craig, "Fast, easy and efficient: site-specific insertion of transgenes into Enterobacterial chromosomes using Tn7 without need for selection of the insertion event"; BMC Microbiology 2006, 6:39. The pHelper plasmid is available from Takara/Clonetech (catalogue #6234 of the AAVpro system). Suitable AAV2 expression systems for inducing AAV expression are widely commercially available, for example from Takara (Clonetech) as the "AAVpro Helper Free System (AAV2)"—see http://www.clontech.com/US/Products/Viral_Transduction/AAVVectorSystems/Helper_Free_Expression_System.

The plasmid pAAV-CMV-ZsGreen (catalogue #6231 from Takara/Clonetech AAV vector systems) was used as control to confirm AAV expression was achieved in the cells. pAAV-CMV-ZsGreen and pHelper plasmid, in a 1:1 ratio, were transfected into a separate population of HeK293F cells. This confirmed successful AAV expression. Zs green is a variant of eGFP and as such GFP measurement was carried out on these cells as previously described.

These data show that both plasmids can be induced to the level of CMV-IE by production of wtAAV. Furthermore, it can be observed that ATF6-01 has similar background level to previous experiments, whereas the background level of ATF6-02 is zero, and only the synthesis of wtAAV can induce the production of EGFP. This supports our initial findings that both ER-stress elements are required for complete control of expression.

Example 4: Induction of UPR with Various Inducers

Experiments were performed to assess the ability of several candidate agents to induce the UPR. The ability of these candidate inducers to induce UPR was assessed using the techniques essentially as described above. The additional candidates tested were 0.5 mM palmitic acid, 1 uM MF-43 (2-methyl-5-(6-(4-(2-(trifluoromethyl)phenoxy)piperidin-1-yl)pyridazin-3-yl)-1,3,4-thiadiazole), which is an inhibitor of stearoyl-CoA desaturase, and a combination of both of these (for the same concentrations of each was used).

In these experiments transfections were done in 24-well plates as previously described. The SYNP-ATF6-02 plasmid (i.e. SYNP-ATF6-02 in pMA-RQ vector) was transfected into HEK293F cells and after 24 hrs GFP was measured. Induction of the UPR was then stimulated using the aforementioned inducers and samples were taken and measured at 0, 1, 3, 5 and 24 hrs after induction. GFP expression was measured as previously described. Results are the average of 3 individual experiments and the error bars represent the standard deviation.

Experimental procedure in brief:

40 ml of cells were grown in a 250 ml vented Erlenmeyer flask (Sigma-Aldrich CLS431144) at 37° C., 8% $CO_2$ with agitation at 100 rpm. Cells were seeded as described in the manufacturer's instructions.

1 day before transfection cells were counted using a haemocytometer and split to 500,000 cells/ml.

On the day of transfection cells are seeded to 1 million cells/ml in 500 μl of appropriate medium in a 24 well plate.

0.625 μg of DNA/well was then added to 10 μl of OptiMem medium (Thermofisher; 11058021) and incubated for 5 minutes at room temperature.

Concurrently 0.625 μl of Max reagent was made up to 10 μl by addition of OptiMem and incubated for 5 minutes at room temperature.

After this incubation both mixes were added to the same tube and incubated at room temperature for 25-30 minutes.

The DNA/Max reagent mix (20 μl/well) was then added directly to the cells and the cells incubated as described previously.

Cells were then measured for GFP fluorescence after 24 hrs.

Intron splicing from the GFP construct was measured after addition of either 2 mM DTT, 0.5 mM palmitate, 1 μM MF-43, a combination of 0.5 mM palmitate and 1 μM MF-43, and AAV synthesis by monitoring of GFP fluorescence after 1, 3, 5 and 24 hrs.

AAV production on induction of UPR: The ATF6 plasmid (i.e. SYNP-ATF6-02 in pMA-RQ vector) was transfected into HEK293 cells as previously described. 24 hrs later GFP was measured. After GFP measurement the same cells were transfected with the plasmids for wtAAV production pGRG25AAV2 and pHelper plasmid in a 1:1 ratio into the cells, as described above. EGFP fluorescence was then measured after 1, 3, 5 and 24 hrs.

Measurement of GFP Fluorescence

Cell lysis buffer was prepared from the luciferase assay system (Promega; E1500) by diluting 1 in 5 with sterile water.

Cells were pelleted at 900×g for 5 minutes and re-suspended in 100 µl/1×10$^6$ cells of cell lysis buffer from the Luciferase kit.

This was then incubated for 10-15 minutes at room temperature for lysis to occur.

Cellular nuclei and debris was harvested at 900×g for 5 minutes.

The supernatant was collected and a max of 100 µl/sample to a 96 well black plate.

The supernatant was diluted 1 in 2 with PBS (this is to dilute out the mercaptoethanol from the lysis buffer which effects the GFP signal; GFP signal is decreased in the presence of reducing agents).

Sample was incubated for 5 minutes at room temperature.

GFP fluorescence was measured using a plate reader with excitation and emission set at 485 nm and 520 nm respectively.

GFP fluorescence was also visualised directly under a fluorescent microscope.

Figure 9:
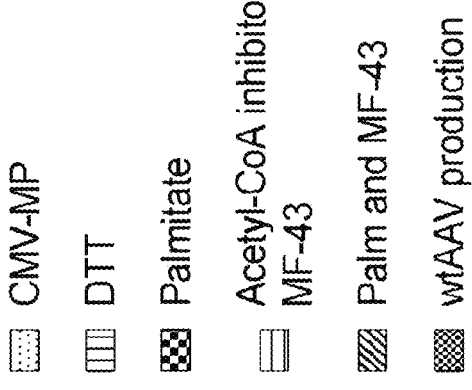
FIG. 9 shows EGFP expression measured as a ratio to CMV-IE. Construct used was SYNP-ATF6-02; contains intron and ATF6 inducible promoter. Transfections were performed on HEK293F cells using Maxcyte reagent. 24 Hrs after transfection the inducers were added and GFP expression followed for the next 24 hrs. Inducer concentrations; DTT 2 mM, Palmitate 0.5 mM, MF-43 1 μM.
Figure 9:
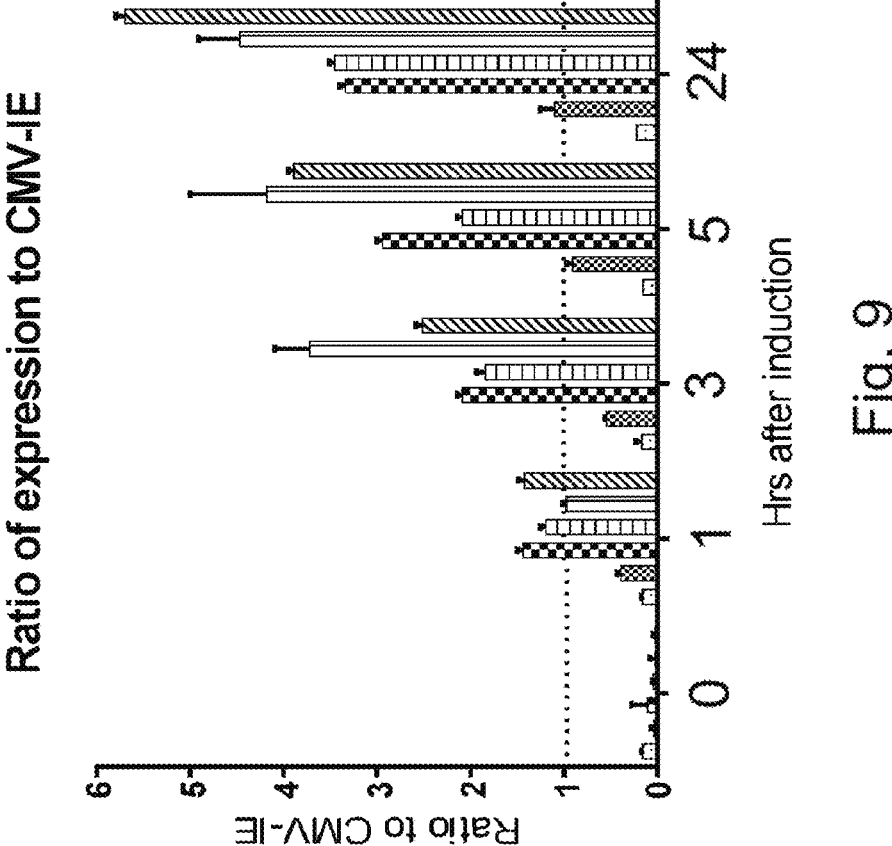

The results of these experiments are shown in FIG. 9, from which it can be seen that all of the agents successfully induced UPR, as indicated by the expression of functional EGFP after addition of the agent. There was a range of the strengths of induction from each of the agents. DTT is a very potent inducer of the UPR. Both palmitate and MF-43, which affect lipid balance in the cells, effectively induced the UPR individually, and when combined the level of induction was more potent. WtAAV production was an effective inducer, but the effect was less strong than the other inducers.

An interesting and potentially useful observation from this experiment is that different inducers can be used to induce the UPR at different levels, thus allowing for control of the level of splicing and this expression of the functional expression product, in this case EGFP. Alternatively, or additionally, different dosage levels of the various agents can be used to adjust the level of expression of the functional expression product.

The procedure set out in this example can be used to assess the ability of any agent to induce the UPR.

Example 5—Use of a Regulatable Intron for Regulation of Expression of Secreted Alkaline Phosphatase (SEAP)

Secreted alkaline phosphatase is a standard protein used in the bioprocessing industry as a marker. It is an ideal marker for secreted proteins as the protein passes through all of the protein quality control (transcription, translation, post-translational modification and then secretion) check-points of cell.

Construction of the SEAP Sequence Including the Regulatable Intron.

Construct SEAP-ATF6-001 was synthesised at GeneART by chemical synthesis

The UPR-inducible cis-regulatory element (enhancer region) used was 6×ATF6 (TGACGTGCT), each ATF6 being spaced by 20 bp, coupled to the CMV-MP. This is a modification of the tandem repeat 6×ATF6 promoter used above, and its sequence underlined in the sequence below.

Intron was engineered between 2 CAG codons at position 1314 of the SEAP coding sequence. The DNA coding for the excised region of the inserted intron was as follows:

```
                                        (SEQ ID NO: 32)
        CAGACGGGCAACTTTACACGACGCTG
```

Including the splice sites this gives rise to the following sequence:

```
                                        (SEQ ID NO: 33)
        CAG/CAGACGGGCAACTTTACACGACGCTG/CAG.
```

This sequence does not lead to the intron secondary structure described for XBP1 wild type intron in the literature (see below in Example 6 for discussion of this point).

The SEAP expression construct sequence, including the promoter and regulatable intron, is as follows (the excised intron sequence is shown in bold, and the 6×ATF6 enhancer region is underlined):

```
                                        (SEQ ID NO: 34)
TGACGTGCTGATGATGCGTAGCTAGTAGTTGACGTGCTGATGATGCGTAG

CTAGTAGTTGACGTGCTGATGATGCGTAGCTAGTAGTTGACGTGCTGATG

ATGCGTAGCTAGTAGTTGACGTGCTGATGATGCGTAGCTAGTAGTTGACG

TGCTGATGATGCGTAGCTAGTAGTGCAGTTAGCGTAGCTGAGGTACCGTC

GACGATATCGGATCCAGGTCTATATAAGCAGAGCTCGTTTAGTGAACCGT

CAGATCGCCTAGATACGCCATCCACGCTGTTTTGACCTCCATAGAAGATC

GCCACCATGCTGCTGCTGCTGCTGCTGGGCCTGAGGCTACAGCTCTC

CCTGGGCATCATCCCAGTTGAGGAGGAGAACCCGGACTTCTGGAACCGCG

AGGCAGCCGAGGCCCTGGGTGCCGCCAAGAAGCTGCAGCCTGCACAGACA

GCCGCCAAGAACCTCATCATCTTCCTGGGCGATGGGATGGGGGTGTCTAC

GGTGACAGCTGCCAGGATCCTAAAAGGGCAGAAGAAGGACAAACTGGGGC

CTGAGATACCCCTGGCTATGGACCGCTTCCCATATGTGGCTCTGTCCAAG

ACATACAATGTAGACAAACATGTGCCAGACAGTGGAGCCACAGCCACGGC

CTACCTGTGCGGGGTCAAGGGCAACTTCCAGACCATTGGCTTGAGTGCAG

CCGCCCGCTTTAACCAGTGCAACACGACACGCGGCAACGAGGTCATCTCC

GTGATGAATCGGGCCAAGAAAGCAGGGAAGTCAGTGGGAGTGGTAACCAC

CACACGAGTGCAGCACGCCTCGCCAGCCGGCACCTACGCCCACACGGTGA

ACCGCAACTGGTACTCGGACGCCGACGTGCCTGCCTCGGCCCGCCAGGAG

GGGTGCCAGGACATCGCTACGCAGCTCATCTCCAACATGGACATTGACGT

GATCCTAGGTGGAGGCCGAAAGTACATGTTTCGCATGGGAACCCCAGACC

CTGAGTACCCAGATGACTACAGCCAAGGTGGGACCAGGCTGGACGGGAAG

AATCTGGTGCAGGAATGGCTGGCGAAGCGCCAGGGTGCCCGGTATGTGTG

GAACCGCACTGAGCTCATGCAGGCTTCCCTGGACCCGTCTGTGACCCATC

TCATGGGCCTCTTTGAGCCTGGAGACATGAAATACGAGATCCACCGAGAC

TCCACACTGGACCCCTCCCTGATGGAGATGACAGAGGCTGCCCTGCGCCT

GCTGAGCAGGAACCCCCGCGGCTTCTTCCTCTTCGTGGAGGGTGGTCGCA
```

-continued

```
TCGACCACGGTCATCATGAAAGCAGGGCTTACCGGGCACTGACTGAAACG

ATCATGTTCGACGACGCCATTGAGAGGGCGGGCCAGCTCACCAGCGAGGA

GGACACGCTGAGCCTCGTCACTGCCGACCACTCCCACGTCTTCTCCTTCG

GAGGCTACCCCCTGCGAGGGAGCTCCATCTTCGGGCTGGCCCCTGGCAAG

GCCCGGGACAGGAAGGCCTACACGGTCCTCCTATACGGAAACGGTCCAGG

CTATGTGCTCAAGGACGGCGCCCGGCCGGATGTTACCGAGAGCGAGAGCG

GGAGCCCCGAGTATCGGCAGCAGACGGGCAACTTTACACGACGCTGCAGT

CAGCAGTGCCCCTGGACGAAGAGACACACGCAGGCGAGGACGTGGCGGTG

TTCGCGCGCGGCCCGCAGGCGCACCTGGTTCACGGCGTGCAGGAGCAGAC

CTTCATAGCGCACGTCATGGCCTTCGCCGCCTGCCTGGAGCCCTACACCG

CCTGCGACCTGGCGCCCCCCGCCGGCACCACCGACGCCGCGCACCCGGGT

TACTCTAGAGTCGGGGCGGCCGGCCGCTTCGAGCAGACATGA
```

Translation of the coding sequence containing the intron leads to the following truncated protein sequence:

```
                                    (SEQ ID NO: 35)
MLLLLLLLGLRLQLSLGIIPVEEENPDFWNREAAEALGAAKKLQPAQTAA

KNLIIFLGDGMGVSTVTAARILKGQKKDKLGPEIPLAMDRFPYVALSKTY

NVDKHVPDSGATATAYLCGVKGNFQTIGLSAAARFNQCNTTRGNEVISVM

NRAKKAGKSVGVVTTTRVQHASPAGTYAHTVNRNWYSDADVPASARQEGC

QDIATQLISNMDIDVILGGGRKYMFRMGTPDPEYPDDYSQGGTRLDGKNL

VQEWLAKRQGARYVWNRTELMQASLDPSVTHLMGLFEPGDMKYEIHRDST

LDPSLMEMTEAALRLLSRNPRGFFLFVEGGRIDHGHHESRAYRALTETIM

FDDAIERAGQLTSEEDTLSLVTADHSHVFSFGGYPLRGSSIFGLAPGKAR

DRKAYTVLLYGNGPGYVLKDGARPDVTESESGSPEYRQQTGNFTRRCSQQ

CPWTKRHTQARTWRCSRAARRRTWFTACRSRPS
```

Removal of the intron allows full translation of the SEAP protein:

```
                                    (SEQ ID NO: 36)
MLLLLLLLGLRLQLSLGIIPVEEENPDFWNREAAEALGAAKKLQPAQTAA

KNLIIFLGDGMGVSTVTAARILKGQKKDKLGPEIPLAMDRFPYVALSKTY

NVDKHVPDSGATATAYLCGVKGNFQTIGLSAAARFNQCNTTRGNEVISVM

NRAKKAGKSVGVVTTTRVQHASPAGTYAHTVNRNWYSDADVPASARQEGC

QDIATQLISNMDIDVILGGGRKYMFRMGTPDPEYPDDYSQGGTRLDGKNL

VQEWLAKRQGARYVWNRTELMQASLDPSVTHLMGLFEPGDMKYEIHRDST

LDPSLMEMTEAALRLLSRNPRGFFLFVEGGRIDHGHHESRAYRALTETIM

FDDAIERAGQLTSEEDTLSLVTADHSHVFSFGGYPLRGSSIFGLAPGKAR

DRKAYTVLLYGNGPGYVLKDGARPDVTESESGSPEYRQQSAVPLDEETHA

GEDVAVFARGPQAHLVHGVQEQTFIAHVMAFAACLEPYTACDLAPPAGTT

DAAHPGYSRVGAAGRFEQT
```

Experiments were performed essentially as described in the above methods, namely, HEK or CHO-s cells were transfected with the aforementioned construct (pMA-RQ)

and incubated for 24 hrs. After this time the activating compound DTT was added at 2 mM final concentration, SEAP activity was then measured at 3, 5 and 24 hrs post-induction.

In more detail:

The protocol for transfection for 24 well plates was as described in Example 1. Thereafter:

Supernatant was measured for SEAP activity after 24 hrs.

Intron splicing from the SEAP construct was measured after addition of either 2 mM DTT by monitoring of SEAP activity after 3, 5 and 24 hrs.

SEAP activity was measured as per manufacturer's instructions, Roche, SEAP reporter gene assay kit, obtained from Sigma-Aldrich, Cat. No. 11 779 842 001.

As can be seen in FIG. 11, before induction there was no SEAP expression. However, upon addition of DTT there was a rapid increase in SEAP activity, indeed after 3 h the level of SEAP activity was similar to CMV-IE (a strong constitutive promoter). This speed of expression is too quick to be accounted for by transcription alone and suggests that mRNA is being made from the leaky promoter and being translated almost immediately by removal of the intron. Indeed, after 24 h the level of expression in both cell types is ~2-fold higher than CMV-IE.

These results indicate that the intron is suitable for use with secreted proteins. Furthermore, it suggests that there is considerable flexibility regarding secondary structures formed by the intron and regarding the central intron sequence that is flanked by the splice site target sequences (i.e. sequence referred to as Xn, as set out above), with the essential factors for successful splicing of the intron from mRNA being the splice site target sequences. The regulatable intron sequence used in this experiment (CAGACGGGCAACUUUACACGACGCUG (SEQ ID NO: 37)) is quite different from the wild type XBP1 intron sequence (CAGCACUCAGACUACGUGCACCUCUG (SEQ ID NO: 23)), yet effective splicing was achieved. Furthermore, as discussed in more detail below, the intron used in this example is not expected to form a secondary structure resembling that formed by the wild type XBP1 intron.

Example 6—Use of a Regulatable Intron for Regulation of Protein Expression Using the Firefly Luciferase Gene It has been asserted in the prior art describes that the secondary structure formed by the XBP1 intron is essential for splicing. However, all the experiments described above have used an intron structure that would not be expected to form such secondary structures, or structures that resemble the wild type XBP1 intron, and yet the performance of the splicing system has been very robust.

Therefore, one aspect of this experiment was to determine the effect of an intron specifically designed to have the secondary structure described in the prior art. Luciferase, an intracellular protein, was selected as the reporter protein, which is also advantageous due to ease of assaying for expression levels.

Construction of the Luciferase Sequence Including the Regulatable Intron.

The expression construct was synthesised at GeneART by chemical synthesis. The enhancer region is 6×ATF6 (TGACGTGCT) spaced by 20 bp coupled to CMV-MP, as described above.

The intron was inserted between a CCG and a CAG codon at position 1447 of the luciferase coding sequence.

The DNA coding for the excised region of the inserted intron sequence was as follows:

(SEQ ID NO: 32)

CAGACGGGCAACTTTACACGACGCTG including splice sites this gives rise to the following sequence:

(SEQ ID NO: 38)

CCG/CAGACGGGCAACTTTACACGACGCTG/CAG

Figures 16A, 16B, 16C, 16D:
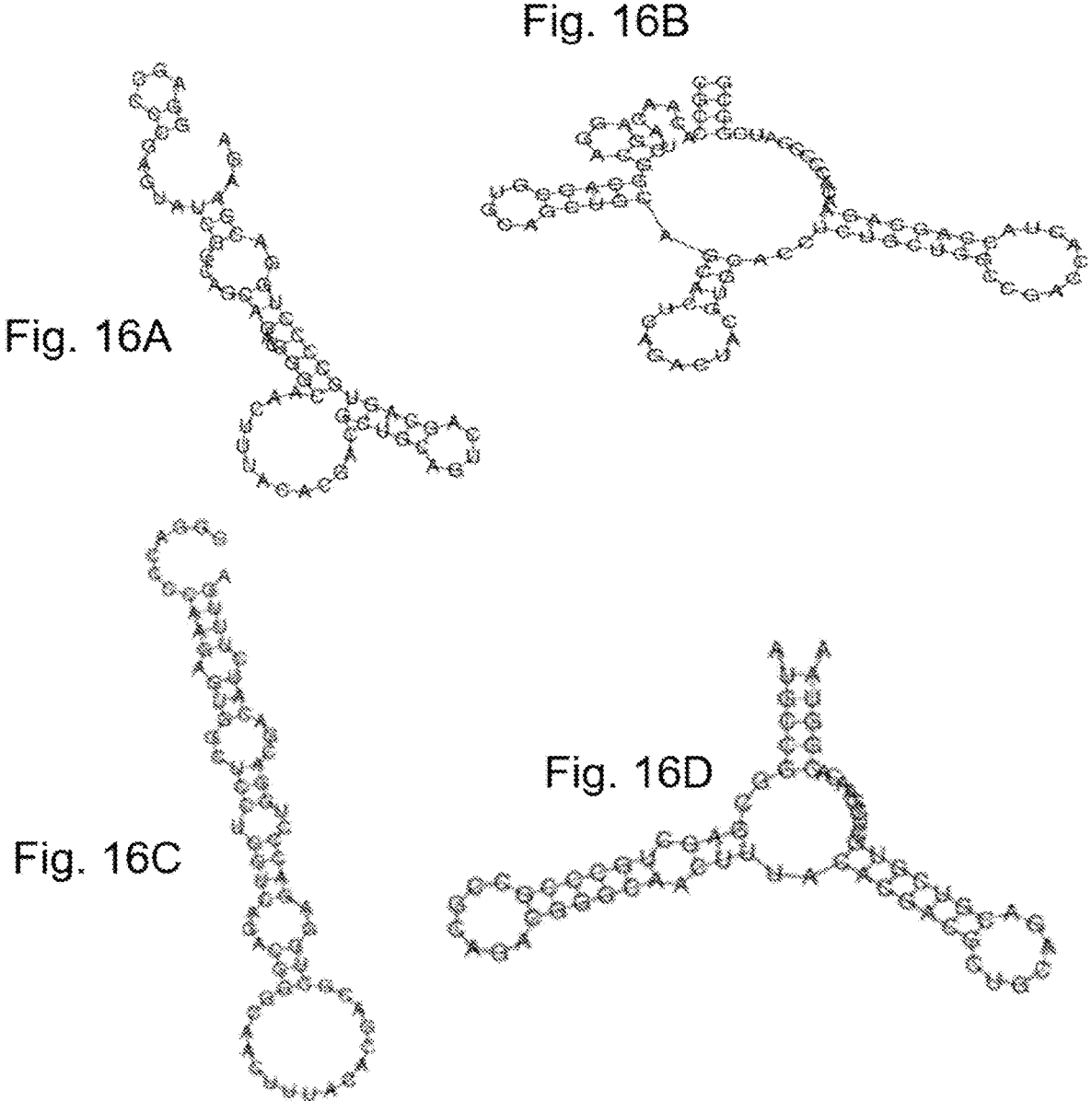

This regulatable intron sequence is predicted to provide the same secondary structure, when inserted into the luciferase gene as described below, as has been described for the XBP1 wild type intron in its native location in the XBP1 gene (calculated using RNA fold web server at http://rna.tbi.univie.ac.at/cgi-bin/RNAWebSuite/RNAfold.cgi). The predicted secondary structure formed by the intron in luciferase is shown in FIG. 16D. For comparison the predicted secondary structures formed by the introns when inserted into the relevant genes as used in other experiments are also shown in FIG. 16:

FIG. 16B - Intron as used in EGFP
(i.e. as used in Examples 1-4, encoded by
CAG/CTGCAGCACTCAGACTACGTGCACCTCTG/CTG,
SEQ ID NO: 48);

FIG. 16A - intron as used in SEAP
(i.e. as used in Example 5, encoded by
CAG/CAGACGGGCAACTTTACACGACGCTG/CAG,
SEQ ID NO: 33);

FIG. 16C - intron as used in CASP9
(i.e. as used in Example 7 encoded by
CAG/CAGACGGGCAACTTTACACGACGCTG/CTG,
SEQ ID NO: 43), see FIG. 16C The luciferase expression construct sequence, including the promoter and regulatable intron, is as follows (the intron sequence is shown in bold, and the 6×ATF6 enhancer region is underlined):

Translation of the coding sequence containing the intron leads to the following truncated protein:

(SEQ ID NO: 39)

MEDAKNIKKGPAPFYPLEDGTAGEQLHKAMKRYALVPGTIAFTDAHIEVD

ITYAEYFEMSVRLAEAMKRYGLNTNHRIVVCSENSLQFFMPVLGALFIGV

AVAPANDIYNERELLNSMGISQPTVVFVSKKGLQKILNVQKKLPIIQKII

IMDSKTDYQGFQSMYTFVTSHLPPGFNEYDFVPESFDRDKTIALIMNSSG

STGLPKGVALPHRTACVRFSHARDPIFGNQIIPDTAILSVVPFHHGFGMF

TTLGYLICGFRVVLMYRFEEELFLRSLQDYKIQSALLVPTLFSFFAKSTL

IDKYDLSNLHEIASGGAPLSKEVGEAVAKRFHLPGIRQGYGLTETTSAIL

ITPEGDDKPGAVGKVVPFFEAKVVDLDTGKTLGVNQRGELCVRGPMIMSG

YVNNPEATNALIDKDGWLHSGDIAYWDEDEHFFIVDRLKSLIKYKGYQVA

PAELESILLQHPNIFDAGVAGLPDDDAGELPAADGQLYTTLQTSCWNTVK

P

Removal of the intron allows translation of the full luciferase protein:

(SEQ ID NO: 40)

MEDAKNIKKGPAPFYPLEDGTAGEQLHKAMKRYALVPGTIAFTDAHIEVD

ITYAEYFEMSVRLAEAMKRYGLNTNHRIVVCSENSLQFFMPVLGALFIGV

AVAPANDIYNERELLNSMGISQPTVVFVSKKGLQKILNVQKKLPIIQKII

IMDSKTDYQGFQSMYTFVTSHLPPGFNEYDFVPESFDRDKTIALIMNSSG

STGLPKGVALPHRTACVRFSHARDPIFGNQIIPDTAILSVVPFHHGFGMF

TTLGYLICGFRVVLMYRFEEELFLRSLQDYKIQSALLVPTLFSFFAKSTL

IDKYDLSNLHEIASGGAPLSKEVGEAVAKRFHLPGIRQGYGLTETTSAIL

ITPEGDDKPGAVGKVVPFFEAKVVDLDTGKTLGVNQRGELCVRGPMIMSG

YVNNPEATNALIDKDGWLHSGDIAYWDEDEHFFIVDRLKSLIKYKGYQVA

PAELESILLQHPNIFDAGVAGLPDDDAGELPAADVVLEHGKTMTEKEIVD

YVASQVTTAKKLRGGVVFVDEVPKGLTGKLDARKIREILIKAKKGGKIAV

Experiments were performed essentially as described in Example 5, namely, HEK or CHO-s cells were transfected with the aforementioned construct and incubated for 24 hrs. After this time the activating compounds DTT or palmitate was added. Luciferase activity was then measured at 3, 5 and 24 h post-induction. Luciferase was measured as follows:

Cell lysis buffer was prepared from the luciferase assay system (Promega; E1500) by diluting 1 in 5 with sterile water.

Cells were pelleted at 900×g for 5 minutes and resuspended in 100 μl/1×10⁶ cells of cell lysis buffer from the Luciferase kit.

This was then incubated for 10-15 minutes at room temperature for lysis to occur.

Cellular nuclei and debris was harvested at 900×g for 5 minutes.

The supernatant was collected, and 10 μl/sample was added to a 96 well white plate.

Bioluminescence was measured using a plate reader using an autoinjector and 50 μl of substrate was injected. Substrate was prepared as per manufacturer's instructions (Promega; E1500).

As can be seen in FIGS. 12a and 12b, before induction there was no luciferase expression, however upon addition of either inducer there was a rapid increase in activity, indeed after 3 hrs the level of luciferase activity was 2-2.5× that of CMV-IE (a strong constitutive promoter). This speed of expression is, again, too rapid to be accounted for by transcription alone and suggests that some mRNA is being already made from the promoter and being translated almost immediately after removal of the intron following induction. Indeed, after 24 hrs the level of expression in both cell types is ~3-4-fold higher than CMV-IE.

These results are somewhat suggestive that the "perfect" intron secondary structure might give better induction levels or higher splicing efficiencies in some cases. However, the structure is clearly unimportant for overall function of the system. Furthermore, SEAP and luciferase are quite different proteins and a straightforward comparison is impossible; SEAP is secreted and therefore undergoes further modifications and another bottleneck for expression.

Example 7—Control of Caspase 9 Gene Expression Using a Regulatable Intron

This experiment was performed to confirm that expression control from the regulatable intron was suitably tight to control expression of toxic expression products that are lethal to the cells expressing them. The regulatable intron was engineered into the apoptosis causing protein caspase 9. Overexpression of this protein in HEK cells causes rapid death. Therefore, any expression of this protein from the unmodified sequence leads to a significant increase in the dead cells within a culture. This allows us to determine the tightness of control afforded by the intron. Caspase 9 was also fused to GFP-Spark which would not be visible if the intron was present in the transcript.

Construction of the Luciferase Sequence Including the Regulatable Intron.

For expression the intron was coupled with the CMV-IE constitutive promoter. The intron construct was cloned into the plasmid vector SYNP-CASPSp-001 using the BsaI restriction site and 2 complimentary oligos. The plasmid was digested with BsaI (NEB R0535S) and the oligos annealed by heating to 98° C. for 5 mins, to melt the secondary structures, and then incubating at 55° C. for 20 minutes. This allowed the oligos to form double stranded DNA. This DNA was designed with overhangs at both the 5' and 3' ends that would allow ligation to the digested SYNP-CASPSp-001. The double stranded DNA was then ligated into the plasmid and subsequently transformed into one shot top ten chemically competent cells (Thermofisher, C404003). Isolated DNA was sequenced to confirm the presence of the intron.

Figure 13:
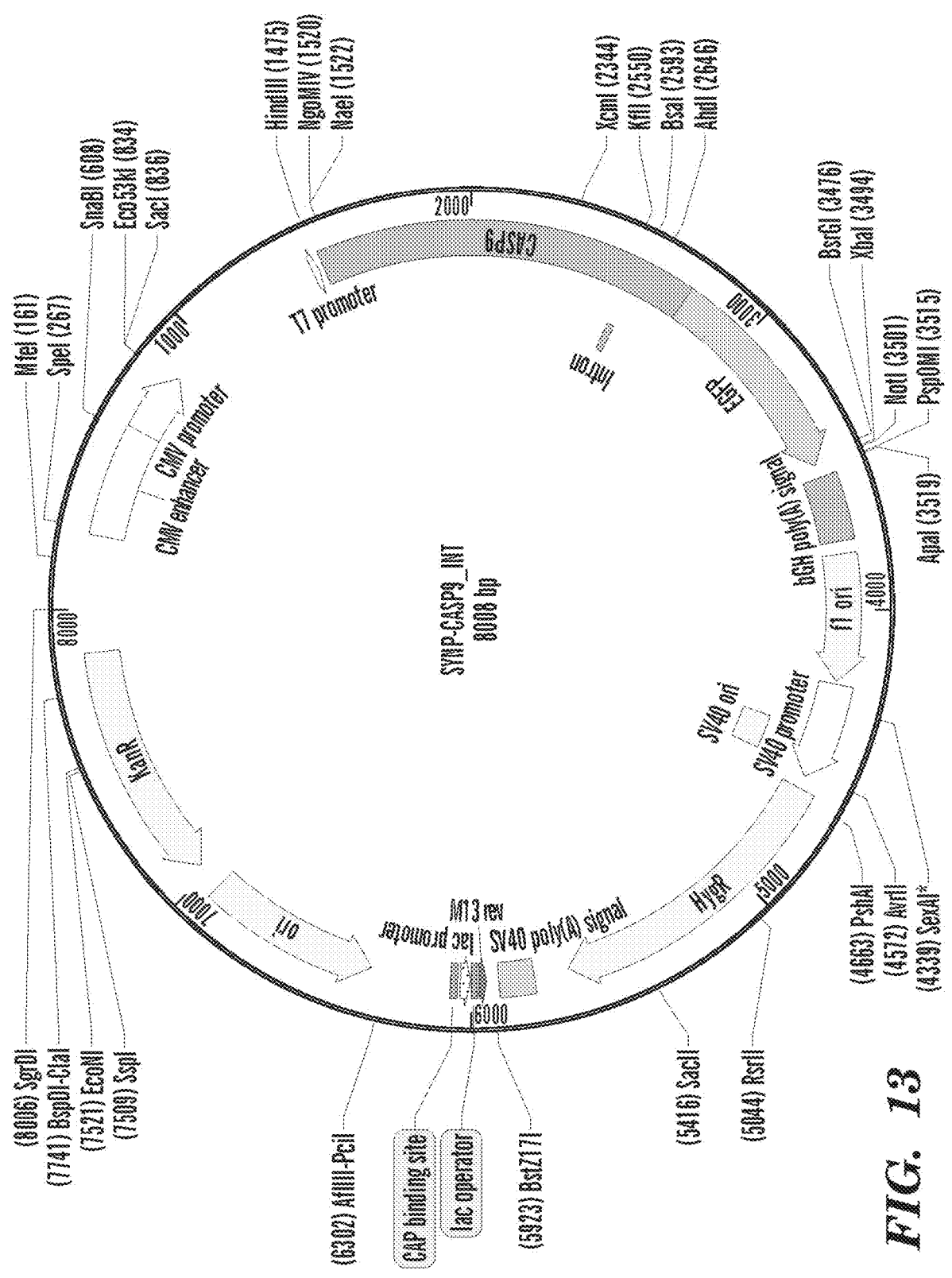
FIG. 13 shows a plasmid map of SYNP-CAS9_INT.

The complete plasmid was referred to as SYNP-CASP9-INT, and a plasmid map is shown in FIG. 13.

The intron oligos added into the vector had the following sequences:

```
INTC9FP:
                                    (SEQ ID NO: 41)
ACGTCAGACGGGCAACTTTACACGACGCTG

INTC9RP:
                                    (SEQ ID NO: 42)
ACGTCAGCGTCGTGTAAAGTTGCCCGTCTG
```

The regulatable intron was thus engineered between an added CCAG and a CTG codon at position 1087 of the Caspase 9 coding sequence.

The DNA coding for the excised region of the inserted intron sequence was as follows:

```
                                    (SEQ ID NO: 32)
        CAGACGGGCAACTTTACACGACGCTG
```

Including splice sites this gives rise to the following sequence:

```
                                    (SEQ ID NO: 43)
    CAG/CAGACGGGCAACTTTACACGACGCTG/CTG
```

This sequence does not lead to the "perfect" intron secondary structure described for XBP1 wild type intron.

The SYNP-CASP9-INT vector including the CASP9-Intron construct sequence, is as follows (the intron sequence is shown in bold):

```
                                                       (SEQ ID NO: 44)
GACGGATCGGGAGATCTCCCGATCCCCTATGGTGCACTCTCAGTACAATCTGCTCTGATGCCGCATAG

TTAAGCCAGTATCTGCTCCCTGCTTGTGTGTTGGAGGTCGCTGAGTAGTGCGCGAGCAAAATTTAAGC

TACAACAAGGCAAGGCTTGACCGACAATTGCATGAAGAATCTGCTTAGGGTTAGGCGTTTTGCGCTGC

TTCGCGAGTACATTTATATTGGCTCATGTCCAATATGACCGCCATGTTGACATTGATTATTGACTAGT

TATTAATAGTAATCAATTACGGGGTCATTAGTTCATAGCCCATATATGGAGTTCCGCGTTACATAACT

TACGGTAAATGGCCCGCCTGGCTGACCGCCCAACGACCCCCGCCCATTGACGTCAATAATGACGTATG

TTCCCATAGTAACGCCAATAGGGACTTTCCATTGACGTCAATGGGTGGAGTATTTACGGTAAACTGCC

CACTTGGCAGTACATCAAGTGTATCATATGCCAAGTCCGCCCCCTATTGACGTCAATGACGGTAAATG

GCCCGCCTGGCATTATGCCCAGTACATGACCTTACGGGACTTTCCTACTTGGCAGTACATCTACGTAT

TAGTCATCGCTATTACCATGGTGATGCGGTTTTGGCAGTACACCAATGGGCGTGGATAGCGGTTTGAC

TCACGGGGATTTCCAAGTCTCCACCCCATTGACGTCAATGGGAGTTTGTTTTGGCACCAAAATCAACG

GGACTTTCCAAAATGTCGTAATAACCCCGCCCCGTTGACGCAAATGGGCGGTAGGCGTGTACGGTGGG

AGGTCTATATAAGCAGAGCTCGTTTAGTGAACCGTCAGATCCTCACTCTCTTCCGCATCGCTGTCTGC

GAGGGCCAGCTGTTGGGCTCGCGGTTGAGGACAAACTCTTCGCGGTCTTTCCAGTACTCTTGGATCGG

AAACCCGTCGGCCTCCGAACGGTACTCCGCCACCGAGGGACCTGAGCGAGTCCGCATCGACCGGATCG

GAAAACCTCTCGAGAAAGGCGTCTAACCAGTCACAGTCGCAAGGTAGGCTGAGCACCGTGGCGGGCGG

CAGCGGGTGGCGGTCGGGGTTGTTTCTGGCGGAGGTGCTGCTGATGATGTAATTAAAGTAGGCGGTCT

TGAGACGGCGGATGGTCGAGGTGAGGTGTGGGTTTAGTGAACCGTCAGATCCTCACTCTCTTCCGCAT

CGCTGTCTGCGAGGGCCAGCTGTCAGGCTTGAGATCCAGCTGTTGGGGTGAGTACTCCCTCTCAAAAG

CGGGCATTACTTCTGCGCTAAGATTGTCAGTTTCCAAAAACGAGGAGGATTTGATATTCACCTGGCCC
```

-continued

```
GATCTGGCCATACACTTGAGTGACAATGACATCCACTTTGCCTTTCTCTCCACAGGTGTCCACTCCCA

GGTCCAAGTTTAAACTTTAATACGACTCACTATAGGGGCCGCCACCAAGCTTGGTACATGGACGAAGC

GGATCGGCGGCTCCTGCGGCGGTGCCGGCTGCGGCTGGTGGAAGAGCTGCAGGTGGACCAGCTCTGGG

ACGCCCTGCTGAGCCGCGAGCTGTTCAGGCCCCATATGATCGAGGACATCCAGCGGGCAGGCTCTGGA

TCTCGGCGGGATCAGGCCAGGCAGCTGATCATAGATCTGGAGACTCGAGGGAGTCAGGCTCTTCCTTT

GTTCATCTCCTGCTTAGAGGACACAGGCCAGGACATGCTGGCTTCGTTTCTGCGAACTAACAGGCAAG

CAGCAAAGTTGTCGAAGCCAACCCTAGAAAACCTTACCCCAGTGGTGCTCAGACCAGAGATTCGCAAA

CCAGAGGTTCTCAGACCGGAAACACCCAGACCAGTGGACATTGGTTCTGGAGGATTCGGTGATGTCGG

TGCTCTTGAGAGTTTGAGGGGAAATGCAGATTTGGCTTACATCCTGAGCATGGAGCCCTGTGGCCACT

GCCTCATTATCAACAATGTGAACTTCTGCCGTGAGTCCGGGCTCCGCACCCGCACTGGCTCCAACATC

GACTGTGAGAAGTTGCGGCGTCGCTTCTCCTCGCTGCATTTCATGGTGGAGGTGAAGGGCGACCTGAC

TGCCAAGAAAATGGTGCTGGCTTTGCTGGAGCTGGCGCAGCAGGACCACGGTGCTCTGGACTGCTGCG

TGGTGGTCATTCTCTCTCACGGCTGTCAGGCCAGCCACCTGCAGTTCCCAGGGGCTGTCTACGGCACA

GATGGATGCCCTGTGTCGGTCGAGAAGATTGTGAACATCTTCAATGGGACCAGCTGCCCCAGCCTGGG

AGGGAAGCCCAAGCTCTTTTTTCATCCAGGCCTGTGGTGGGGAGCAGAAAGACCATGGGTTTGAGGTGG

CCTCCACTTCCCCTGAAGACGAGTCCCCTGGCAGTAACCCCGAGCCAGATGCCACCCCGTTCCAGGAA

GGTTTGAGGACCTTCGACCAGCTGGACGCCATATCTAGTTTGCCCACACCCAGTGACATCTTTGTGTC

CTACTCTACTTTCCCAGGTTTTGTTTCCTGGAGGGACCCCAAGAGTGGCTCCTGGTCAGACGGGCAAC

TTTACACGACGCTGGAGACCCTGGACGACATCTTTGAGCAGTGGGCTCACTCTGAAGACCTGCAGTCC

CTCCTGCTTAGGGTCGCTAATGCTGTTTCGGTGAAAGGGATTTATAAACAGATGCCTGGTTGCTTTAA

TTTCCTCCGAAAAAAACTTTTCTTTAAAACATCAGGGGGTGGAGGCTCTGTGAGCAAGGGCGAGGAGC

TGTTCACCGGGGTGGTGCCCATCCTGGTCGAGCTGGACGGCGACGTAAACGGCCACAAGTTCAGCGTG

TCCGGCGAGGGCGAGGGCGATGCCACCTACGGCAAGCTGACCCTGAAGTTCATCTGCACCACCGGCAA

GCTGCCCGTGCCCTGGCCCACCCTCGTGACCACCCTGACCTACGGCGTGCAGTGCTTCAGCCGCTACC

CCGACCACATGAAGAAGCACGACTTCTTCAAGTCCGCCATGCCCGAAGGCTACGTCCAGGAGCGCACC

ATCTTCTTCAAGGACGACGGCAACTACAAGACCCGCGCCGAGGTGAAGTTCGAGGGCGACACCCTGGT

GAACCGCATCGAGCTGAAGGGCATCGACTTCAAGGAGGACGGCAACATCCTGGGGCACAAGCTGGAGT

ACAACTACAACAGCCACAACGTCTATATCATGGCCGACAAGCAGAAGAACGGCATCAAGGCTAACTTC

AAGGTTCGCCACAACATCGAGGACGGCAGCGTGCAGCTCGCCGACCACTACCAGCAGAACACCCCCAT

CGGCGACGGCCCCGTGCTGCTGCCCGACAACCACTACCTGAGCACCCAGTCCGCCCTGAGCAAAGACC

CCAACGAGAAGCGCGATCACATGGTCCTGCTGGAGTTCGTGACCGCCGCCGGGATCACTCTCGGCATG

GACGAGCTGTACAAGTAAACTCGAGTCTAGAGCGGCCGCCGAATTCGGGCCCGTTTAAACCCGCTGAT

CAGCCTCGACTGTGCCTTCTAGTTGCCAGCCATCTGTTGTTTGCCCCTCCCCCGTGCCTTCCTTGACC

CTGGAAGGTGCCACTCCCACTGTCCTTTCCTAATAAAATGAGGAAATTGCATCGCATTGTCTGAGTAG

GTGTCATTCTATTCTGGGGGGTGGGGTGGGGCAGGACAGCAAGGGGGAGGATTGGGAAGACAATAGCA

GGCATGCTGGGGATGCGGTGGGCTCTATGGCTTCTGAGGCGGAAAGAACCAGCTGGGGCTCTAGGGGG

TATCCCCACGCGCCCTGTAGCGGCGCATTAAGCGCGGCGGGTGTGGTGGTTACGCGCAGCGTGACCGC

TACACTTGCCAGCGCCCTAGCGCCCGCTCCTTTCGCTTTCTTCCCTTCCTTTCTCGCCACGTTCGCAG

GCTTTCCCCGTCAAGCTCTAAATCGGGGGCTCCCTTTAGGGTTCCGATTTAGTGCTTTACGGCACCTC

GACCCCAAAAAACTTGATTAGGGTGATGGTTCACGTAGTGGGCCATCGCCCTGATAGACGGTTTTTCG
```

-continued

```
CCCTTTGACGTTGGAGTCCACGTTCTTTAATAGTGGACTCTTGTTCCAAACTGGAACAACACTCAACC

CTATCTCGGTCTATTCTTTTGATTTATAAGGGATTTTGCCGATTTCGGCCTATTGGTTAAAAAATGAG

CTGATTTAACAAAAATTTAACGCGAATTAATTCTGTGGAATGTGTGTCAGTTAGGGTGTGGAAAGTCC

CCAGGCTCCCCAGCAGGCAGAAGTATGCAAAGCATGCATCTCAATTAGTCAGCAACCAGGTGTGGAAA

GTCCCCAGGCTCCCCAGCAGGCAGAAGTATGCAAAGCATGCATCTCAATTAGTCAGCAACCATAGTCC

CGCCCCTAACTCCGCCCATCCCGCCCCTAACTCCGCCCAGTTCCGCCCATTCTCCGCCCCATGGCTGA

CTAATTTTTTTTATTTATGCAGAGGCCGAGGCCGCCTCTGCCTCTGAGCTATTCCAGAAGTAGTGAGG

AGGCTTTTTTGGAGGCCTAGGCTTTTGCAAAAAGCTCTCGGGAGCTTGTATATCCATTTTCGGATCTG

ATCAGCACGTGATGAAAAAGCCTGAACTCACCGCGACGTCTGTCGAGAAGTTTCTGATCGAAAAGTTC

GACAGCGTCTCCGACCTGATGCAGCTCTCGGAGGGCGAAGAATCTCGTGCTTTCAGCTTCGATGTAGG

AGGGCGTGGATATGTCCTGCGGGTAAATAGCTGCGCCGATGGTTTCTACAAAGATCGTTATGTTTATC

GGCACTTTGCATCGGCCGCGCTCCCGATTCCGGAAGTGCTTGACATTGGGGAATTCAGCGAGAGCCTG

ACCTATTGCATCTCCCGCCGTGCACAGGGTGTCACGTTGCAAGACCTGCCTGAAACCGAACTGCCCGC

TGTTCTGCAGCCGGTCGCGGAGGCCATGGATGCGATCGCTGCGGCCGATCTTAGCCAGACGAGCGGGT

TCGGCCCATTCGGACCGCAAGGAATCGGTCAATACACTACATGGCGTGATTTCATATGCGCGATTGCT

GATCCCCATGTGTATCACTGGCAAACTGTGATGGACGACACCGTCAGTGCGTCCGTCGCGCAGGCTCT

CGATGAGCTGATGCTTTGGGCCGAGGACTGCCCCGAAGTCCGGCACCTCGTGCACGCGGATTTCGGCT

CCAACAATGTCCTGACGGACAATGGCCGCATAACAGCGGTCATTGACTGGAGCGAGGCGATGTTCGGG

GATTCCCAATACGAGGTCGCCAACATCTTCTTCTGGAGGCCGTGGTTGGCTTGTATGGAGCAGCAGAC

GCGCTACTTCGAGCGGAGGCATCCGGAGCTTGCAGGATCGCCGCGGCTCCGGGCGTATATGCTCCGCA

TTGGTCTTGACCAACTCTATCAGAGCTTGGTTGACGGCAATTTCGATGATGCAGCTTGGGCGCAGGGT

CGATGCGACGCAATCGTCCGATCCGGAGCCGGGACTGTCGGGCGTACACAAATCGCCCGCAGAAGCGC

GGCCGTCTGGACCGATGGCTGTGTAGAAGTACTCGCCGATAGTGGAAACCGACGCCCCAGCACTCGTC

CGAGGGCAAAGGAATAGCACGTGCTACGAGATTTCGATTCCACCGCCGCCTTCTATGAAAGGTTGGGC

TTCGGAATCGTTTTCCGGGACGCTGGCTGGATGATCCTCCAGCGCGGGGATCTCATGCTGGAGTTCTT

CGCCCACCCCAACTTGTTTATTGCAGCTTATAATGGTTACAAATAAAGCAATAGCATCACAAATTTCA

CAAATAAAGCATTTTTTTCACTGCATTCTAGTTGTGGTTTGTCCAAACTCATCAATGTATCTTATCAT

GTCTGTATACCGTCGACCTCTAGCTAGAGCTTGGCGTAATCATGGTCATAGCTGTTTCCTGTGTGAAA

TTGTTATCCGCTCACAATTCCACACAACATACGAGCCGGAAGCATAAAGTGTAAAGCCTGGGGTGCCT

AATGAGTGAGCTAACTCACATTAATTGCGTTGCGCTCACTGCCCGCTTTCCAGTCGGGAAACCTGTCG

TGCCAGCTGCATTAATGAATCGGCCAACGCGCGGGGAGAGGCGGTTTGCGTATTGGGCGCTCTTCCGC

TTCCTCGCTCACTGACTCGCTGCGCTCGGTCGTTCGGCTGCGGCGAGCGGTATCAGCTCACTCAAAGG

CGGTAATACGGTTATCCACAGAATCAGGGGATAACGCAGGAAAGAACATGTGAGCAAAAGGCCAGCAA

AAGGCCAGGAACCGTAAAAAGGCCGCGTTGCTGGCGTTTTTCCATAGGCTCCGCCCCCCTGACGAGCA

TCACAAAAATCGACGCTCAAGTCAGAGGTGGCGAAACCCGACAGGACTATAAAGATACCAGGCGTTTC

CCCCTGGAAGCTCCCTCGTGCGCTCTCCTGTTCCGACCCTGCCGCTTACCGGATACCTGTCCGCCTTT

CTCCCTTCGGGAAGCGTGGCGCTTTCTCATAGCTCACGCTGTAGGTATCTCAGTTCGGTGTAGGTCGT

TCGCTCCAAGCTGGGCTGTGTGCACGAACCCCCCGTTCAGCCCGACCGCTGCGCCTTATCCGGTAACT

ATCGTCTTGAGTCCAACCCGGTAAGACACGACTTATCGCCACTGGCAGCAGCCACTGGTAACAGGATT

AGCAGAGCGAGGTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGTTGGTAGCTCTT
```

-continued

```
GATCCGGCAAACAAACCACCGCTGGTAGCGGTGGTTTTTTTGTTTGCAAGCAGCAGATTACGCGCAGA

AAAAAAGGATCTCAAGAAGATCCTTTGATCTTTTCTACGGGGTCTGAGCGCGGAACCCCTATTTGTTT

ATTTTTCTAAATACATTCAAATATGTATCCGCTCATGAATTAATTCTTAGAAAAACTCATCGAGCATC

AAATGAAACTGCAATTTATTCATATCAGGATTATCAATACCATATTTTTGAAAAAGCCGTTTCTGTAA

TGAAGGAGAAAACTCACCGAGGCAGTTCCATAGGATGGCAAGATCCTGGTATCGGTCTGCGATTCCGA

CTCGTCCAACATCAATACAACCTATTAATTTCCCCTCGTCAAAAATAAGGTTATCAAGTGAGAAATCA

CCATGAGTGACGACTGAATCCGGTGAGAATGGCAAAAGTTTATGCATTTCTTTCCAGACTTGTTCAAC

AGGCCAGCCATTACGCTCGTCATCAAAATCACTCGCATCAACCAAACCGTTATTCATTCGTGATTGCG

CCTGAGCGAGACGAAATACGCGATCGCTGTTAAAAGGACAATTACAAACAGGAATCGAATGCAACCGG

CGCAGGAACACTGCCAGCGCATCAACAATATTTTCACCTGAATCAGGATATTCTTCTAATACCTGGAA

TGCTGTTTTCCCAGGGATCGCAGTGGTGAGTAACCATGCATCATCAGGAGTACGGATAAAATGCTTGA

TGGTCGGAAGAGGCATAAATTCCGTCAGCCAGTTTAGTCTGACCATCTCATCTGTAACATCATTGGCA

ACGCTACCTTTGCCATGTTTCAGAAACAACTCTGGCGCATCGGGCTTCCCATACAATCGATAGATTGT

CGCACCTGATTGCCCGACATTATCGCGAGCCCATTTATACCCATATAAATCAGCATCCATGTTGGAAT

TTAATCGCGGCCTAGAGCAAGACGTTTCCCGTTGAATATGGCTCATAACACCCCTTGTATTACTGTTT

ATGTAAGCAGACAGTTTTATTGTTCATGACCAAAATCCCTTAACGTGAGTTTTCGTTCCACTGAGCGT

CAGACCCCGTAGAAATCCGCGCACATTTCCCCGAAAAGTGCCACCTGACGTC
```

The coding sequence containing the intron leads to the following truncated protein:

(SEQ ID NO: 45)

```
MDEADRRLLRRCRLRLVEELQVDQLWDALLSRELFRPHMIEDIQRAGS

GSRRDQARQLIIDLETRGSQALPLFISCLEDTGQDMLASFLRTNRQAA

KLSKPTLENLTPVVLRPEIRKPEVLRPETPRPVDIGSGGFGDVGALES

LRGNADLAYILSMEPCGHCLIINNVNFCRESGLRIRTGSNIDCEKLRR

RFSSLHFMVEVKGDLTAKKMVLALLELAQQDHGALDCCVVVILSHGCQ

ASHLQFPGAVYGTDGCPVSVEKIVNIFNGTSCPSLGGKPKLFFIQACG

GEQKDHGFEVASTSPEDESPGSNPEPDATPFQEGLRTFDQLDAISSLP

TPSDIFVSYSTFPGFVSWRDPKSGSWSAGDPGRHL
```

Removal of the intron allows full translation of the Caspase 9 protein:

(SEQ ID NO: 46)

```
MDEADRRLLRRCRLRLVEELQVDQLWDALLSRELFRPHMIEDIQRAGS

GSRRDQARQLIIDLETRGSQALPLFISCLEDTGQDMLASFLRTNRQAA

KLSKPTLENLTPVVLRPEIRKPEVLRPETPRPVDIGSGGFGDVGALES

LRGNADLAYILSMEPCGHCLIINNVNFCRESGLRIRTGSNIDCEKLRR

RFSSLHFMVEVKGDLTAKKMVLALLELAQQDHGALDCCVVVILSHGCQ

ASHLQFPGAVYGTDGCPVSVEKIVNIFNGTSCPSLGGKPKLFFIQACG

GEQKDHGFEVASTSPEDESPGSNPEPDATPFQEGLRTFDQLDAISSLP

TPSDIFVSYSTFPGFVSWRDPKSGSWSADGQLYTTLLEILDDIFEQWA

HSEDLQSLLLRVANAVSVKGIYKQMPGCFNFLRKKLFFKTSGGGGS
```

Transfection was performed as previously described. DTT was added at 2 mM and forskolin was added at 10 µM. The latter was carried out to determine whether forskolin could induce the removal of the intron. Amongst other things, forskolin has potential gene therapy applications. Induction of intron removal was measured as function of cell death, with higher cell death an indicator of removal of the intron.

Experiments were performed as described in the methods namely, HEK or CHO-s cells were transfected with the aforementioned construct and incubated for 24 h. After this time the activating compound DTT or Forskolin was added, % cell death was then measured at 3, 5 and 24 h post-induction.

Induction of intron was measured as function of cell death, using the Countess II cell counter (Thermofisher). Cells were stained with trypan blue to ascertain cell viability. 10 µl of cell suspension was added to a Haemocytomer and analysed on the countess.

Figures 14A, 14B:
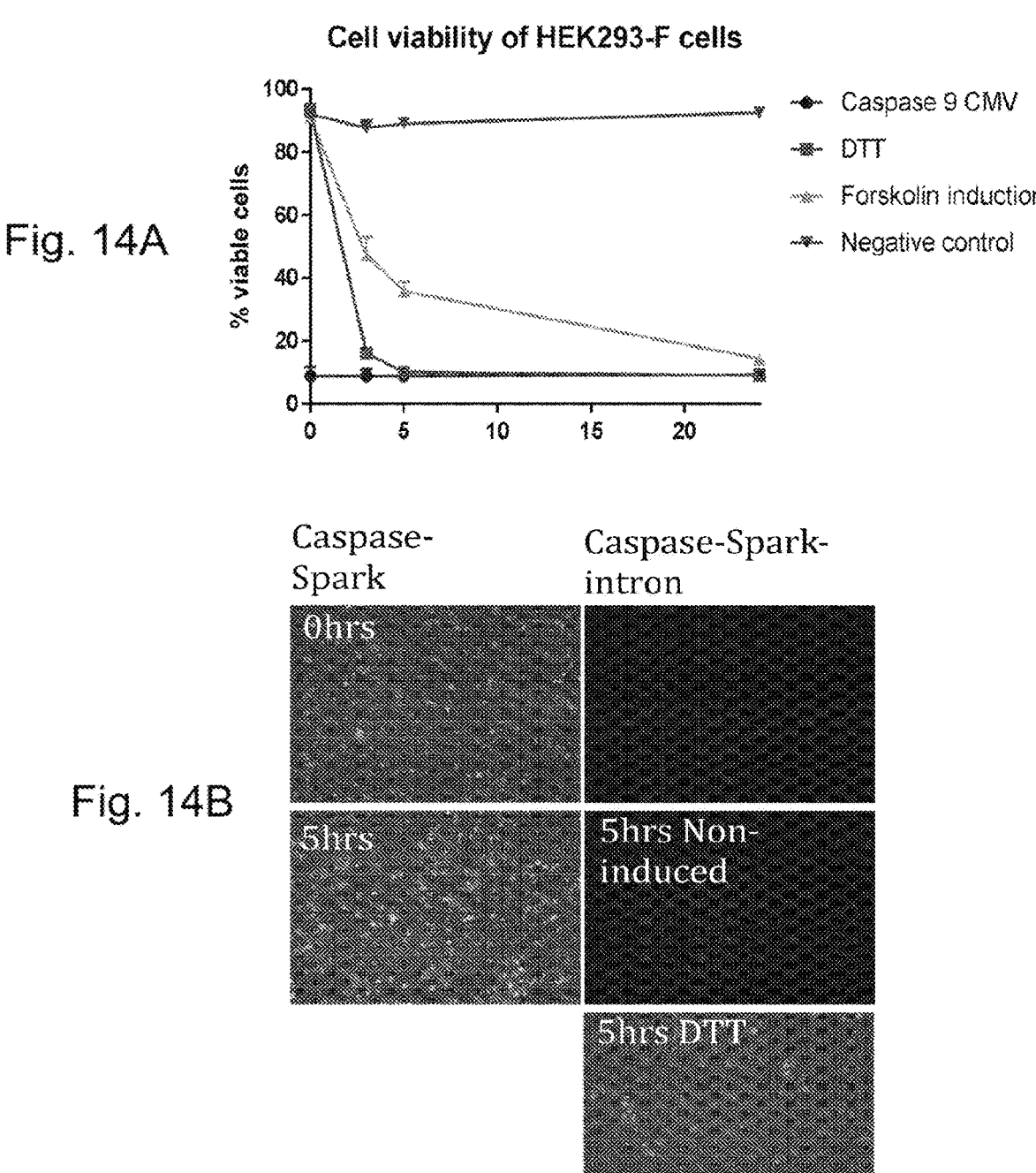
FIG. 14A shows a graph of HEK293 cell viability following induction of caspase 9 (CASP9) with DTT or forskolin, compared with a negative control and CASP9 under control of the CMV-IE promoter (X-axis shows hours after induction).
FIG. 14B shows micrographs of the fluorescent marker Spark, which was fused to CASP9, in cells where the expression construct did not contain the regulatable intron (left hand panels), and in cells where the expression construct contained the regulatable intron (right hand panels).

As can be seen in FIG. 14A, before induction there was no cell death, however upon addition of either inducer there was a rapid increase in the % of dead cells, indeed after 3 h with DTT the number of dead cells was close to the control construct which contained no intron. Indeed, 5 h after DTT treatment the % of dead cells is equal to the positive control whereas the forskolin treatment only achieved this level after 24 hrs, suggesting it is a weak inducer of splicing. Cells with no inducer added showed little or no cell death indicating that there was no expression of caspase 9 until addition of the inducing agent. This shows that control of gene expression from this is very tight (indeed apparently absolute) and at the mRNA level as the CMV-IE promoter is constitutive and therefore continually making transcripts. FIG. 14B also shows that the control of gene expression from the intron is very tight. This is because the Caspase 9 is fused to a GFP variant called SPARK, therefore expression of Caspase 9 will lead to expression of the GFP variant. This figure shows that there is no GFP expression until the addition of an inducer and cell death has begun.

Figure 15:
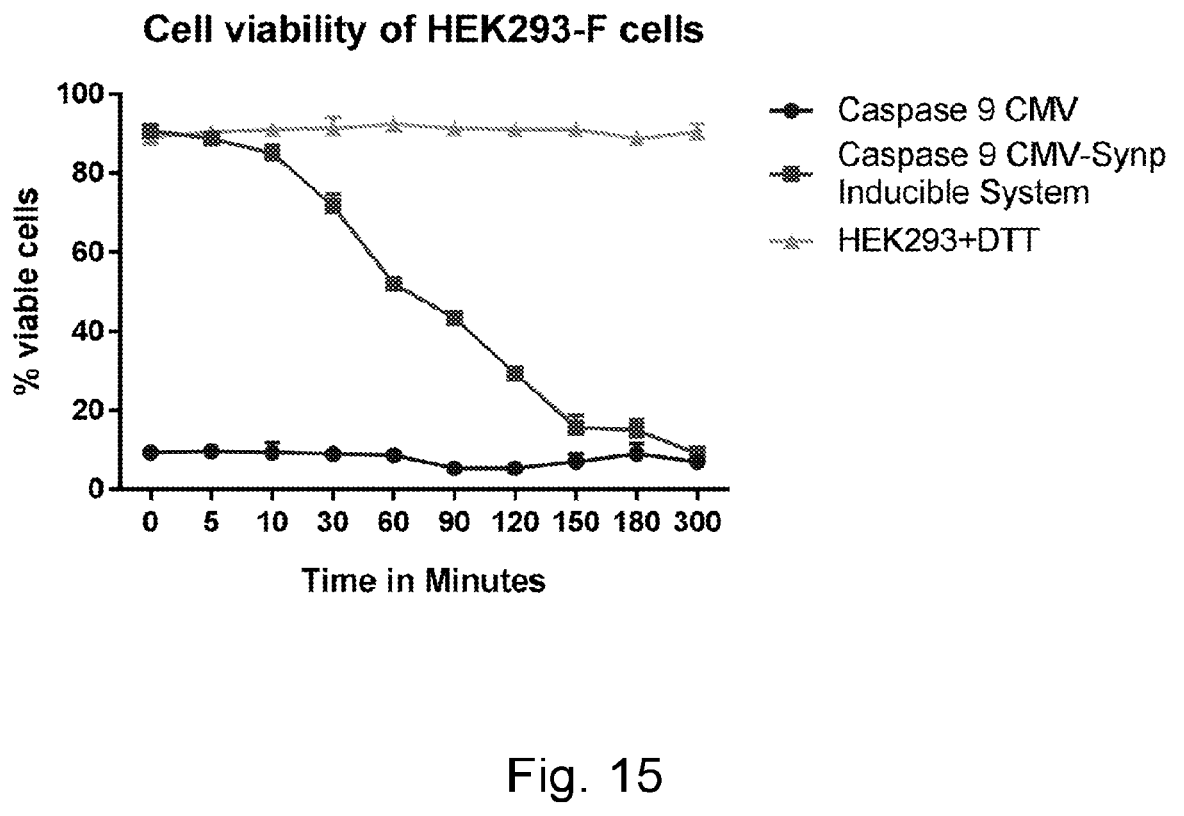

In a further experiment, the same construct as described above (SYNP-CASP9-INT) was used and the rate of cell death was measured. From this figure it can be seen that ~50% of cells die within 1 hr of induction, showing that the response is rapid as well as incredibly tightly controlled. The results of this experiment are shown in FIG. 15.

Example 8—UPR-Inducible Promoter Using Different Minimal Promoters

The purpose of this experiment was to test the ATF6-containing UPR-responsive cis-regulatory element (also referred to herein as an enhancer) as used in the examples above with different minimal promoters and to further assess their inducibilty and tightness of control. To this end, the ATF6-containing UPR-responsive cis-regulatory element was operably linked to the CMV-MP and MinTK (herpes thymidine kinase minimal promoter) minimal promoters The constructs were synthesised by GeneART by chemical synthesis, as above.

As described above, the enhancer sequence contains 6 repeats of the sequence TGACGTGCT (which contains the ATF6 consensus sequence, TGACGTG) spaced by 20 bp spacer sequences. The enhancer sequence was coupled to either MinTK (in construct ATF06-MP001) or CMV-MP (in construct ATF06-MP002).

Transfection of HEK293-F cells was performed as previously described. DTT was added at a concentration of 2 mM. Luciferase activity was measured as previously described. The results are shown in FIG. 17—the DTT was added at time=0 h as shown on the X-axis (units are hours).

Both constructs showed good inducibility and negligible expression prior to addition of the DTT. Slightly higher expression was observed for the promoter comprising CMV-MP compared with the promoter comprising MinTK. However, both promoter constructs showed high levels of expression after induction of the UPR by DTT, significantly higher than provided by the constitutive CMV-IE promoter.

ATF06-MP-001 (ATF06 and MinTK Promoter Sequence Underlined)

(SEQ ID NO: 59)
GAAGTTCCTATTCCGAAGTTCCTATTCTCTAGAAAGTATAGGAACTTC

<u>TGACGTGCTGATGATGCGTAGCTAGTAGTTGACGTGCTGATGATGCGT</u>

<u>AGCTAGTAGTTGACGTGCTGATGATGCGTAGCTAGTAGTTGACGTGCT</u>

<u>GATGATGCGTAGCTAGTAGTTGACGTGCTGATGATGCGTAGCTAGTAG</u>

<u>TTGACGTGCTGATGATGCGTAGCTAGTAGTGCAGTTAGCGTAGCTGAG</u>

<u>GTACCGYCGACGATATCGGATCCYTCGCATATTAAGGTGACGCGTGTG</u>

<u>GCCTCGAACACCGAGC</u>GACCCTGCAGCGACCCGCTTAAATGGAAGATG

CCAAAAACATTAAGAAGGGCCCAGCGCCATTCTACCCACTCGAAGACG

GGACCGCCGGCGAGCAGCTGCACAAAGCCATGAAGCGCTACGCCCTGG

TGCCCGGCACCATCGCCTTTACCGACGCACATATCGAGGTGGACATTA

CCTACGCCGAGTACTTCGAGATGAGCGTTCGGCTGGCAGAAGCTATGA

AGCGCTATGGGCTGAATACAAACCATCGGATCGTGGTGTGCAGCGAGA

ATAGCTTGCAGTTCTTCATGCCCGTGTTGGGTGCCCTGTTCATCGGTG

58

-continued
TGGCTGTGGCCCCAGCTAACGACATCTACAACGAGCGCGAGCTGCTGA

ACAGCATGGGCATCAGCCAGCCCACCGTCGTATTCGTGAGCAAGAAAG

GGCTGCAAAAGATCCTCAACGTGCAAAAGAAGCTACCGATCATACAAA

AGATCATCATCATGGATAGCAAGACCGACTACCAGGGCTTCCAAAGCA

TGTACACCTTCGTGACTTCCCATTTGCCACCCGGCTTCAACGAGTACG

ACTTCGTGCCCGAGAGCTTCGACCGGGACAAAACCATCGCCCTGATCA

TGAACAGTAGTGGCAGTACCGGATTGCCCAAGGGCGTAGCCCTACCGC

ACCGCACCGCTTGTGTCCGATTCAGTCATGCCCGCGACCCCATCTTCG

GCAACCAGATCATCCCCGACACCGCTATCCTCAGCGTGGTGCCATTTC

ACCACGGCTTCGGCATGTTCACCACGCTGGGCTACTTGATCTGCGGCT

TTCGGGTCGTGCTCATGTACCGCTTCGAGGAGGAGCTATTCTTGCGCA

GCTTGCAAGACTATAAGATTCAATCTGCCCTGCTGGTGCCCACACTAT

TTAGCTTCTTCGCTAAGAGCACTCTCATCGACAAGTACGACCTAAGCA

ACTTGCACGAGATCGCCAGCGGCGGGGCGCCGCTCAGCAAGGAGGTAG

GTGAGGCCGTGGCCAAACGCTTCCACCTACCAGGCATCCGCCAGGGCT

ACGGCCTGACAGAAACAACCAGCGCCATTCTGATCACCCCCGAAGGGG

ACGACAAGCCTGGCGCAGTAGGCAAGGTGGTGCCCTTCTTCGAGGCTA

AGGTGGTGGACTTGGACACCGGTAAGACACTGGGTGTGAACCAGCGCG

GCGAGCTGTGCGTCCGTGGCCCCATGATCATGAGCGGCTACGTTAACA

ACCCCGAGGCTACAAACGCTCTCATCGACAAGGACGGCTGGCTGCACA

GCGGCGACATCGCCTACTGGGACGAGGACGAGCACTTCTTCATCGTGG

ACCGGCTGAAGAGCCTGATCAAATACAAGGGCTACCAGGTAGCCCCAG

CCGAACTGGAGAGCATCCTGCTGCAACACCCCCAACATCTTCGACGCCG

GGGTCGCCGGCCTGCCCGACGACGATGCCGGCGAGCTGCCCGCCGCAG

TCGTCGTGCTGGAACACGGTAAAACCATGACCGAGAAGGAGATCGTGG

ACTATGTGGCCAGCCAGGTTACAACCGCCAAGAAGCTGCGCGGTGGTG

TTGTGTTCGTGGACGAGGTGCCTAAAGGACTGACCGGCAAGTTGGACG

CCCGCAAGATCCGCGAGATTCTCATTAAGGCCAAGAAGGGCGGCAAGA

TCGCCGTGTAATGAAAGCTTGGTCTCTACGAGTAATAGACGCCCAGTT

GAATTCCTTCGAGCAGACATGATAAGATACATTGATGAGTTTGGACAA

ACCACAACTAGAATGCAGTGAAAAAAATGCTTTATTTGTGAAATTTGT

GATGCTATTGCTTTATTTGTAACCATTATAAGCTGCAATAAACAAGTT

AACAACAACAATTGCATTCATTTTATGTTTCAGGTTCAGGGGGGAGGTG

TGGGAGGTTTTTTAAAGCAAGTAAAACCTCTACAAATGTGGTAAAATC

GATAAGGATCCGT

ATF06-MP-002 (ATF06 and CMV-MP Promoter Sequence Underlined)

(SEQ ID NO: 60)
GCGACGTAATACGACTCACTATAGGGCGAATTGGCGGAAGGCCGTCAA

GGCCGCATGCATAATAAAATATCTTTATTTTCATTACATCTGTGTGTT

GGTTTTTTGTGTGTGACGTGCTGATGATGCGTAGCTAGTAGTTGACGT

-continued

GCTGATGATGCGTAGCTAGTAGTTGACGTGCTGATGATGCGTAGCTAG

TAGTTGACGTGCTGATGATGCGTAGCTAGTAGTTGACGTGCTGATGAT

GCGTAGCTAGTAGTTGACGTGCTGATGATGCGTAGCTAGTAGTGCAGT

TAGCGTAGCTGAGGTACCGTCGACGATATCGGATCCAGGTCTATATAA

GCAGAGCTCGTTTAGTGAACCGTCAGATCGCCTAGATACGCCATCCAC

GCTGTTTTGACCTCCATAGAAGATCGCCACCATGGAAGATGCCAAAAA

CATTAAGAAGGGCCCAGCGCCATTCTACCCACTCGAAGACGGGACCGC

CGGCGAGCAGCTGCACAAAGCCATGAAGCGCTACGCCCTGGTGCCCGG

CACCATCGCCTTTACCGACGCACATATCGAGGTGGACATTACCTACGC

CGAGTACTTCGAGATGAGCGTTCGGCTGGCAGAAGCTATGAAGCGCTA

TGGGCTGAATACAAACCATCGGATCGTGGTGTGCAGCGAGAATAGCTT

GCAGTTCTTCATGCCCGTGTTGGGTGCCCTGTTCATCGGTGTGGCTGT

GGCCCCAGCTAACGACATCTACAACGAGCGCGAGCTGCTGAACAGCAT

GGGCATCAGCCAGCCCACCGTCGTATTCGTGAGCAAGAAAGGGCTGCA

AAAGATCCTCAACGTGCAAAAGAAGCTACCGATCATACAAAAGATCAT

CATCATGGATAGCAAGACCGACTACCAGGGCTTCCAAAGCATGTACAC

CTTCGTGACTTCCCATTTGCCACCCGGCTTCAACGAGTACGACTTCGT

GCCCGAGAGCTTCGACCGGGACAAAACCATCGCCCTGATCATGAACAG

TAGTGGCAGTACCGGATTGCCCAAGGGCGTAGCCCTACCGCACCGCAC

CGCTTGTGTCCGATTCAGTCATGCCCGCGACCCCATCTTCGGCAACCA

GATCATCCCCGACACCGCTATCCTCAGCGTGGTGCCATTTCACCACGG

CTTCGGCATGTTCACCACGCTGGGCTACTTGATCTGCGGCTTTCGGGT

CGTGCTCATGTACCGCTTCGAGGAGGAGCTATTCTTGCGCAGCTTGCA

AGACTATAAGATTCAATCTGCCCTGCTGGTGCCCACACTATTTAGCTT

CTTCGCTAAGAGCACTCTCATCGACAAGTACGACCTAAGCAACTTGCA

CGAGATCGCCAGCGGCGGGGCGCCGCTCAGCAAGGAGGTAGGTGAGGC

CGTGGCCAAACGCTTCCACCTACCAGGCATCCGCCAGGGCTACGGCCT

GACAGAAACAACCAGCGCCATTCTGATCACCCCCGAAGGGGACGACAA

5 GCCTGGCGCAGTAGGCAAGGTGGTGCCCTTCTTCGAGGCTAAGGTGGT

GGACTTGGACACCGGTAAGACACTGGGTGTGAACCAGCGCGGCGAGCT

GTGCGTCCGTGGCCCCATGATCATGAGCGGCTACGTTAACAACCCCGA

10 GGCTACAAACGCTCTCATCGACAAGGACGGCTGGCTGCACAGCGGCGA

CATCGCCTACTGGGACGAGGACGAGCACTTCTTCATCGTGGACCGGCT

GAAGAGCCTGATCAAATACAAGGGCTACCAGGTAGCCCCAGCCGAACT

15 GGAGAGCATCCTGCTGCAACACCCCAACATCTTCGACGCCGGGGTCGC

CGGCCTGCCCGACGACGATGCCGGCGAGCTGCCCGCCGCAGTCGTCGT

GCTGGAACACGGTAAAACCATGACCGAGAAGGAGATCGTGGACTATGT

20 GGCCAGCCAGGTTACAACCGCCAAGAAGCTGCGCGGTGGTGTTGTGTT

CGTGGACGAGGTGCCTAAAGGACTGACCGGCAAGTTGGACGCCCGCAA

GATCCGCGAGATTCTCATTAAGGCCAAGAAGGGCGGCAAGATCGCCGT

GTAATGAAAGCTTGGTCTCTACGAGTAATAGACGCCCAGTTGAATTCC

25 TTCGAGCAGACATGATAAGATACATTGATGAGTTTGGACAAACCACAA

CTAGAATGCAGTGAAAAAAATGCTTTATTTGTGAAATTTGTGATGCTA

TTGCTTTATTTGTAACCATTATAAGCTGCAATAAACAAGTTAACAACA

30 ACAATTGCATTCATTTTATGTTTCAGGTTCAGGGGGAGGTGTGGGAGG

TTTTTTAAAGCAAGTAAAACCTCTACAAATGTGGTAAAATCGATAAGG

ATCCGTCTGGGCCTCATGGGCCTTCCGCTCACTGCCCGCTTTCCAGTC

35 GGGAAACCTGTCGTGCCAGCTGCAT

While the making and using of various embodiments of the present invention are discussed in detail above, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

The invention claimed is:

1. A synthetic nucleic acid expression construct comprising a nucleic acid comprising a sequence encoding an expression product, the sequence encoding an expression product comprising a sequence which encodes a regulatable intron, said regulatable intron being an intron which comprises an excisable sequence which is capable of being spliced out of a transcript produced from the synthetic expression construct via the unfolded protein response (UPR) system in the cell, thereby resulting in a transcript encoding a functional expression product, wherein the regulatable intron comprises the sequence CNG/CNG-Xn-CNG/CNG, wherein Xn represents a sequence of length n bases, wherein/represents a cleavage site and wherein the sequence CNG-Xn-CNG is excised from the transcript; or wherein the regulatable intron comprises the sequence CNG/CNG-Xn-CNG/CNG, wherein Xn represents a sequence of length n nucleotides, wherein/represents the cleavage site such that the excisable sequence CNG-Xn-CNG is excised from the transcript upon splicing, and wherein the nucleotide at the 5' end of the sequence Xn is a C or G, and wherein the expression product is not the XBP1 protein, Hac1 protein, bZIP60 protein or a homologue thereof.

2. A vector comprising the synthetic nucleic acid expression construct of claim 1.

3. A cell comprising the nucleic acid expression construct of claim 1.

4. The cell of claim 3, wherein the cell is a eukaryotic cell.

5. The cell according to claim 3 wherein the nucleic acid expression construct encodes an expression product that is toxic to the cell.

6. A method for producing an expression product, the method comprising:

a) providing a population of eukaryotic cells comprising a synthetic nucleic acid expression construct according to according to claim 1;

b) treating said population of cells so as to induce the unfolded protein response, thereby inducing splicing of the excisable sequence out of the regulatable intron;

c) incubating said population of cells under suitable conditions for production of the expression product; and d) isolating the expression product from said population of cells.

7. The method according to claim 6 which comprises incubating said population of cells under conditions suitable for growth of the cells prior to step b) of treating said population of cells so as to induce the unfolded protein response (UPR).

8. The method according to claim 6 wherein step b) comprises applying a stress to said cells, said stress being suitable to induce the UPR, or wherein step b) comprises administering a chemical agent that is able to induce the UPR in said cells.

9. The method according to claim 8 wherein the chemical agent that is able to induce the UPR in said cells comprises one or more of forskolin, dithiothreitol (DTT), tunicamycin, thapsigargin, a saturated fatty acid, an agent that is able to downregulate stearoyl-CoA desaturase enzyme activity.

10. The method according to claim 6 wherein step b) comprises expressing an inducer protein in said population of eukaryotic cells so as to induce the UPR response in the population of cells, or wherein step b) comprises transfecting said population of cells with an expression vector that is capable of expressing an inducer protein, preferably a heterologous protein, in said cells, or wherein step b) comprises inducing expression of the inducer protein from an expression vector that was previously introduced into the cells.

11. The method according to claim 6 wherein step b) comprises exposing the cells to hypoxia or carbohydrate deprivation.

12. The method according to claim 6 wherein the population of cells comprises fungal cells, animal cells, or plant cells, preferably wherein the population of cells comprises mammalian cells.

13. The method according to claim 6 which comprises, prior to step a), the step of introducing the nucleic acid expression construct into the cells.

14. A method for gene therapy in a subject in need of said gene therapy comprising:

-introducing into the subject a gene therapy vector comprising a nucleic acid expression construct according to claim 1, the nucleic acid expression construct comprising a sequence encoding a therapeutic expression product such that the gene therapy vector delivers the nucleic acid expression construct to target cells of the subject; and expressing a therapeutically effective amount of the functional therapeutic expression product in target cells of subject.

* * * * *